US011491206B1

(12) United States Patent
Chilkoti et al.

(10) Patent No.: US 11,491,206 B1
(45) Date of Patent: Nov. 8, 2022

(54) COMPOSITIONS AND METHODS FOR THE TREATMENT OF TRAIL-RESISTANT CANCER

(71) Applicant: Duke University, Durham, NC (US)

(72) Inventors: Ashutosh Chilkoti, Durham, NC (US);
Kris Wood, Durham, NC (US);
Mandana Manzari, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/274,978

(22) Filed: Feb. 13, 2019

Related U.S. Application Data

(60) Provisional application No. 62/629,852, filed on Feb. 13, 2018.

(51) Int. Cl.
| | |
|---|---|
| *C07K 14/78* | (2006.01) |
| *C07K 19/00* | (2006.01) |
| *A61K 38/39* | (2006.01) |
| *A61K 31/40* | (2006.01) |
| *A61K 31/428* | (2006.01) |
| *A61K 31/4725* | (2006.01) |
| *A61K 31/519* | (2006.01) |
| *A61K 9/00* | (2006.01) |
| *A61P 35/00* | (2006.01) |

(52) U.S. Cl.
CPC ............ *A61K 38/39* (2013.01); *A61K 9/0004* (2013.01); *A61K 9/0019* (2013.01); *A61K 31/40* (2013.01); *A61K 31/428* (2013.01); *A61K 31/4725* (2013.01); *A61K 31/519* (2013.01); *A61P 35/00* (2018.01); *C07K 14/78* (2013.01); *C07K 2319/00* (2013.01); *C07K 2319/75* (2013.01)

(58) Field of Classification Search
CPC .......... A61K 2039/505; A61K 39/3955; A61K 38/00; A61K 38/177; A61K 38/39; A61K 31/40; A61K 31/428; A61K 31/4725; A61K 31/519; C07K 14/78; C07K 2319/00; C07K 2319/75
See application file for complete search history.

(56) References Cited

U.S. PATENT DOCUMENTS

| | | | |
|---|---|---|---|
| 5,580,859 | A | 12/1996 | Felgner et al. |
| 5,679,647 | A | 10/1997 | Carson et al. |
| 5,703,055 | A | 12/1997 | Felgner et al. |
| 8,221,765 | B2 | 7/2012 | Camphausen et al. |
| 9,212,231 | B2 | 12/2015 | Baca et al. |
| 2011/0142796 | A1 | 6/2011 | Connors et al. |
| 2013/0079280 | A1 | 3/2013 | Baca et al. |
| 2017/0182179 | A1 | 6/2017 | Ackler et al. |

FOREIGN PATENT DOCUMENTS

WO    WO 2016/154530 A1    9/2016

OTHER PUBLICATIONS

Amarante-Mendes et al. Therapeutic applications of TRAIL receptor agonists in cancer and beyond. Pharmacol Therapeutics 155: 117-131, 2015.*
Bailon-Moscoso et al. Natural compounds as modulators of cell cycle arrest: application for anticancer chemotherapies. Current Genomics 18: 106-131, 2017.*
Dai et al. Targeting TNF-related apoptosis-inducing ligand (TRAIL) receptor by natural products as a potential therapeutic approach for cancer therapy. Exp Biol Med 240: 760-773, 2015.*
Despanie et al. Elastin-like polypeptides: therapeutic applications for an emerging class of nanomedicines. J Controlled Release 240:93-108, 2016.*
Desrat et al. From meiogynin A to the synthesis of dual inhibitors of Bcl-xl and Mcl-1 anti-apoptotoc proteins. Chem Comm 50: 8593-8596, 2014.*
Fulda et al. Smac agonists sensitize for Apo2L/TRAIL- or anticancer drug-induced apoptosis and induce regression of malignant glioma in vivo. Nature Med 8(8): 808-815, 2002.*
Gamie et al. TNF-related apoptosis-inducing ligand (TRAIL) for bone sarcoma treatment: pre-clinical and clinical data. Cancer Lett 409:66-80, 2017.*
Hamilton et al. A phase 1b, openlabel, nonrandomized multicenter study of birinapant in combination with conatumumab in subjects with relapsed epithelial ovarian cancer, primary peritoneal cancer, or fallopian tube cancer. J Clin Oncol 33(Suppl 1): 15, 2015.*
Jeong et al. Cannabidiol promotes apoptosis via regulation of XIAP/Smac in gastric cancer. Cell Death Disease 10: 846, 2019 (13 total pages).*
Moretti et al. AT-101, a pan-Bcl-2 inhibitor, leads to radiosensitization of non-small cell lung cancer. J Thorac Oncol 5: 680-687, 2010.*
Munoz et al. XIAP as a target of new small organic natural molecules inducing human cancer cell death. Cancers 11: 1336, 2019 (30 total pages).*
Prabhu et al. Targeting of X-linked inhibitor of apoptosis protein and PI3-kinase/AKT signaling by embelin suppresses growth of leukemic cells. PLOS One 12(7): e0180895, 2017 (17 total pages).*
Rathore et al. Overcoming chemotherapy drug resistance by targeting inhibitors of apoptosis proteins (IAPs). Apoptosis 22: 898-919, 2017.*
Raulf et al. Differential response of head and neck cancer cell lines to TRAIL or Smac mimetics is associated with the cellular levels and activity of caspase-8 and caspase-10. Brit J Cancer 111: 1955-1964, 2014.*

(Continued)

*Primary Examiner* — Bridget E Bunner
(74) *Attorney, Agent, or Firm* — Michael Best & Friedrich LLP

(57) ABSTRACT

Embodiments of the present disclosure relate generally to the treatment of cancer involving activation of the tumor necrosis factor-related apoptosis inducing ligand receptor (TRAILR) pathway. In particular, the present disclosure provides compositions and methods for the identification of genes conferring TRAIL resistance, and the development of rational drug combinations targeting these genes. The therapeutic drug combinations of the present disclosure function synergistically to sensitize cancer cells to TRAIL-resistant cancers.

5 Claims, 40 Drawing Sheets

Specification includes a Sequence Listing.

(56) References Cited

OTHER PUBLICATIONS

Roesler et al. Cooperative TRAIL production mediates IFNa/Smac mimetic-induced cell death in TNFa-resistant solid cancer cells. Oncotarget 7(4): 3709-3725, 2016.*
Tahir et al. Abbv-621 is a novel and potent TRAIL receptor agonist fusion protein that induces apoptosis alone and in combination with navitoclaxand venetoclaxin hematological tumors. Blood 130 (Suppl 1): 2812, 2017.*
Vogler et al. Small molecules XIAP inhibitors enhance TRAIL-induced apoptosis and antitumor activity in preclinical models of pancreatic carcinoma. Cancer Res 69(6): 2425-2434, 2009.*
Wiley et al. Identification and characterization of a new member of the TNF family that induces apoptosis. Immunity 3: 673-682, 1995.*
El-Mesery et al. The SMAC mimetic BV6 induces cell death and sensitizes different cell lines to TNF-alpha and TRAIL-induced apoptosis. Exp Biol Med 241: 2015-2022, 2016.*
Allen et al., "Genetic and pharmacological screens converge in identifying FLIP, BCL2, and IAP proteins as key regulators of sensitivity to the TRAIL-inducing anticancer agent ONC201/TIC10," Cancer Res, 2015, 75, 1668-1674.
Amiram et al., "A depot-forming glucagon-like peptide-1 fusion protein reduces blood glucose for five days with a single injection," J Control Release, 2013, 172, 144-151.
Amiram et al., "Injectable protease-operated depots of glucagon-like peptide-1 provide extended and tunable glucose control," Proc Natl Acad Sci USA, 2013, 110, 2792-2797.
Anderson et al., "A landscape of therapeutic cooperativity in KRAS mutant cancers reveals principles for controlling tumor evolution," Cell Rep, 2017, 20, 999-1015.
Anderson et al., "PIK3CA mutations enable targeting of a breast tumor dependency through mTOR-mediated MCL-1 translation," Sci Transl Med, 2016, 8, 369ra175, 14 pages.
ASCO, "Cost of Cancer Drugs Should Be Part of Treatment Decisions," Oct. 30, 2015. Retrieved on Oct. 8, 2017, from <https://am.asco.org/cost-cancer-drugs-should-be-part-treatment-decisions>.
Ashkenazi, "Targeting the extrinsic apoptotic pathway in cancer: lessons learned and future directions," J Clin Invest, 2015, 125, 487-489.
Barui et al., "Simultaneous delivery of doxorubicin and curcumin encapsulated in liposomes of pegylated RGDK-lipopeptide to tumor vasculature," Biomaterials, 2014, 35, 1643-1656.
Chilkoti et al., "Stimulus responsive elastin biopolymers: Applications in medicine and biotechnology," Curr Opin Chem Biol, 2006, 10, 652-657.
Connolly et al., "Stable XIAP knockdown clones of HCT116 colon cancer cells are more sensitive to TRAIL, taxanes and irradiation in vitro," Cancer Chemother Pharmacol, 2009, 64, 307-316.
Cummins et al., "X-Linked Inhibitor of Apoptosis Protein (XIAP) Is a Nonredundant Modulator of Tumor Necrosis Factor-Related Apoptosis-Inducing Ligand (TRAIL)—Mediated Apoptosis in Human Cancer Cells," Cancer Research, 2004, 64, 3006-3008.
De Melo-Diogo et al., "Combinatorial delivery of Crizotinib-Palbociclib-Sildenafil using TPGS-PLA micelles for improved cancer treatment," Eur J Pharm Biopharm, 2014, 88, 718-729.
De Miguel et al., "Onto better TRAILS for cancer treatment," Cell Death Differ, 2016, 23, 733-747.
Devetzi et al., "Death receptor 5 (DR5) and a 5-gene apoptotic biomarker panel with significant differential diagnostic potential in colorectal cancer," Sci Rep, 2016, 6, 36532, 14 pages.
Dewhirst et al., "Transport of drugs from blood vessels to tumour tissue," Nat Rev Cancer, 2017, 17, 738-750.
Donnelly et al., "DNA Vaccines," Ann. Rev. Immunol., 1997, 15, 617-648.
Ehrenschwender et al., "XIAP-targeting drugs re-sensitize PIK3CA-mutated colorectal cancer cells for death receptor-induced apoptosis," Cell Death Dis, 2014, 5, e1570, 12 pages.

Fellmann et al., "Cornerstones of CRISPR-Cas in drug discovery and therapy," Nat Rev Drug Discov, 2017, 16, 89-100.
Fox et al., "Targeting cell death signalling in cancer: minimising 'Collateral damage'," Br J Cancer, 2016, 115, 5-11.
Fry et al., "Specific inhibition of cyclin-dependent kinase 4/6 by PD 0332991 and associated antitumor activity in human tumor xenografts," Mol Cancer Ther, 2004, 3, 1427-1438.
Fulda et al., "Inhibition of TRAIL-induced apoptosis by Bcl-2 overexpression," Oncogene, 2002, 21, 2283-2294.
Gilbert et al., "Genome-scale CRISPR-mediated control of gene repression and activation," Cell, 2014, 159, 647-661.
Gilroy et al., "Fusion of fibroblast growth factor 21 to a thermally responsive biopolymer forms an injectable depot with sustained anti-diabetic action," J Control Release, 2018, 277, 154-164.
Guzman et al., "ColonyArea: an ImageJ plugin to automatically quantify colony formation in clonogenic assays," PLoS One, 2014, 9, e92444, 9 pages.
Hassouneh et al., "Fusions of elastin-like polypeptides to pharmaceutical proteins," Methods Enzymol, 2012, 502, 215-237.
Hehlgans et al., "The SMAC mimetic BV6 sensitizes colorectal cancer cells to ionizing radiation by interfering with DNA repair processes and enhancing apoptosis," Radiat Oncol, 2015, 10:198, 11 pages.
Hong et al., "Integrated genetic and pharmacologic interrogation of rare cancers," Nat Commun, 2016, 7, 11987, 9 pages.
Jost et al., "XIAP acts as a switch between type I and type II FAS-induced apoptosis," Nature, 2009, 460, 1035-1039.
Kaplan-Lefko et al., "Conatumumab, a fully human agonist antibody to death receptor 5, induces apoptosis via caspase activation in multiple tumor types," Cancer Biology & Therapy, 2014, 9, 618-631.
Lau et al., "Therapeutic peptides: Historical perspectives, current development trends, and future directions," Bioorg Med Chem, 2018, 26, 2700-2707.
Lemke et al., "Getting TRAIL back on track for cancer therapy," Cell Death Differ, 2014, 21, 1350-1364.
Lessene et al., "Structure-guided design of a selective BCL-X(L) inhibitor," Nat Chem Biol, 2013, 9, 390-397.
Letai, "Functional precision cancer medicine-moving beyond pure genomics," Nat Med, 2017, 23, 1028-1035.
Leverson et al., "Exploiting selective BCL-2 family inhibitors to dissect cell survival dependencies and define improved strategies for cancer therapy," Sci Transl Med, 2015, 7, 279ra240, 11 pages.
Li et al., "Apoptotic and antitumor activity of death receptor antibodies require inhibitory Fcγ receptor engagement," Proc Natl Acad Sci USA, 2012, 109, 10966-10971.
Liu et al., "Tumor accumulation, degradation and pharmacokinetics of elastin-like polypeptides in nude mice," J Control Release, 2006, 116, 170-178.
Lueck et al., "Smac mimetic induces cell death in a large proportion of primary acute myeloid leukemia samples, which correlates with defined molecular markers," Oncotarget, 2016, 7, 49539-49551.
Luginbuhl et al., "One-week glucose control via zero-order release kinetics from an injectable depot of glucagon-like peptide-1 fused to a thermosensitive biopolymer," Nat Biomed Eng, 2017, 1, 0078.
MacEwan et al., "Elastin-like polypeptides: biomedical applications of tunable biopolymers," Biopolymers, 2010, 94, 60-77.
Martz et al., "Systematic identification of signaling pathways with potential to confer anticancer drug resistance," Sci Signal, 2014, 7, ra121, 22 pages.
McDaniel et al., "A unified model for de novo design of elastin-like polypeptides with tunable inverse transition temperatures," Biomacromolecules, 2013, 14, 2866-2872.
McDaniel et al., "Recursive directional ligation by plasmid reconstruction allows rapid and seamless cloning of oligomeric genes," Biomacromolecules, 2010, 11, 944-952.
McLornan et al., "Prognostic significance of TRAIL signaling molecules in stage II and III colorectal cancer," Clin Cancer Res, 2010, 16, 3442-3451.
Meyer et al., "Genetically encoded synthesis of protein-based polymers with precisely specified molecular weight and sequence by recursive directional ligation: examples from the elastin-like polypeptide system," Biomacromolecules, 2002, 3, 357-367.

(56) References Cited

OTHER PUBLICATIONS

Meyer et al., "Purification of recombinant proteins by fusion with thermally-responsive polypeptides," Nat Biotechnol, 1999, 17, 1112-1115.
National Cancer Institute, "Cancer Stat Facts: Colorectal Cancer," <https://seer.cancer.gov/statfacts/html/colorect.html> webpage available as early as Nov. 12, 2005.
Ndozangue-Touriguine et al., "A mitochondrial block and expression of XIAP lead to resistance to TRAIL-induced apoptosis during progression to metastasis of a colon carcinoma," Oncogene, 2008, 27, 6012-6022.
Obexer et al., "X-linked inhibitor of apoptosis protein—a critical death resistance regulator and therapeutic target for personalized cancer therapy," Front Oncol, 2014, 4, 197, 9 pages.
Pisal et al., "Delivery of therapeutic proteins," J Pharm Sci, 2010, 99, 2557-2575.
Prentice, "A generalization of the probit and logit methods for dose response curves," Biometrics, 1976, 32, 761-768.
Raucher et al., "Enhanced uptake of a thermally responsive polypeptide by tumor cells in response to its hyperthermia-mediated phase transition," Cancer Res, 2001, 61, 7163-7170.
Schoenwaelder et al., "Bcl-xL inhibitory BH3 mimetics can induce a transient thrombocytopathy that undermines the hemostatic function of platelets," Blood, 2011, 118(6):1663-1674.
Shalem et al., "Genome-scale CRISPR-Cas9 knockout screening in human cells," Science, 2014, 343, 84-87.
Stuckey et al., "TRAIL on trial: preclinical advances in cancer therapy," Trends Mol Med, 2013, 19, 685-694.
Swers et al., "Multivalent scaffold proteins as superagonists of TRAIL receptor 2-induced apoptosis," Mol Cancer Ther, 2013, 12, 1235-1244.
Tao et al., "Discovery of a Potent and Selective BCL-XL Inhibitor with in Vivo Activity," ACS Med Chem Lett, 2014, 5, 1088-1093.
The Cancer Genome Atlas Research Network, "Integrated genomic and molecular characterization of cervical cancer," Nature, 2017, 543, 378-384.
Toogood et al., "Discovery of a potent and selective inhibitor of cyclin-dependent kinase 4/6," J Med Chem, 2005, 48, 2388-2406.
Van Dijk et al., "Resistance to TRAIL in non-transformed cells is due to multiple redundant pathways," Cell Death & Disease, 2013, 4, e702, 50 pages.
Varfolomeev et al., "X chromosome-linked inhibitor of apoptosis regulates cell death induction by proapoptotic receptor agonists," J Biol Chem, 2009, 284, 34553-34560.
Von Karstedt et al., "Exploring the TRAILs less travelled: TRAIL in cancer biology and therapy," Nat Rev Cancer, 2017, 17, 352-366.
Wagner et al., "Death-receptor O-glycosylation controls tumor-cell sensitivity to the proapoptotic ligand Apo2L/TRAIL," Nat Med, 2007, 13, 1070-1077.
Wang et al., "Genetic screens in human cells using the CRISPR-Cas9 system," Science, 2014, 343, 80-84.
Wilson et al., "An Fcγ Receptor-Dependent Mechanism Drives Antibody-Mediated Target-Receptor Signaling in Cancer Cells," Cancer Cell, 2011, 19, 101-113.
Wittrup et al., "Practical theoretic guidance for the design of tumor-targeting agents," Methods Enzymol, 2012, 503, 255-268.
Xiao et al., "Co-delivery of daunomycin and oxaliplatin by biodegradable polymers for safer and more efficacious combination therapy," J Control Release, 2012, 163, 304-314.
Yang et al., "A public genome-scale lentiviral expression library of human ORFs," Nat Methods, 2011, 8, 659-661.

\* cited by examiner

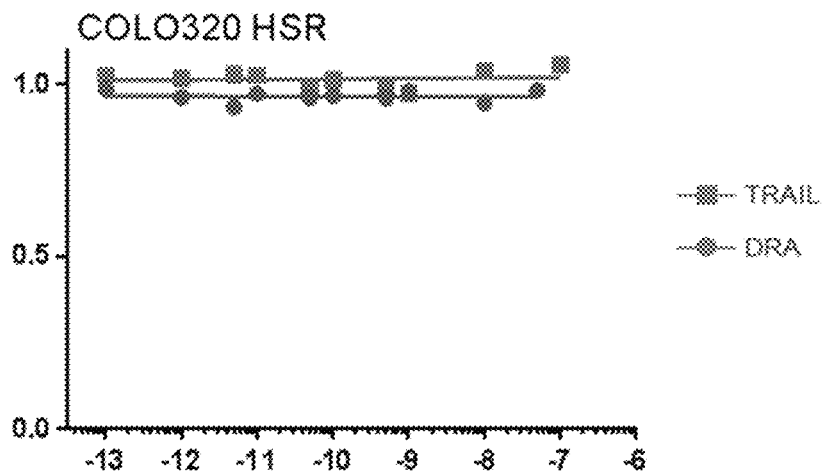
FIG. 3E
| | A<br>HCT116 | B<br>HCT15 | C<br>DLD-1 | D<br>T84 | E<br>HT29 | F<br>COLO205 | G<br>LOVO | H<br>RKO | I<br>COLO320 |
|---|---|---|---|---|---|---|---|---|---|
| TRAIL EC$_{50}$ [M] | 6.30E-10 | 5.80E-09 | 4.70E-09 | ~5.1E-05 | RESISTANT | 2.70E-09 | ~1.2E-08 | RESISTANT | RESISTANT |
| DRA EC$_{50}$ [M] | 1.4E-12 | 1.7E-11 | 1.7E-11 | 1.8E-11 | 1.5E-11 | 1.6E-12 | 1.7E-10 | RESISTANT | RESISTANT |
| T/D Fold Increase | 450 | 340 | 280 | 2,800,000 | N/A | 1688 | 71 | | |
FIG. 3F
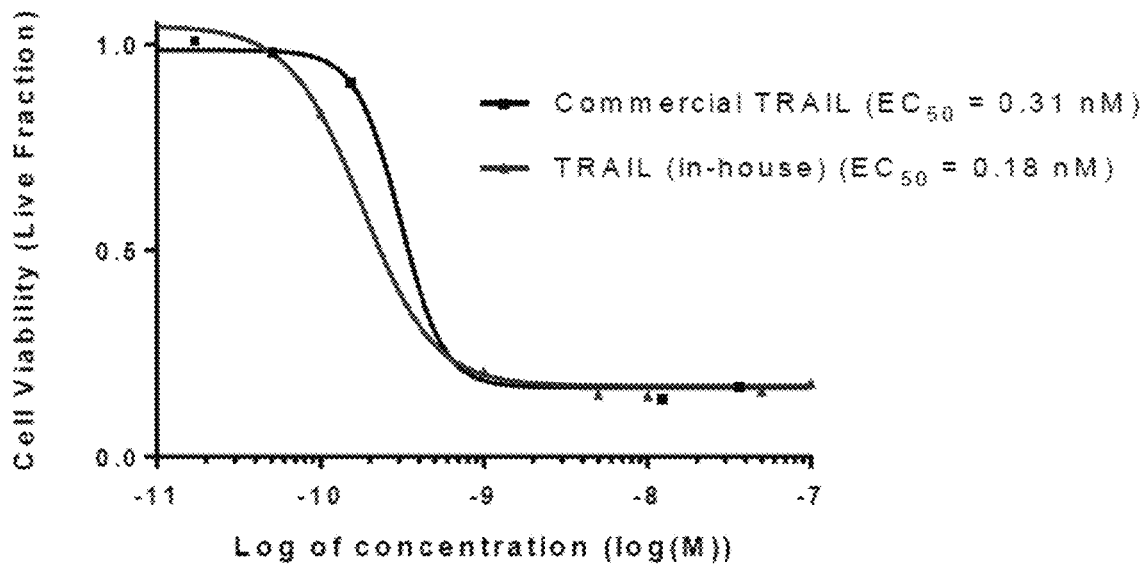
FIG. 4

```
                           SEQUENCE LISTING

<160> NUMBER OF SEQ ID NOS: 4

<210> SEQ ID NO 1
<211> LENGTH: 89
<212> TYPE: PRT
<213> ORGANISM: Artificial Sequence
<220> FEATURE:
<223> OTHER INFORMATION: Synthetic

<400> SEQUENCE: 1

Gly Ala Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Asp Leu
        35                  40                  45

Gln Gln Lys His Thr Ala Tyr Ser Ile Gly Asn Leu Lys Pro Asp Thr
    50                  55                  60

Glu Tyr Glu Val Ser Leu Ile Cys Phe Asp Pro Tyr Gly Met Arg Ser
65                  70                  75                  80

Lys Pro Ala Lys Glu Thr Phe Thr Thr
                85

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: sequence may repeat one or more times
<220> FEATURE:
<221> NAME/KEY: Xaa
<222> LOCATION: (4)..(4)
<223> OTHER INFORMATION: X is any amino acid except proline
```

```
<400> SEQUENCE: 3

Val Pro Gly Xaa Gly
1               5

<210> SEQ ID NO 4
<211> LENGTH: 26
<212> TYPE: PRT
<213> ORGANISM: Artificial Sequence
<220> FEATURE:
<223> OTHER INFORMATION: Synthetic

<400> SEQUENCE: 4

Met Thr Asn Ile Thr Lys Arg Ser Leu Val Ala Ala Gly Val Leu Ala
1               5                   10                  15

Ala Leu Met Ala Gly Asn Val Ala Leu Ala
            20                  25
```

COMPOSITIONS AND METHODS FOR THE TREATMENT OF TRAIL-RESISTANT CANCER

CROSS-REFERENCE TO RELATED APPLICATIONS

This application claims priority to U.S. Provisional Application No. 62/629,852, filed Feb. 13, 2018, which is hereby incorporated by reference in its entirety.

GOVERNMENT FUNDING

The subject matter of this invention was made with Government support under Federal Grant Nos. 2032358 and 2032363 awarded by the National Institutes of Health (NIH). The Government has certain rights to this invention.

SEQUENCE LISTING

The instant application contains a Sequence Listing which has been submitted electronically and is hereby incorporated by reference in its entirety. The sequence listing text filed, created on Feb. 12, 2019, is named "028193-9282-US02_As_Filed_Sequence_Listing" and is 2,018 bytes in size.

FIELD

Embodiments of the present disclosure relate generally to the treatment of cancer involving activation of the tumor necrosis factor-related apoptosis inducing ligand receptor (TRAILR) pathway. In particular, the present disclosure provides compositions and methods for the identification of genes conferring TRAIL resistance, and the development of rational drug combinations targeting these genes. The therapeutic drug combinations of the present disclosure function synergistically to sensitize cancer cells to TRAIL-resistant cancers.

BACKGROUND

The majority of primary cancer cells are TRAIL-resistant (i.e., resistant to tumor necrosis factor-related apoptosis inducing ligand, or TRAIL). Although mechanisms of TRAIL resistance are distinct among cancer cell types, they commonly include: reduced cell surface DR expression, inhibited caspase-8 activation (i.e., an initiator caspase), upregulated anti-apoptotic molecules (e.g., Bcl-2 and the inhibitors of apoptosis (IAP) family proteins), and reduced expression of pro-apoptotic markers like Bax/Bak. The role of diverse molecules like anticancer agents and natural compounds in sensitizing TRAIL-resistant cancer cells has been investigated and introduced as an addition to TRAIL monotherapy. TRAIL-based combinations were well validated in vitro and in a few in vivo cancer models; however, they fail to demonstrate a similar synergy in cancer patients.

Over the past twenty years, TNF-related apoptosis-inducing ligand (TRAIL) was shown to kill a variety of human cancer cells in vitro and in vivo while remaining innocuous to healthy cells. Unfortunately, the preclinical promise of TRAIL and other agonists of TRAIL receptors (TRAILR1 and TRAILR2) has not translated to clinical efficacy for patients. Significant efforts have been made to illuminate the shortcomings of TRAIL receptor agonists. These efforts include two strategies for overcoming tumor resistance to these therapeutics: (1) improving the potency of TRAs and (2) rationally designing combination treatments that increase tumor susceptibility to these drugs. Previous studies have demonstrated that a super-potent TRAILR-2 agonist, or superagonist (SA), could effectively kill a panel of human cancer cell lines; in some cases the SA could induce apoptosis at a subpicomolar $EC_{50}$. Despite the optimized potency of these SA proteins, some cell lines remained partially or completely resistant.

SUMMARY

The present disclosure is directed to compositions comprising a TRAIL receptor agonist and at least one sensitizing agent, wherein the sensitizing agent is a pharmacological inhibitor of XIAP, BCL-$X_L$, and CDK4 or CDK6.

The present disclosure is also directed to methods of treating cancer in a subject in need thereof comprising administering to the subject a therapeutically effective amount of the compositions disclosed herein. In some aspects, the composition comprises a TRAIL receptor agonist fused to a thermally responsive polypeptide that has a transition temperature (Tt) between about 20° C. and 33° C., and forms a sustained release subcutaneous depot in the subject upon administration.

Other aspects of the invention will become apparent by consideration of the detailed description and accompanying drawings.

BRIEF DESCRIPTION OF THE DRAWINGS

FIG. 1A is a schematic of the function of DRAs. The schematic shows that the DRA is composed of oligomers of the tenth type III fibronectin domains of tenascin engineered to bind death receptor 5 (DR5) with a KD=43 nM for the DRA monomer, linked by flexible glycine-serine linkers $(G_4S)_3$ and expressed recombinantly in E. coli. Monomers and dimers do not induce cell death (top), whereas the hexameric DRA increases apoptotic signaling in sensitive cell lines (bottom). FIG. 1B and FIG. 1C are graphs of cell viability versus concentration of DRA in human CRC cell lines. The responses to DRA treatment are superior to TRAIL in TRAIL-sensitive cell lines HCT116 and Colo205. FIG. 1D is a graph of cell viability in TRAIL-resistant cell line HT29 cells showing cell death induced by DRAs. FIG. 1E is a graph of cell viability demonstrating that RKO cells are resistant to both TRAIL and DRA treatment.

FIG. 2A is the SDS-PAGE of DRA-$His_8$ purified from E. coli periplasmic space. Lanes: #1 Precision Plus Unstained Protein Standards, #2: Flow-through fraction from Ni-NTA agarose resin purification, #3 wash fraction, #4 pure DRA eluate with a MW of ~66 kDa. FIG. 2B is the SDS-PAGE of TRAIL-$His_8$ purified from E. coli cell lysate using Ni-NTA agarose resin purification. Lanes: #1 Precision Plus Unstained Protein Standards, #2: pure TRAIL eluate at about 21 kDa. FIG. 2C is the SDS-PAGE of $ELP_{depot}$-DRA purified from E. coli cell lysate using inverse transition cycling (ITC). The amino acid sequence of $ELP_{depot}$ is $(VPGVG)_{120}$. Lanes: #1 Precision Plus unstained protein standards, #2: Purified $ELP_{depot}$-DRA after 2 rounds of ITC, with a MW of ~110 kDa. FIG. 2D is the SDS-PAGE of $ELP_{soluble}$-DRA purified from E. coli cell lysate by inverse transition cycling (ITC). The amino acid sequence of $ELP_{soluble}$-DRA is $(VPGXG)_{120}$ where X alternates between alanine and glycine. Lanes: #1 Precision Plus unstained protein standards, #2: Purified $ELP_{soluble}$-DRA after 2 rounds of ITC, with a MW of ~110 kDa. FIG. 2E shows the chromatogram from the size exclusion chromatography confirming $ELP_{depot}$-DRA protein purity and absence of large aggregates. The SEC traces are for absorbance at 220 nm (top) and 280 nm (bottom). FIG. 2F shows the MALDI-TOF mass spectrum of purified DRA-$His_8$ shows peaks that correspond to ions arising from the full-length protein with a +1 charge state (m/z=66365) and a +2 charge state (m/z=33185.5). Expected molecular weight is 66,308.8 Da.

FIG. 3A, FIG. 3B, FIG. 3C, FIG. 3D, FIG. 3E, and FIG. 3F show cytotoxicity dose-response curves for TRAIL and DRA in nine human colorectal cancer cell lines and a summary table of the results. Cell lines with an EC50>100 nM were deemed resistant. DRA is 70-1700 times more potent in TRAIL-sensitive cell lines HCT116, HCT15 (FIG. 3B), Colo205, DLD-1 (FIG. 3A), and Lovo (FIG. 3C). DRA induces cytotoxicity in TRAIL-resistant cell line HT29 as well as partially resistant T84 (FIG. 3D). TRAIL-resistant RKO and Colo320HSR (FIG. 3E) are also resistant to DRA. FIG. 3F indicates $EC_{50}$ of each drug for each cell line and the increase in potency of DRA compared to TRAIL. The T/D fold increase is defined as the ($EC_{50}$-TRAIL)/($EC_{50}$-DRA).

FIG. 4 shows a graph of the results from a cell viability assay comparing commercially available recombinant human TRAIL and TRAIL purified in-house in Colo205 cells.

FIG. 7A shows mRNA expression data obtained from CCLE for three DRA resistant and six DRA sensitive CRC cell lines as a heat map created to visualize the data for expression of nine pro-apoptotic (bold italic) and six anti-apoptotic genes (italic) in each cell line. FIG. 7B is a bar graphs showing the percent RKO cells positively stained for Annexin V after treatment with etoposide for 48 h. Annexin V binding to DMSO control treated cells is statistically significantly different from treatment with 25 or 50 μM etoposide. FIG. 7C is a bar graphs showing percent CRC247 cells positively stained for Annexin V after treatment with etoposide for 48 h. Annexin V binding to DMSO control treated cells is statistically significantly different from treatment with 5, 25 or 50 μM etoposide.  p=0.001, * p=0.0001 as analyzed by one-way ANOVA followed by Tukey's post-hoc test.

FIG. 8A includes graphs from genes encoding extrinsic apoptotic pathway proteins (TNFRSF10B, CASP3, CASP7, CASP8) which are expressed at similar levels in TRAIL-sensitive (gray) and TRAIL-resistant human colorectal cancer (CRC) cell lines. FIG. 8B is a graph showing there is no significant difference in mRNA expression levels of genes encoding intrinsic apoptotic proteins (MAP, BCL2, BCL2L1, CFLAR) in TRAIL-sensitive (gray) and TRAIL-resistant CRC cell lines. Corrected p-values of t-tests between TRAIL-resistant and TRAIL-sensitive cell lines were not significant (p>0.05) for all genes shown in FIG. 8A and FIG. 8B. FIG. 8C and FIG. 8D are graphs showing the expression levels of sample genes with very low and very high mRNA expression, respectively, demonstrating the overall expected range in the analyzed cell lines.

FIG. 9A is a schematic overview of loss-of-function CRISPR screen experimental set-up. First, sgRNA and Cas9 expression, packaging, and envelope plasmids were transfected into 293T cells and lentiviral particles were harvested. The RKO cell line was then infected with the pooled lentiviral library and puromycin selection was completed. The transfected cell line was sub-cultured for each desired condition (in duplicate) and treatment continued for 2-3 weeks, after which DNA was extracted from all samples. Constructs were barcoded by PCR and sent for Illumina sequencing. FIG. 9B is a scatter plot showing the results of TRAIL LOF CRISPR screen in RKO cells. FIG. 9C is a scatter plot showing the results of DRA LOF CRISPR screen in RKO cells. Gray box indicates genes with depletion metric scores <0.8. Each dot represents a gene and is plotted on the depletion metric of each of its two replicates (replicate 1 on x axis, replicate 2 on y axis). Red dots indicate common hits between TRAIL and DRA screens. Blue dots indicate hits uniquely generated in the DRA screen. FIG. 9E is a bar graph of flow cytometry data shows increased cytotoxicity (positive Annexin V staining) for combination treatment conditions in RKO cells. A-1155463 (A-11) is a BCL-XL inhibitor. One-way analysis of variance (ANOVA) followed by Bonferroni multiple comparisons test was used to establish significance between A-11/BV6 (dark gray) and A-11/BV6/DRA for both DRA concentrations (light gray). FIG. 9F shows the results of clonogenic 2D growth assay experiments of >7 days in CRC247 cells indicates dramatically slower cell growth upon treatment with DRA in combination with increasing doses of A-1155463 and BV6 each at 0, 50, and 150 nM (left to right) and 0, 3.7, or 7.5 pM DRA (top to bottom). Percent colony area has been graphed for visual purposes below the primary result. For all panels, error bars show standard error of the mean (SEM). **** p<0.0001.

FIG. 16A shows the plates following treatment of RKO cells with DRA in combination with increasing doses of A-1155463 and BV6 at 0, 50, and 150 nM (left to right) and 0, 0.6, or 1.2 pM DRA (top to bottom). Percent colony area has been plotted for visual purposes below the primary result in (FIG. 16B).

FIG. 18A is a schematic showing a hydrophobic ELP was fused to DRA for a depot-forming formulation ($ELP_{depot}$-DRA), and a hydrophilic ELP was fused to DRA as a soluble, non-depot-forming molecular weight matched control ($ELP_{soluble}$-DRA). FIG. 18B is a plot of optical turbidity, measured at 350 nm ($OD_{350}$), demonstrates phase transition of $ELP_{depot}$-DRA at 27.9° C., while $ELP_{soluble}$-DRA remains soluble up to ~0.60° C. FIG. 18C is a plot of cell viability assay data for DRA-sensitive Colo205 cells shows that $ELP_{soluble}$-DRA, $ELP_{depot}$-DRA, and DRA lead to similar in vitro cytotoxicity. FIG. 18D is a schematic of xenografts injection. FIG. 18E and FIG. 18F show are plots showing the results from Colo205 s.c. xenografts injected once on Day 0 with $ELP_{depot}$-DRA, $ELP_{soluble}$-DRA, soluble DRA, TRAIL, or vehicle. All drugs were injected intratumorally. Tumor growth data (FIG. 18E), shown as tumor volume vs. time. Data were analyzed using two-way ANOVA of matched values followed by Fisher's LSD multiple comparisons test to establish significance (p<0.05) of the difference between groups at each day of treatment. Results indicate statistically significant differences in tumor volumes between and including days 9 and 18 for depot-forming $ELP_{depot}$-DRA compared to other groups, including soluble $ELP_{soluble}$-DRA. Kaplan-Meier survival results (FIG. 18F) demonstrate prolonged survival for mice treated with depot-forming $ELP_{depot}$-DRA formulation. Evaluation of survival data with log-rank test suggests significant differences (p, 0.05) between $ELP_{depot}$-DRA and other treatment groups with approximately 16 days increased median survival for the slow release formulation compared to the soluble version.

FIG. 20A shows cell viability data for CRC247 shows efficacy of triple drug treatment with A-1331852 (A in figure legend), BV6 (B in figure legend), and DRA (A+B+DRA) compared to double drug treatments. Data were analyzed using two-way ANOVA of matched values to establish significance (p, 0.05) of the difference between A+B+DRA and DRA. FIG. 20B, FIG. 20C, and FIG. 20D show CRC247 PDX data demonstrating in vivo efficacy of the A+B+$ELP_{depot}$DRA compared to other treatment groups. DRA formulation used in these plots was ELP$_{depot}$-DRA and abbreviated to "DRA" in figure legends of FIGS. 20B-20D. in B-D. FIGS. 20B and 20C show tumor growth inhibition data; mice were treated with A-1331852 (25 mg/kg daily p.o.) and/or BV6 (5 mg/kg q.4.d.), and/or ELP$_{depot}$-DRA (30 mg/kg weekly s.c.). Data were analyzed using two-way ANOVA of matched values followed by Fisher's LSD multiple comparisons test to establish significance (p<0.05) of the difference between groups at each day of treatment. Results indicate statistically significant tumor volumes between and including days 5 and 13 for triple combination of A-1331852+BV6+ELPdepot-DRA compared to every other group. According top values obtained from a two-way ANOVA followed by Fisher's LSD test, the tumor size of the mice in the ELPdepot-DRA+A+B group are statistically significantly different from those of the mice in the ELPdepot-DRA group (p<0.05) from Day 2 to Day 13. FIG. 20D shows Kaplan-Meier survival analysis comparing key treatment groups indicates that median survival increases from 29 to 38 days when BV6 is added to the A-1331852+ELP$_{depot}$-DRA combination. A Gehan-Beslow-Wilcoxon test demonstrated statistically significant difference in survival between all single-drug treatment groups and triple drug combination A-1331852+BV6+ELP$_{depot}$-DRA (p<0.05).

FIG. 22A is a line graph showing doses of 1 µM BV6 and 2 µM A-1331852, chosen as background dose of sensitizers in combination treatments with DRA in vitro were minimally toxic to CRC247s. FIG. 22B is a bar graphs showing the combination of A-1331852 and BV6 at the chosen background doses of each drug is not toxic to CRC247s.

DETAILED DESCRIPTION

Figure 1A:
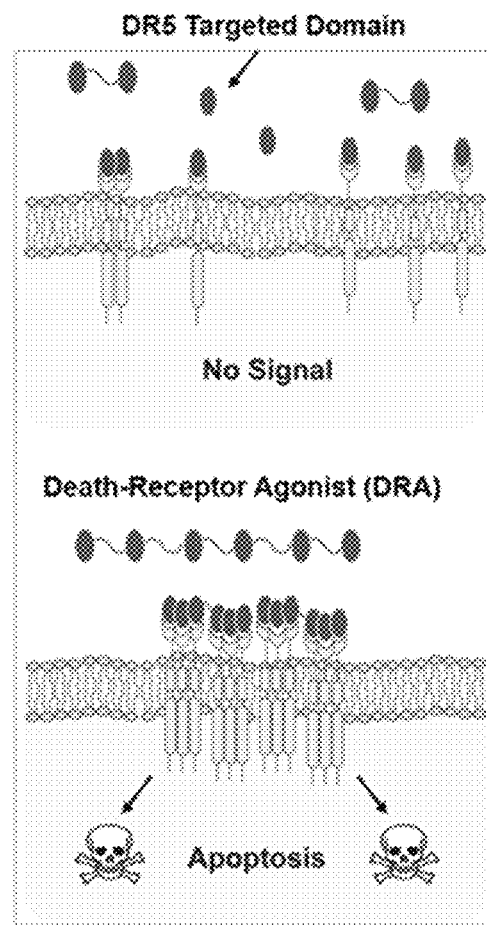
FIG. 1A, FIG. 1B, FIG. 1C, FIG. 1D, and FIG. 1E show that multivalent pro-apoptotic death receptor agonists (DRAs) can induce cell death in TRAIL-sensitive and TRAIL-resistant human colorectal cancer (CRC) cell lines.
Figure 1B:
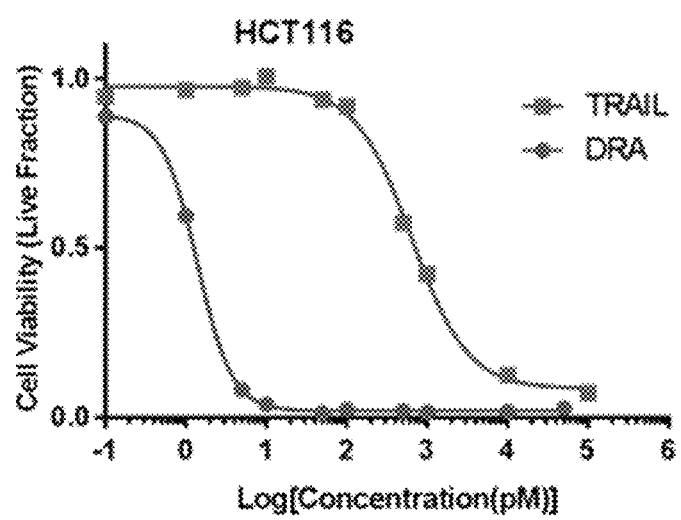

Embodiments of the present disclosure relate generally to the treatment of cancer involving activation of the tumor necrosis factor-related apoptosis inducing ligand receptor (TRAILR) pathway. In particular, the present disclosure provides compositions and methods for the identification of genes conferring TRAIL resistance, and the development of rational drug combinations targeting these genes. The therapeutic drug combinations of the present disclosure function synergistically to sensitize cancer cells to TRAIL-resistant cancers.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "combination" or "drug combination" or "combination therapy" refer to the use of more than one therapeutic agent (e.g., an XIAP inhibitor, a Bcl-xL inhibitor, and TRAIL receptor agonist). These terms do not restrict the order of therapeutic administration to a subject with a disease or disorder (e.g., cancer). In some embodiments, combinations of drugs have synergistic effects on apoptotic activation (i.e., pro-apoptotic synergism). Such synergistic effects can be obtained with combinations of TRAs with one or more targeted sensitizing agent(s), or with a combination of two or more targeted sensitizing agents without TRAs.

"Correlated to" as used herein refers to compared to.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

The term "Fibronectin type III (FnIII) domain" refers to the accepted third of the three types of internal repeats in human fibronectin. This domain is often referred to as a scaffold protein because it contains three CDR-like (complementarity determining region) loops that can be engineered to bind a protein of interest using common molecular biology techniques.

A "pharmacological inhibitor" is inhibition of the activity of a protein or pathway by administration or contact with a drug. The drug may be a small molecule drug, a peptide-based drug, or an antibody-based drug.

A "peptide" or "polypeptide" is a linked sequence of two or more amino acids linked by peptide bonds. The polypeptide can be natural, synthetic, or a modification or combination of natural and synthetic. Domains are portions of a polypeptide or protein that form a compact unit and are typically 15 to 350 amino acids long.

The term "superagonist" (SA) refers to a recombinant multivalent protein consisting of fusions of fibronectin domains that bind and activate TRAILR2. In some embodiments, the term superagonist (SA) and TRAIL receptor agonist (TRA) and death receptor agonist (DRA) are interchangeable.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

The term "Tn3" or "Tn3 scaffold" is an FnIII domain of the sequence SEQ ID NO: 1. The Tn3 domains are versions specifically engineered to bind TRAIL receptor 2.

As used herein, the term "transition temperature" or "Tt" refers to the temperature at which the material changes from one state to another, for example, soluble to insoluble. For example, below the Tt the conjugate may be highly soluble in a liquid form. Upon heating above the transition temperature, for example, the conjugate may aggregate, forming a separate phase, which may be a gel.

The term "TRAIL receptor 2" or "TRAILR2" refers to the TRAIL receptor protein described herein. Upon binding TRAIL or other agonists, TRAILR2 activates apoptosis, or programmed cell death, in tumor cells.

Any "agonist" or "TRAIL receptor agonist" (TRA) or "death receptor agonist" (DRA) referred to herein refers to a protein that activates TRAILR2 in vitro, in situ, and/or in vivo.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The term "Bcl-xL inhibitor," or "Bi," includes any compound that disrupts Bcl-xL activity or production. In some embodiments, a Bcl-xL inhibitor results in increased apoptosis.

The term "CDK4/6 inhibitor," or "Ci," includes any compound that disrupts activity/production/function of cyclin dependent kinase (CDK) 4 or 6 or both or affects the activation of the cyclin-CDK4/6 signaling axis. In some embodiments, CDK4/6 inhibitor results in increased apoptosis.

The term "XIAP inhibitor," or "Xi," includes any compound that disrupts activity/production of XIAP. In some embodiments, XIAP inhibitor results in increased apoptosis.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Compositions

Provided herein are compositions comprising a TRAIL receptor agonist and at least one sensitizing agent, wherein the sensitizing agent is a pharmacological inhibitor of XIAP, BCL-$X_L$, and CDK4 or CDK6.

i. Trail Receptor Agonist

The composition may comprise any TRAIL receptor agonist. In some embodiments, TRAIL receptor agonist causes higher cytotoxicity compared to TRAIL.

The TRAIL receptor agonist may be multimeric. The TRAIL receptor agonist may comprise a plurality of type III fibronectin domains connected to one another with flexible glycine-serine linkers.

In some embodiments, the TRAIL receptor agonist comprises 2-8 type III fibronectin domains. In certain embodiments, the TRAIL receptor agonist comprises 6 type III fibronectin domains. In some embodiments, the type III fibronectin domains are derived from human tenasin.

In some embodiments, at least one of the plurality of fibronectin domains comprise SEQ ID NO: 1. In some embodiments, all of the plurality of fibronectin domains comprise SEQ ID NO: 1. In some embodiments, the TRAIL receptor agonist comprises 6 type III fibronectin domains of SEQ ID NO: 1.

SEQ ID NO: 1 is GAIEVKDVTDTTALITWAKPWVDPPPLWGCELTYGIKDVPGDRTTIDLQQKHTAYSIGNLKPDT EYEVSLICFDPYGMRSKPAKETFTT.

In some embodiments, the flexible glycine-serine linkers comprise SEQ ID NO: 2.

SEQ ID NO: 2 is GGGGSGGGGSGGGGS.

The TRAIL receptor agonist may be fused with a thermally responsive polypeptide. Thermally responsive peptides may have phase transition behavior such that at certain temperatures they undergo a phase transition, for example for a soluble form to a gel-like viscous form.

In some embodiments, the thermally responsive polypeptide is an elastin-like polypeptide (ELP). Elastin like polypeptides may comprise a pentapeptide repeat sequence $(VPGXG)_n$ (SEQ ID NO:3), wherein X is any amino acid except proline and n is an integer greater than or equal to 1. In some embodiments n is between 60 and 180. In some embodiments, n is 60, 120 or 180. In some embodiments, X is valine.

The ELP may have phase transition behavior, wherein the polypeptides becomes insoluble at a transition temperature ($T_t$). Phase transition may refer to the aggregation, which may occur sharply and in some instances reversibly at or above the transition temperature. The $T_t$ can be adjusted by varying the amino acid sequence of the elastin-like polypeptide, by varying the length of the polypeptide, or a combination thereof.

The transition temperature may be between 20° C. and 33° C. The transition temperature may be 20° C., 21° C., 22° C., 23° C., 24° C., 25° C., 26° C., 27° C., 28° C., 29° C., 30° C., 31° C., 32° C., and 33° C. In certain embodiments, the transition temperature is 25° C.

Phase transition behavior may also enable purification of the conjugate using inverse transition cycling, thereby eliminating the need for chromatography. "Inverse transition cycling" refers to a protein purification method for polypeptides having phase transition behavior, and the method may involve the use of the conjugate's reversible phase transition behavior to cycle the solution through soluble and insoluble phases, thereby removing contaminants and eliminating the need for chromatography.

ii. Sensitizing Agents

The present disclosure provides drug combinations that enhance the cytotoxicity of TRAIL receptor agonists. Combinations include targeted sensitizing agents that improve the efficacy of protein agonists, and in some cases, exhibit synergistic efficacy. These targeted agents may be inhibitors of kinases and/or inhibitors of anti-apoptotic proteins.

The at least one sensitizing agent may be an inhibitor of anti-apoptotic proteins (e.g., X-linked inhibitor of apoptosis protein, XIAP, cellular inhibitor of apoptosis protein, B-cell lymphoma-extra-large, Bcl-xL) and/or an inhibitor of kinase proteins (e.g., cyclin dependent kinase 4 and 6, CDK4/6).

In some embodiments, the sensitizing agent comprises an inhibitor of XIAP. XIAP inhibitors include, for example, Embelin, GDC-0152, Birinapant, LCL-161, and BV-6. In some embodiments, the sensitizing agent comprises BV-6.

In some embodiments, the sensitizing agent comprises an inhibitor of BCL-XL. BCL-XL inhibitors include, for example, BH31-1, WEHI-539, A-1155463 and A-1331852. In some embodiments, the sensitizing agent comprises WEHI-539, A-1155463 and/or A-1331852.

In some embodiments, the sensitizing agent comprises an inhibitor of CDK4/6. CDK4/6 inhibitors include, for example, abemaciclib, palbociclib, and ribociclib. In some embodiments, the sensitizing agent comprises palbociclib.

The composition may comprise at least one sensitizing agent, at least two sensitizing agents, or at least 3 sensitizing agent. In some embodiments, the composition comprises BV-6 and palbociclib. In some embodiments, the composition comprises WEHI-539 and palbociclib. In some embodiments, the composition comprises A-1331852 and palbociclib. In some embodiments, the composition comprises A-1155463 and palbociclib. In some embodiments, the composition comprises BV-6 and WEHI-539. In some embodiments, the composition comprises BV-6 and A-1331852. In some embodiments, the composition comprises BV-6 and A-1155463.

3. Methods of Use

The present disclosure also provides methods of treating cancer. The method comprises administering to a subject in need thereof a therapeutically effective amount of the composition as detailed herein to the subject.

The compositions as detailed herein may be used to treat any cancer type or subtype. The cancer may be a carcinoma, sarcoma, lymphoma, leukemia, melanoma, mesothelioma, multiple myeloma, or seminoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus. In some embodiments the cancer is colon cancer.

In some embodiments, the cancer is a TRAIL-resistant cancer. Although many types of cancers are sensitive to TRAIL-induced apoptosis, substantial numbers of cancer cells are resistant to TRAIL, especially some highly malignant tumors such as pancreatic cancer, melanoma, and neuroblastoma. In certain embodiments, the cancer is a FRAIL-resistant colon cancer.

In some embodiments, the cancer is a solid tumor. Examples of cancers that are solid tumors include, but are not limited to, pancreatic, bladder, non-small cell lung cancer (NSCLC), breast and ovarian cancers. In some embodiments, the cancer is a TRAIL-resistant solid tumor.

Administration may cause a variety of positive outcomes. The composition may cause reduction of tumor growth. The composition may cause increased survival of the subject. In some embodiments, the composition may cause better reduction of tumor growth and/or increased survival when compared to treatment with a monotherapy of a TRAIL receptor agonist. In some embodiments, the composition may cause better reduction of tumor growth and/or increased survival when compared to treatment with a monotherapy of a sensitizing agent.

The method may utilize a TRAIL receptor agonist fused with a thermally responsive polypeptide. In some embodiments, the thermally responsive polypeptide has a transition temperature (Tt) between about 20° C. and 33° C. In some embodiments, the thermally responsive polypeptide has a transition temperature (Tt) of about 25° C. When administered, the TRAIL receptor agonist fused with a thermally responsive polypeptide may form a sustained release subcutaneous depot in the subject upon administration. In some embodiments, the depot is gel-like. The gel-like depot forms due to the transition temperature being lower than body temperature, such that at room temperature the TRAIL receptor agonist fused with a thermally responsive polypeptide is soluble and liquid but at body temperature TRAIL receptor agonist fused with a thermally responsive polypeptide forms a gel.

The present disclosure also provides highly potent and specific pro-apoptotic drug combinations that are highly efficacious in a broad panel of human colorectal cancer cells. In some cases, compounds with similar structures and/or functions as the targeted sensitizing agents were not able to elicit a potent therapeutic response. Thus, the drug combinations of the present disclosure exhibit precise efficacy and potent synergy in combination with TRA. Resistance of colorectal cancer cells to highly potent TRAs has been addressed through combination with small molecule inhibitors that target proteins associated with TRA resistance.

4. Administration and Dosing

The disclosed compositions may be incorporated into pharmaceutical compositions suitable for administration to a subject (such as a patient, which may be a human or non-human) well known to those skilled in the pharmaceutical art. The pharmaceutical composition may be prepared for administration to a subject. Such pharmaceutical compositions can be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. The route by which the composition is administered and the form of the composition will dictate the type of carrier to be used.

The compositions disclosed herein can be administered therapeutically. In therapeutic applications, the composition is administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The compositions disclosed herein can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997). One skilled in the art would know that the choice of a pharmaceutically acceptable carrier, including a physiologically acceptable compound, depends, for example, on the route of administration.

The compositions disclosed herein may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies.

Dosage amount(s) and interval(s) may be adjusted individually to provide levels of the composition which are sufficient to maintain the modulating effects, or minimal effective concentration (MEC). The MEC will vary but can be estimated from in vivo and/or in vitro data. Dosages necessary to achieve the MEC will depend on individual characteristics and route of administration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the compositions may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. The second therapy may be a combination of a second therapeutic agent or may be a second therapy not connected to administration of another agent. Such second therapies include, but are not limited to, surgery, immunotherapy, radiotherapy, or a second chemotherapeutic agent.

5. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Materials and Methods

Xenograft tumor studies. In the xenograft tumor studies, mice were randomized to groups according to tumor volume prior to treatment. The number of mice per group is specified in the figure legends. Tumor sizes were measured by caliper, and the primary endpoint was survival. All procedures were performed as approved by the Institutional Animal Care and Use Committee at Duke University. The investigators were not blinded during the study.

Statistical analysis. Results were expressed as means±SEM and analyzed by one-way ANOVA with Tukey's post-hoc test for grouped analyses. The exception is in vivo tumor data analyses, in which matched values were analyzed by two-way ANOVA with Fisher's LSD multiple comparisons test to establish significance (P<0.05) of the difference between groups on each day of treatment. Survival times of treatment groups were analyzed and compared using the Mantel-Cox log-rank test. GraphPad Prism 7 Software was used for all statistical analysis and generation of Kaplan-Meier survival plots. Statistical significance of differences was set at *P<0.05, P<0.01, *P<0.001, and ****P<0.0001.

In silico gene expression analysis. The mRNA gene expression data were obtained from the Cancer Cell Line Encyclopedia. Gene-centric robust multi-array average (RMA)-normalized expression values of the genes of interest were visualized in a heatmap, where lower expression is represented in blue and higher expression is represented in red. Additionally, scatter plots were generated to show individual expression level of each gene in each cell line more clearly.

Synthesis and Assembly of Genes:

The DNA encoding the monomer of the type III fibronectin domain from tenascin (Tn3) in the death receptor agonist (DRA) encoded the following amino acid sequence (GAIEVKDVTDTTALITWAKPWVDPPPLWGCELTY-GIKDVPGDRTTIDLQQKHTAYSIGNLKPD TEYEVSL-ICFDPYGMRSKPAKETFTT) (SEQ ID NO: 1). The *E. coli* codon-optimized gene was purchased as a "G-block" from Integrated DNA Technologies (IDT). The gene was purchased with a $(Gly_4Ser)_3$ (SEQ ID NO: 2) linker at the C-terminus and designed with restriction sites compatible with recursive directional (RDL) ligation for seamless cloning of oligomeric genes. The amplified PCR product was purified using a Qiagen PCR cleanup kit and digested with BseRI for insertion into a BseRI/CIP digested pET-24(+) vector modified for RDL. The insert and vector were agarose gel-purified and ligated with QuickLigase to clone the single unit construct. This was followed by digestion of the single unit construct (Tn3 in pET24(+)) with BseRI/CIP and ligation with BseRI-digested insert (Tn3 monomer) to clone 2, 4, and 6 Tn3 repeats in the pET-24(+) vector (Novagen; Madison, Wis.). EB5α cells (EdgeBio) were used for cloning steps. All enzymes were purchased from New England Biolabs.

The gene for the depot-forming ELP ($ELP_{depot}$) that encodes the amino acid sequence $(VPGVG)_{120}$ (SEQ ID NO: 3) and soluble ELP ($ELP_{soluble}$) that encodes the amino acid sequence $(VPG\underline{A/G}G)_{120}$ (SEQ ID NO: 3) was recombinantly fused to the hexameric Tn3 fusions using recursive directional ligation (RDL). The recursive directional ligation method for this particular vector called for digestion of the oligomerized Tn3 in modified pET24(+) with BseRI and BglI and digestion of ELP in pET24(+) with AcuI and BglI The digested fragments of DNA were separated using agarose gel electrophoresis, and the DNA bands of the appropriate molecular weights were excised and gel-purified using the QIAquick Gel Extraction kit (Qiagen). The purified fragments were ligated using QuickLigase (New England Biolabs) and successful clones were identified by DNA sequencing analysis.

The hexamer $ELP_{depot}$DRA fusion constructs were expressed in SHuffle T7 Express cells in 2XYT media in 1 L shake flasks (New England Biolabs). 50 mL overnight cultures were used to inoculate 1 L Erlenmeyer flasks in a shaker incubator (GYROMAX 747 orbital incubator shaker, Amerex Instruments, Inc.) and cells were grown for 4-5 h at 30° C., then induced with 1 mM sterile IPTG and incubated at 180 rpm at 25° C. for another 6-12 h. Cells were pelleted, resuspended in 50 mM Tris pH 8, sonicated, and centrifuged at 15,000 rpm at 4° C. for 15 min to separate cell debris from the soluble fraction. Proteins were purified from the soluble fraction of the cell lysate using inverse transition cycling (ITC), a method that exploits the LCST phase transition of ELP fusions, and involves repeated cycles of protein aggregation and solubilization. Specifically, the "hot spin" of ITC was performed by addition of <2 M ammonium sulfate until the solution became turbid and the salt was fully dissolved and centrifuged at 14000 rpm at 35° C. for 20 min to pellet the protein. The phase transitioned protein pellet was then resuspended in 20 mM Tris, 300 mM Arginine at pH 7 and placed in a rotator at 4° C. The "cold spin" of ITC was performed by centrifuging the protein at 4° C., 14000 rpm and preserving the supernatant, which contained the $ELP_{depot}$-DRA fusion. The hot spin/cold spin process was repeated 2 times before further purification by size exclusion chromatography on a Superdex HiLoad 26 60/200 column in PBS on an AKTA chromatography system (GE Healthcare Life Sciences). Pure eluate then underwent buffer exchange into 20 mM Tris 300 mM Arginine pH 7 using 10 kDa Amicon Ultra centrifugal filters (EMD Millipore). All purified proteins were analyzed by SDS-PAGE on Bio-Rad Mini-PROTEAN TGX Tris-HCl Stain-Free gels for correct molecular weight bands.

For DRA expression without fusion to ELP, the DNA sequence encoding a periplasmic secretion signal, oppA "MTNITKRSLVAAGVLAALMAGNVALA" (SEQ ID NO: 4) was appended at the 5' terminus of the hexameric DRA gene by the previously discussed RDL method, and DNA encoding a His tag was appended at the 3' end of the DRA gene to create a gene that encodes the following construct, oppA-DRA-His$_8$. This construct was then expressed in BL21(DE3) cells: 50 mL overnight cultures were used to inoculate 1 L shake flasks and cells were grown at 37° C. for 4-5 h, then induced with 1 mM sterile IPTG and incubated at 37° C. in a shaker incubator (GYROMAX 747 orbital incubator shaker, Amerex Instruments, Inc.) for another 4-6 h. Cells were then pelleted and resuspended in 100 mL ice-cold 10 mM Tris, 1 mM EDTA, pH 8 buffer and placed on a rotator at 4° C. for 1-2 h to complete protein extraction from periplasmic space. The periplasm extraction samples were then centrifuged at 14000 rpm for 15 min at 4° C. to pellet cell debris. Proteins in solution were precipitated with ammonium sulfate (60% weight/volume) and centrifuged for 15 min to pellet the precipitated protein. The protein pellet was then placed on ice and resuspended in ice-cold PBS. Immobilized metal affinity chromatography (IMAC) on a Nickel-NTA agarose resin (Thermo Fisher Scientific) was then used to purify the His-tagged DRA from other periplasmic proteins by following the manufacturer's protocol. Pure eluate then underwent buffer exchange into 20 mM Tris, 300 mM Arginine, pH 7 using 10 kDa Amicon Ultra centrifugal filters (EMD Millipore).

TRAIL-His$_8$ (TRAIL amino acids 114-281) was purchased as a G-block from IDT, cloned into pET-24(+) plasmid system (Novagen), and grown in BL21(DE3) cells (EdgeBio). 50 mL overnight cultures were used to inoculate 1 L shake flasks and cells were grown at 25° C. for 4-5 h, then induced with 1 mM sterile IPTG and incubated at 16° C. in a shaker incubator (GYROMAX 747 orbital incubator shaker, Amerex Instruments, Inc.) overnight. Cells were pelleted, resuspended in 20 mM Tris, 100 µM zinc sulfate, 10 mM calcium chloride, 10 mM DTT, pH 7.4, sonicated, and centrifuged at 4° C. at 15000 rpm for 15 min to separate cell debris from the soluble fraction. The His-tagged DRA was purified from other periplasmic proteins protein on a Nickel-NTA agarose resin by IMAC by following the manufacturer's protocol, Thermo Fisher Scientific). Pure eluate then underwent buffer exchange into 20 mM Tris, 100 µM zinc sulfate, 10 mM calcium chloride, 10 mM DTT pH 7.4. All chemicals were purchased from Sigma Aldrich. The EC50 of in-house TRAIL was within an order of magnitude of commercial TRAIL.

All proteins used for in vivo studies were endotoxin purified using Pall Mustang E Membrane sterile/endotoxin filters and tested using the GenScript ToxinSensor™ Single Test Kit endotoxin test to ensure levels below the FDA recommended limit of 0.25 EU/mL.

Optical turbidity. To determine the transition temperature ($T_t$) of the ELP fusion proteins, the optical turbidity at 350 nm of a 25 µM solution of the ELP fusion proteins was measured at a thermal ramp rate of 1° C./minute between 4 and 60° C. on a temperature-controlled UV-vis spectrophotometer (Cary 300 UV-Vis, Agilent Technologies). The LCST phase transition is indicated by the sudden increase in optical turbidity, and the inflection point of the $OD_{350}$ v. temperature curve is used to calculate the $T_t$.

MALDI/TOF mass spectrometry. MALDI-TOF mass spectrometry was performed for the DRA-His$_8$ protein using an Applied Biosystems Voyager-DE Pro system with a nitrogen laser, and mass spectra were obtained using α-Cyano-4-hydroxycinnamic acid matrix in a 20:1 (v/v) ratio with the analyte.

Cell Lines and Reagents:

All cell lines were grown at 37° C. in 5% $CO_2$. Colo205 were cultured in RPMI (10% FBS, HEPES, pyruvate, 1% Pen/Strep (P/S)). HCT116 and HT29 were cultured in McCoy's (10% FBS, 1% Pen/Strep). RKO were cultured in MEM Earle's (10% FBS, pyruvate, NEAA, 1% P/S). Lovo were cultured in F-12K (10% FBS, 1% P/S). T84 were cultured in 50/50 mix of HAM's F-12 and DMEM (2.5 mM L-glutamine, 5% FBS, 1% P/S). Colo320HSR, DLD-1, HCT-15, and patient-derived cell lines CRC247, CRC12x, CRC119 were cultured in RPMI (10% FBS, 1% pen/strep). All cell lines were purchased within 6 months from Duke CCF or ATCC and patient-derived lines were obtained from David Hsu (Duke University) and passaged less than 10 times. All cell lines were authenticated using Promega PowerPlex 18D kit for short tandem repeat (STR) analysis or were purchased within 6 months from Duke CCF. All cell lines were tested for mycoplasma by Duke CCF. FBS: fetal bovine serum (GIBCO); P/S: penicillin/streptomycin (Thermo Fisher). Media was purchased from GIBCO or Sigma Aldrich.

In Vitro Cell Viability Testing)

For single-agent cytotoxicity evaluation, DRA and ELP-DRA fusion proteins were tested in vitro using a colorimetric formazan assay (MTT) as follows. The cells were plates in 96 well plates at a density of 2,000-10,000 cells/well in 90 µL of complete media (RPMI 1640+10% FBS) and incubated for 1-18 h at 37° C. with 5% $CO_2$. The cells were then treated with 10 µL additional media containing a serial dilution of the drug(s) of interest. All treatments were done in triplicate. After 18-20 h, the Promega CellTiter 96 Aqueous One Solution Reagent G3581 kit was used according to manufacturer's instructions to assay the number of viable cells. The inhibition of cell viability was determined using measurements of the absorbance at 490 nm, which is the absorbance maximum of the formazan product. The dose-response curves were generated by plotting inhibition as a function of compound concentration. The dose-response curve was approximated from the scatter plot using a four-parameter logistic model calculation, and $EC_{50}$ was calculated as the concentration of drug required to kill 50% of the cells.

For combination treatments, the cell viability assays were carried out as follows: colorectal cancer cells were plated in white 96 well plates at a density of 2,000 cells/well in 90 µL of complete media (RPMI 1640+10% FBS) and incubated overnight at 37° C. with 5% $CO_2$. Drugs used to enhance the sensitivity of cells to the death receptor agonists (DRAs) are referred to as "sensitizing drugs" or "sensitizing agents." Sensitizing drugs were dosed at a single concentration, or "background dose", which was chosen to below the GI50 in each cell line. The cells were treated with 10 µL media containing the serial dilution of death receptor agonist and a background dose of sensitizing drug(s). All treatments were done in triplicate. After 72 h, the Promega Cell Titer Glo reagent was used according to manufacturer's instructions to assay the number of viable cells. The cell viability was determined using measurements of luminescence using a Victor$^3$ plate reader (Perkin Elmer). The dose response curves were generated by plotting percent viable cells as a function of DRA concentration. The dose-response curve was approximated from the scatter plot using a four-parameter logistic model calculation, and $EC_{50}$ was calculated as the concentration of DRA required to kill 50% of the cells.

Lentiviral production and titration of CRISPR/Cas9 loss-of-function library. Lentivirus were produced from HEK293T cells, which were grown to 50% confluence in 6 cm plates and transfected using Fugene6 (Promega), 5.6 mg of psPAX2, 0.625 mg of pVSVg, and 6.25 mg of library plasmid. After 30 min of incubation at room temperature, the transfection mixture was added to the cells and incubated overnight at 37° C. The next day, harvest media was added (DMEM, 30% FBS). After 24 h and 48 h collection points, harvested virus was passed through a 0.45 μm filter (EMD Millipore). Viral titers and transductions were performed as previously described (C. A. Martz, et al. *Sci Signal* 7, ra121 (2014)). Thus, a pooled library of viral vectors encoding LOF sgRNA inserts that targeted a panel of 378 druggable genes and signaling pathways was obtained.

CRISPR/Cas9 loss-of-function screen. To identify genetic drivers of CRC resistance to DRAs, a CRISPR/Cas9-based loss-of-function (LOF) screen was completed. A library of viral vectors encoding LOF sgRNA inserts were cloned into a lentiviral expression vector encoding Cas9, packaged with a psPAX2 plasmid, and pseudotyped with VSV-G. Once the pooled lentiviral library was produced by transfection of 293T cells, titered, and used to infect DRA-resistant RKO cancer cells. RKO cells were seeded at 500,000 cells per well in 6 well plates, incubated overnight, and transduced at a multiplicity of infection of 0.3 the next day. After puromycin selection, a sample was taken to verify representation of the various knockout genes.

The transduced population was maintained under puromycin selection for one week, after which the library of cells was then exposed to vehicle, TRAIL, or the DRA (each treatment condition in duplicate) for two weeks. Cell samples were obtained, DNA was extracted (DNeasy Blood & Tissue Kit; QIAGEN), sgRNA barcodes were isolated, prepared for sequencing. The samples were sequenced by next-generation Illumina sequencing (Hudson Alpha), and the raw data was processed to identify "hits" that sensitized RKOs to each treatment, as evidenced by their depletion in drug versus vehicle treatment conditions. The fractional representation (FR) for a given guide in the final condition after vehicle treatment was compared to its FR final condition after TRAIL or DRA treatment. The depletion level of each sgRNA barcode (drug versus vehicle conditions) was calculated as the FR from treated population normalized to the FR from vehicle control (both at final timepoint). Depleted barcodes represent sensitizer genes, as they were specifically depleted in the drug-treated cell populations. Depletion comparisons were used to generate a scoring metric called the "3 score" which represents the average of the three most depleted sgRNAs for a particular gene. The genes were ranked by their 3 scores; top hits are those that sensitized the cells to TRA treatment when knocked out by the CRISPR/Cas9 machinery. Data are presented as the depletion metric mean of the 3 score per gene in the library. "Hits" are genes with a low 3 score, and examples of the genes representing top hits are denoted in Table 1. All data extractions and calculations were coded and completed using R. The hits were subsequently filtered to retain genes that encoded proteins for which specific inhibitors are commercially available.

Flow Cytometry for Annexin-V Apoptosis Quantification. Cells were seeded in six-well plates overnight. The next day, cells were treated with the indicated amount of drug(s) or vehicle control (DMSO). Incubation time was 15 h for etoposide or 48 h for DRA alone, or DRA with sensitizers. To prepare samples for flow cytometry, each well of cells was washed twice with ice-cold PBS and resuspended in 1× annexin V binding buffer (10 mM HEPES, 140 mM NaCl, 2.5 mM $CaCl_2$, pH 7.4) BD Biosciences). Allophycocyanin (APC)-conjugated Annexin V was used to measure surface exposure of phosphatidylserine and 7-aminoactinomycin D (7-AAD) was used as a viability probe (BD Biosciences). Cell samples were analyzed at 20,000 counts/sample using BD FACSVantage SE.

2D Clonogenic Growth Assay. Cells were seeded in 6-well plates at 500 cells per well. The next day, cells were drugged at the indicated doses, and drug media was replaced every 3-4 days. Approximately 1 week after treatment, plates were rinsed with PBS and fixed and stained with 0.5% (wt./v) crystal violet in 6.0% (v/v) glutaraldehyde solution (Thermo Fisher Scientific) for 20 min at room temperature. Plates were rinsed in $diH_2O$, dried overnight, and photographed the following day. Percent colony area covered by crystal violet was quantified using the ImageJ Software colony area plugin.

Immunoblotting. Cells were seeded at 500,000 cells per 10 cm dish and treated the next day. After treatment for 6 and 16 h, cells were scraped off of wells in cold PBS, centrifuged at 5,000 rpm for 3 min at 4° C., separated from supernatant, washed with PBS once, and frozen at −80° C., then lysed with cold RIPA buffer (20 mM Tris-HCl pH 8.0, 137 mM NaCl, 10% glycerol, 1% NP-40, 0.1% SDS, 0.5% Nadeoxycholate, 2 EDTA pH 8.0) supplemented with protease and phosphatase inhibitors (Roche protease inhibitor cocktail; Phosphatase Inhibitor Cocktail I and Phosphatase Inhibitor Cocktail II from Sigma-Aldrich) and centrifuged at 13,300 rpm at 4° C., for 10 min. Protein concentration in supernatant lysates were determined using the Bradford assay (Bio-Rad). Proteins from each lysate (10 μg) were resolved on SDS-PAGE (NuPAGE 4-12%), transferred to PVDF membranes, blocked with 5% milk in TBS+0.1% Tween, and probed with primary antibodies in 5% BSA overnight at 4° C. Primary antibodies (1:1,000-1:2,000 dilution) recognized BCL-XL (CST #2764), BIM (CST #2933), BID (CST #2002), Caspase 3, 8, 9, and β-actin.

Pilot toxicity study of Palbociclib and A-1331852 in nude mice. A small pilot study was conducted in nude mice to evaluate toxicity of the double sensitizer A-1331852 (A-13) and Palbociclib combinations at a range of doses. A-13 is an oral drug, while Palbociclib can be administered orally or intraperitoneally. To avoid potential trauma associated with multiple daily dosing of these drugs, we administered Palbociclib intraperitoneally (i.p.) daily and A-13 dosed orally daily. A daily oral dose of 25 mg/kg was chosen for A-13, as this dose ensures in vivo activity according to known data. Daily administration of A-13 at this dosage did not affect body weight or cause visible signs of toxicity. Palbociclib dosing was first tested at 50 mg/kg i.p. in combination with A-13 dosed orally daily at 25 mg/kg. Unfortunately, this combined dose of Palbociclib and A-13 caused visible toxicity in the mice, resulting in lowered body temperature, reduced mobility, closed eyes, and/or sudden death. Thus, a lower doses of Palbociclib (25 mg/kg and 12.5 mg/kg) were tested in combination with 25 mg/kg A-13 (FIG. S11). However, these doses were still too toxic, as mice continued to lose weight each day (FIG. S11). Within one week, mice lost more than 15% of their body weight; the 25 mg/kg and 12.5 mg/kg doses were therefore too toxic for drug combination studies. A lower 6.25 mg/kg dosage of Palbociclib was also tested in combination with A-13 at 25 mg/kg dosed orally daily, and an introductory test in which 30 mg/kg ELP-DRA was added to this combination treatment caused rapid deterioration in body condition over the course of 2 weeks. Change in dosing frequency was also considered, but the half-life of Palbociclib is only a few hours, making this option infeasible.

Xenograft tumor studies. All tumor studies were carried out in 5-7 weeks old, athymic nude/nude female mice (Jackson Labs), and treatment commenced when tumor size reached 100-120 mm$^3$ (as measured by digital caliper and calculated as LxWx0.5). Colo205 engraftment was performed by subcutaneous injection of 1 million cells in the right flank. Colo205 xenografted mice were treated with one single intratumoral or subcutaneous (contralateral flank) injection of the ELP$_{depot}$-DRA formulation or ELP$_{soluble}$-DRA or DRA or TRAIL on Day 0. DRA fusions and TRAIL were administered at the molar equivalent DRA dose of 30 mg/kg. CRC247 patient-derived cells were engrafted subcutaneously at 3 million cells per mouse. On Day 0, treatment commenced with daily oral gavage for A-1331852 in previously described vehicle, twice weekly i.p. injection of BV6 in sterile saline, and/or weekly subcutaneous injection of ELP$_{depot}$-DRA in the contralateral flank. The ELP$_{depot}$-DRA formulation for in vivo injection comprised of a 1:1 molar ratio of ELPdepot:ELP$_{depot}$-DRA to promote depot formation. All mice were monitored daily to ensure that weight loss did not occur beyond 15%; mice were also evaluated for general body condition and mobility. Doses were chosen based on a small pilot study in which drug combinations were administered and mice were monitored for visible distress and unacceptable (>15%) weight loss.

Example 2

TRAIL Receptor Agonists Induce Apoptosis in Human Colorectal Cancer Cell Lines

A hexavalent TRAIL receptor agonist (death receptor agonist, DRA) protein was selected to maximize receptor engagement and potency. The DRA is a hexameric protein composed of oligomers of the tenth type III fibronectin domains (SEQ ID NO: 1) of tenascin (Tn3) that are engineered to bind TRAIL Receptor 2 (TRAILR2, or death receptor 5 DR5), linked by flexible glycine-serine linkers (SEQ ID NO: 2) and expressed recombinantly in *E. coli*. The DRA induces apoptosis in tumor cells upon binding to its target, death receptor 5 (DR5). Interestingly, monomer and dimer oligomers of the Tn3 domain did not induce apoptosis, but the hexavalent DRA construct was extremely cytotoxic in sensitive cell lines, likely due to the enhanced signaling strength owed to higher order receptor crosslinking (FIG. 1A). A clinically relevant target receptor on the surface of cancer cells, DR5 is significantly upregulated in stage II and III colorectal cancer (CRC), but without prognostic significance. Although human CRC cells express detectable levels of DR5, expression levels do not correlate with sensitivity to DR5 agonists.

Figure 1C:
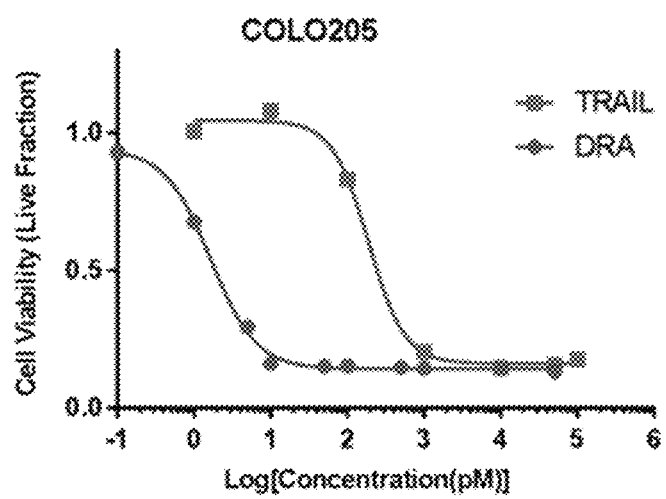
Figure 1D:
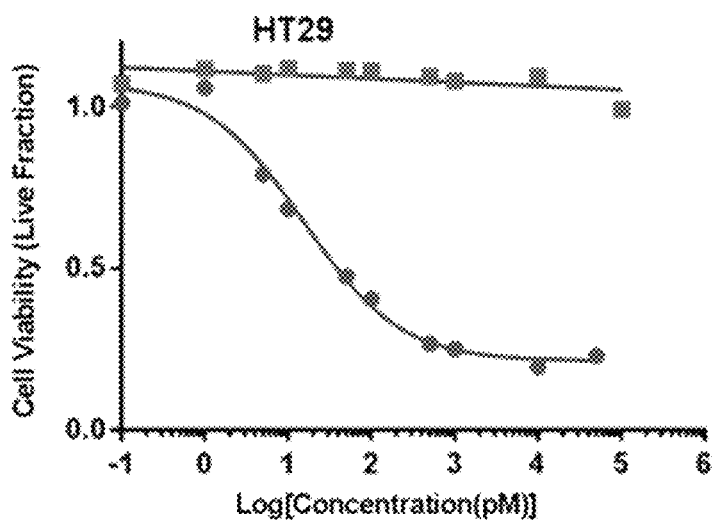
Figure 1E:
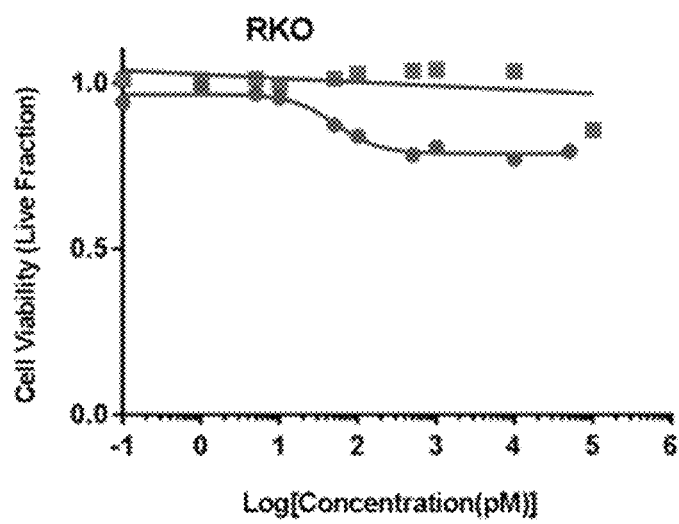
Figure 2A:
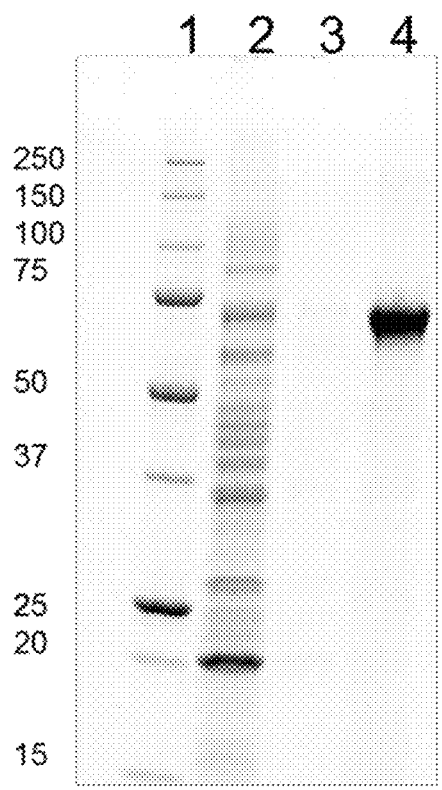
FIG. 2A, FIG. 2B, FIG. 2C, FIG. 2D, FIG. 2E, and FIG. 2F shows the protein characterization of DRAs.
Figure 2B:
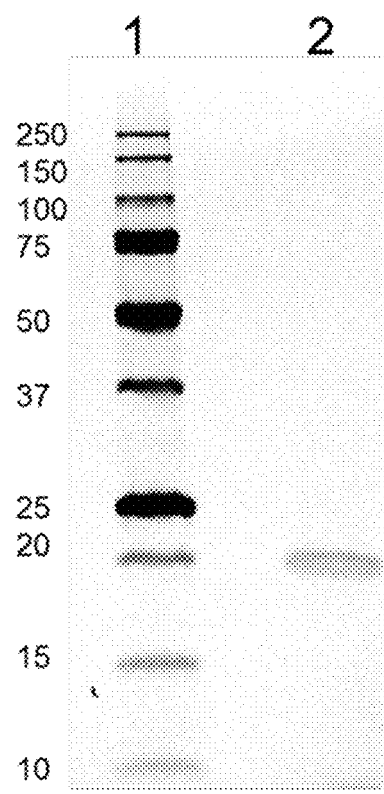
Figure 2C:
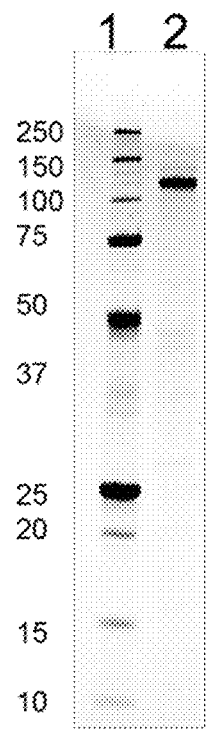
Figure 2D:
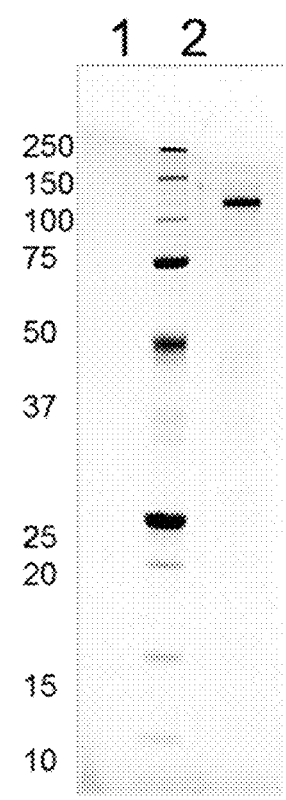
Figure 2E:
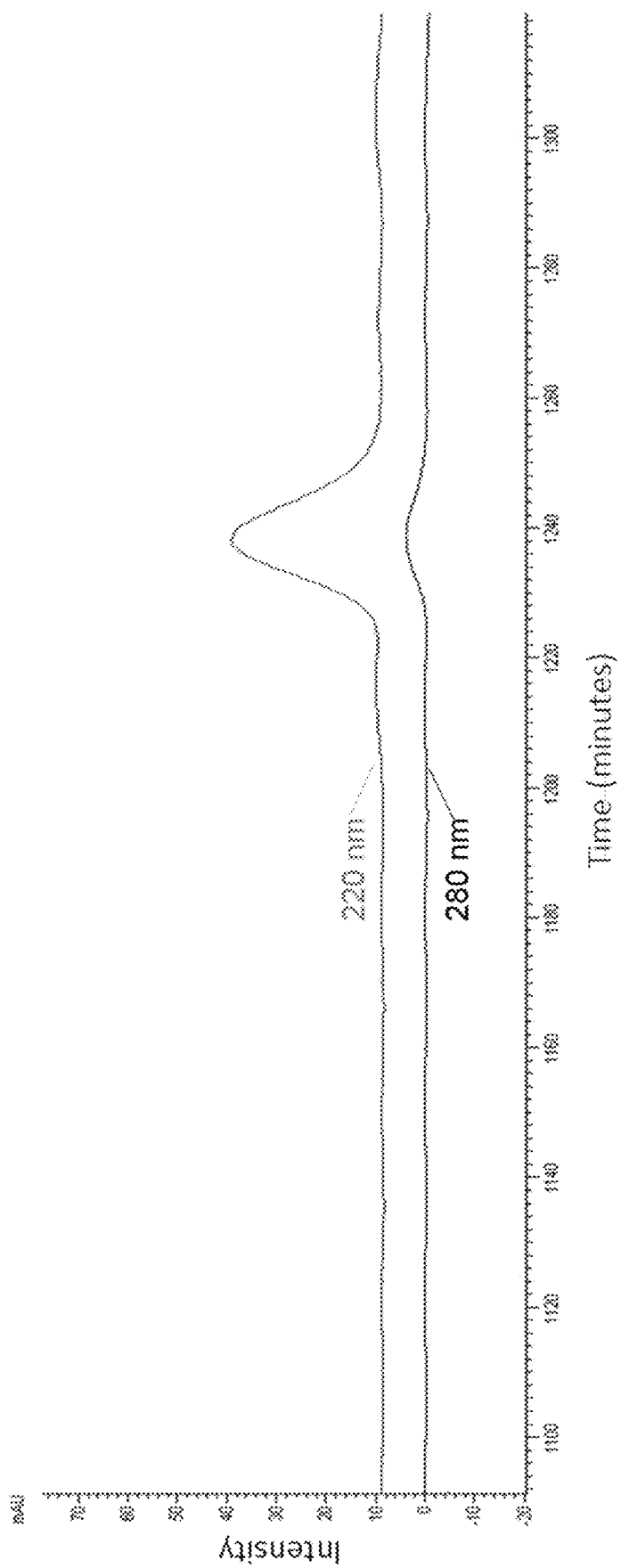
Figure 2F:
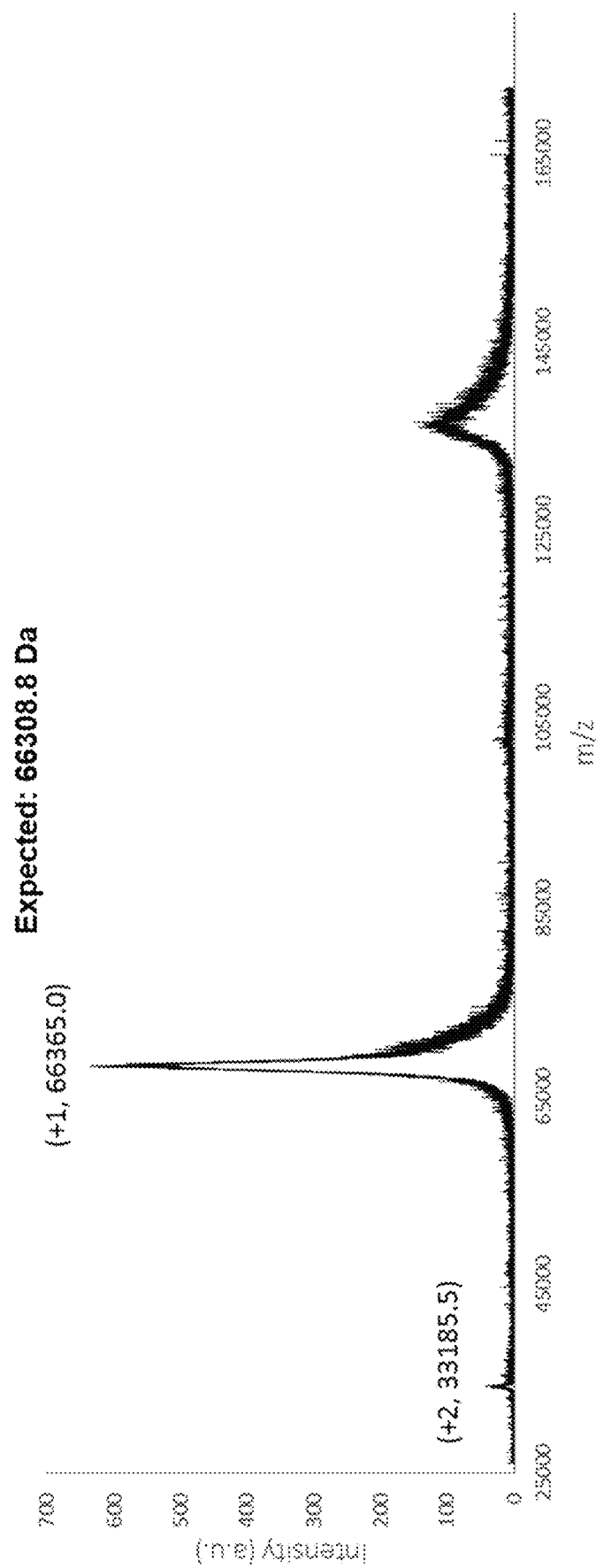
Figure 3A:
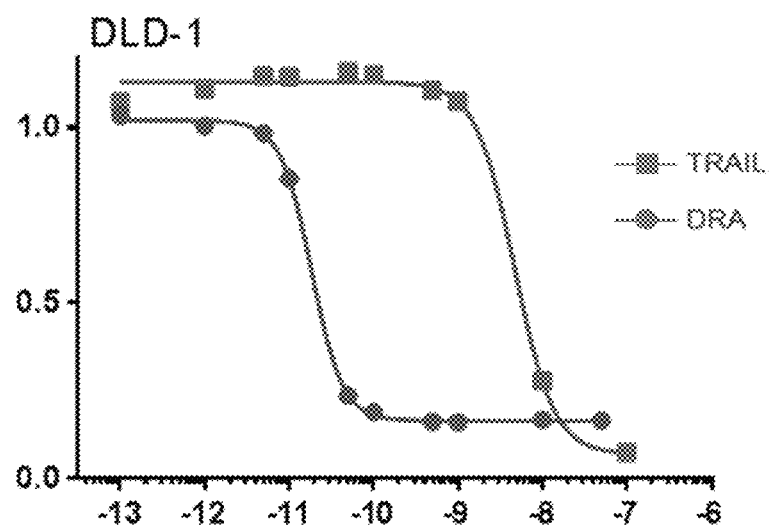
Figure 3B:
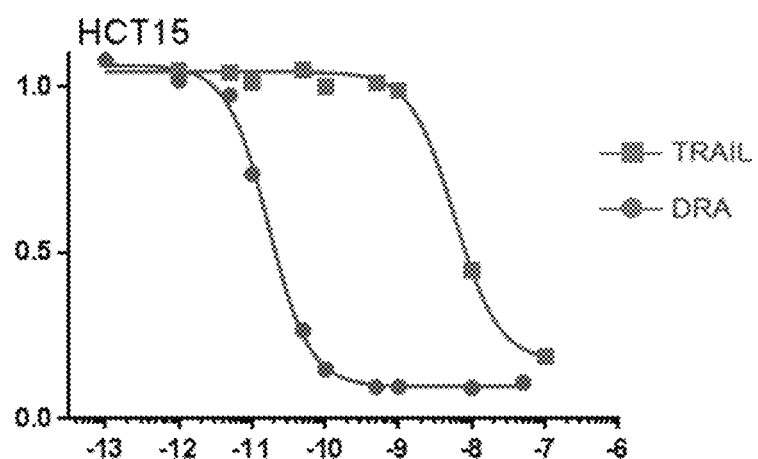
Figure 3C:
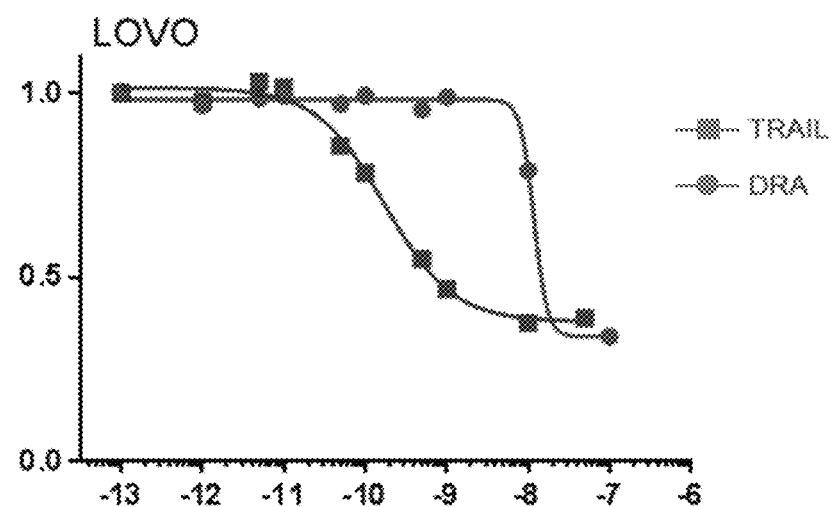
Figure 3D:
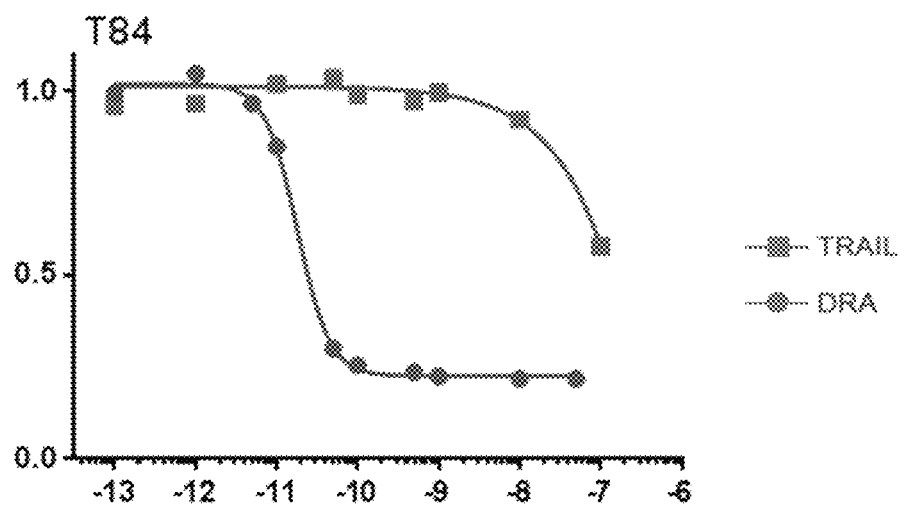
Figure 5A:
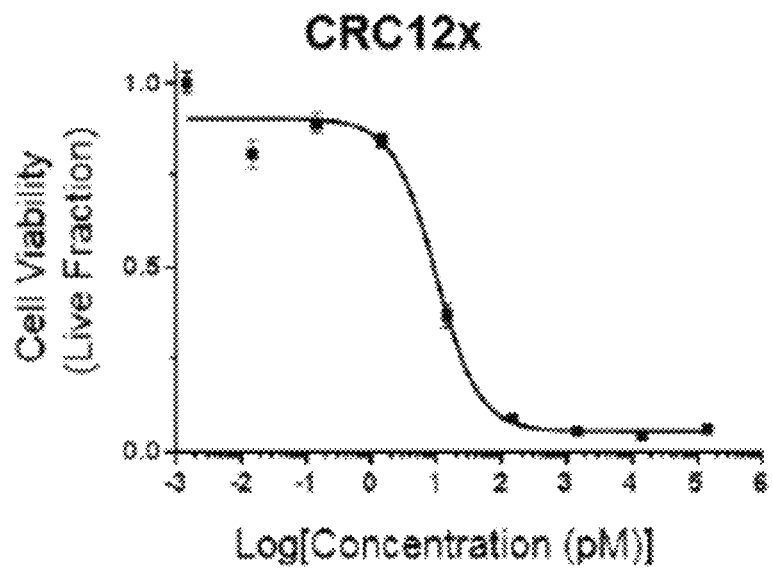
FIG. 5A, FIG. 5B and FIG. 5C show cytotoxicity dose-response curves for hexameric DRA in 3 human patient-derived cell lines. DRA potency varies in a panel of three low-passage number patient-derived colorectal cancer cell lines. DRA is highly potent in CRC12x, with an EC50 of 9.8 pM (FIG. 5A). DRA exhibits dose-responsive cytotoxicity in CRC119s, with an EC50 of 26.1 pM (FIG. 5B). CRC247 is highly resistant to DRA (FIG. 5C).
Figure 5B:
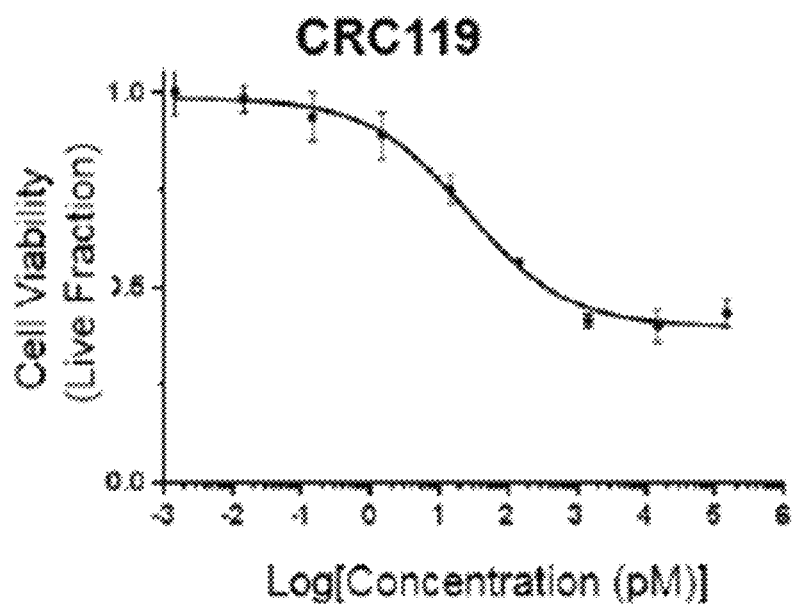
Figure 5C:
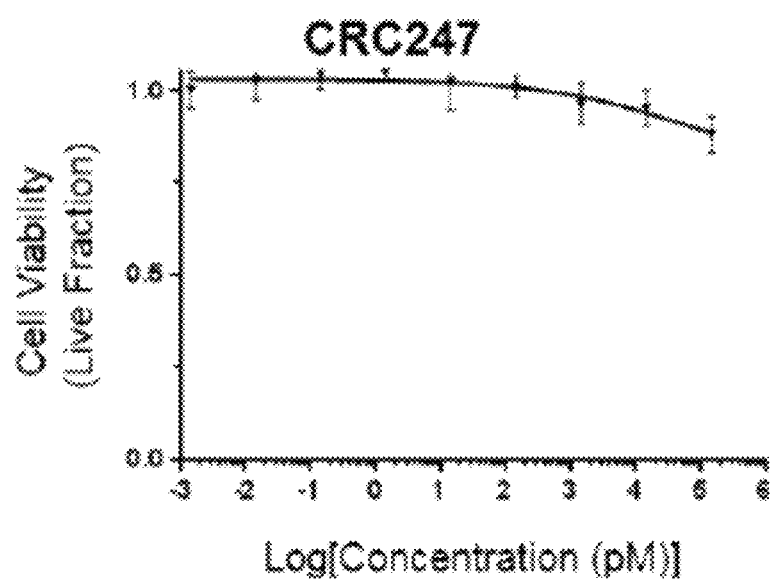
Figure 6:
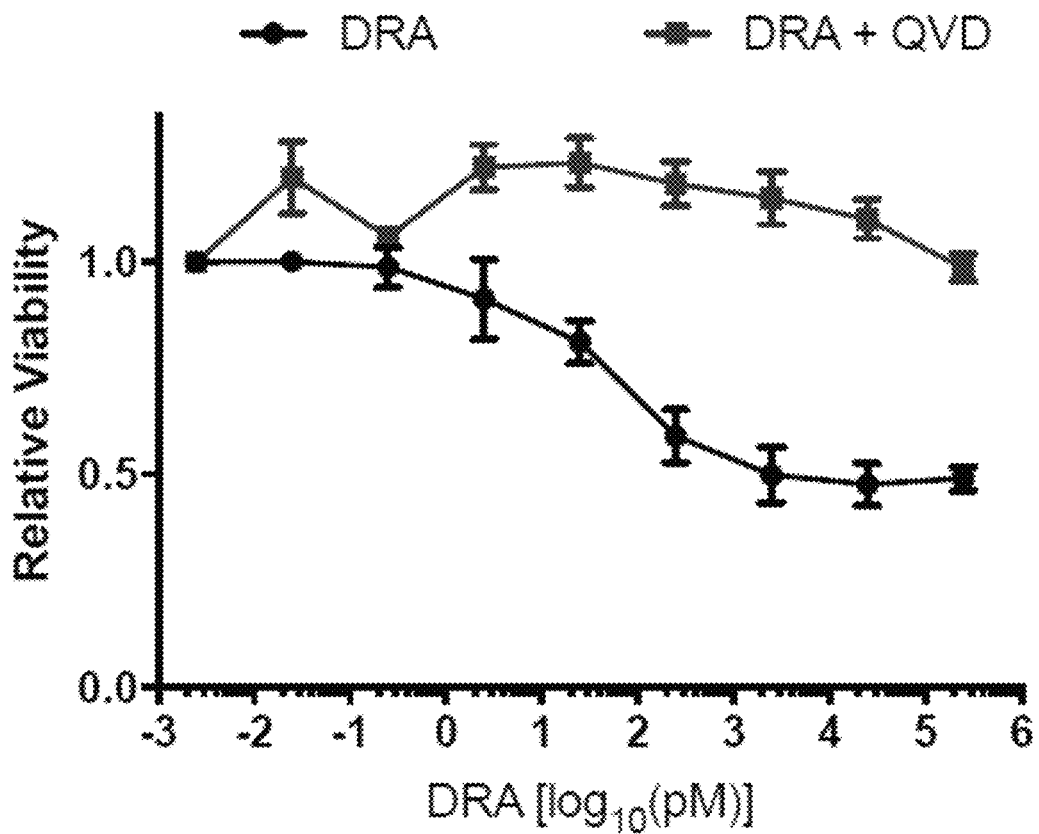
FIG. 6 is a dose response curve showing pro-apoptotic activity of the DRA is caspase-dependent. Cell viability in CRC119 human patient-derived cell line following 72 hour incubation with the indicated doses of DRA in the presence of absence of 20 μM pan-caspase inhibitor Q-VD-OPh ("OVD").

After recombinant expression of the DRA in *E. coli*, the DRA was purified and its purity was characterized by sodium dodecyl sulfate polyacrylamide gel electrophoresis (SDS-PAGE). Matrix assisted laser desorption ionization mass spectrometry (MALDI-MS) confirmed that its size was within 0.08% of its theoretical mass (FIG. 2). Its potency was next evaluated by cytotoxicity assays in a panel of human colorectal cancer cell lines with a range of TRAIL sensitivities (FIG. 1B-FIG. 1E FIG. 3, FIG. 4) and a panel of low-passage number patient-derived cell lines (FIG. 5). To confirm that the DRA induced TRAIL receptor-mediated apoptosis, the pharmacological inhibition of caspase activity with the pan-caspase inhibitor Q-VD-OPh was shown to prevent DRA activity in DRA-sensitive human cancer cells (FIG. 6). The DRA was highly potent, as it exhibited EC50 values in the picomolar range in all tested TRAIL-sensitive cell lines (FIG. 3), and in the best case was over one thousand times more potent than TRAIL (FIG. 1C). The DRA also exhibited cytotoxicity in partially or completely TRAIL-resistant cell lines (FIG. 1D), suggesting that in some instances TRAIL resistance was driven by suboptimal potency that was likely related to inefficient receptor clustering. However, despite the drastically improved potency offered by the DRA, certain cell lines, such as RKO, remained resistant to the DRA (EC50>100 nM), suggesting that additional intrinsic resistance mechanisms were operative in these DRA-resistant tumor cell lines (FIG. 1E).

Example 3

Figure 7A:
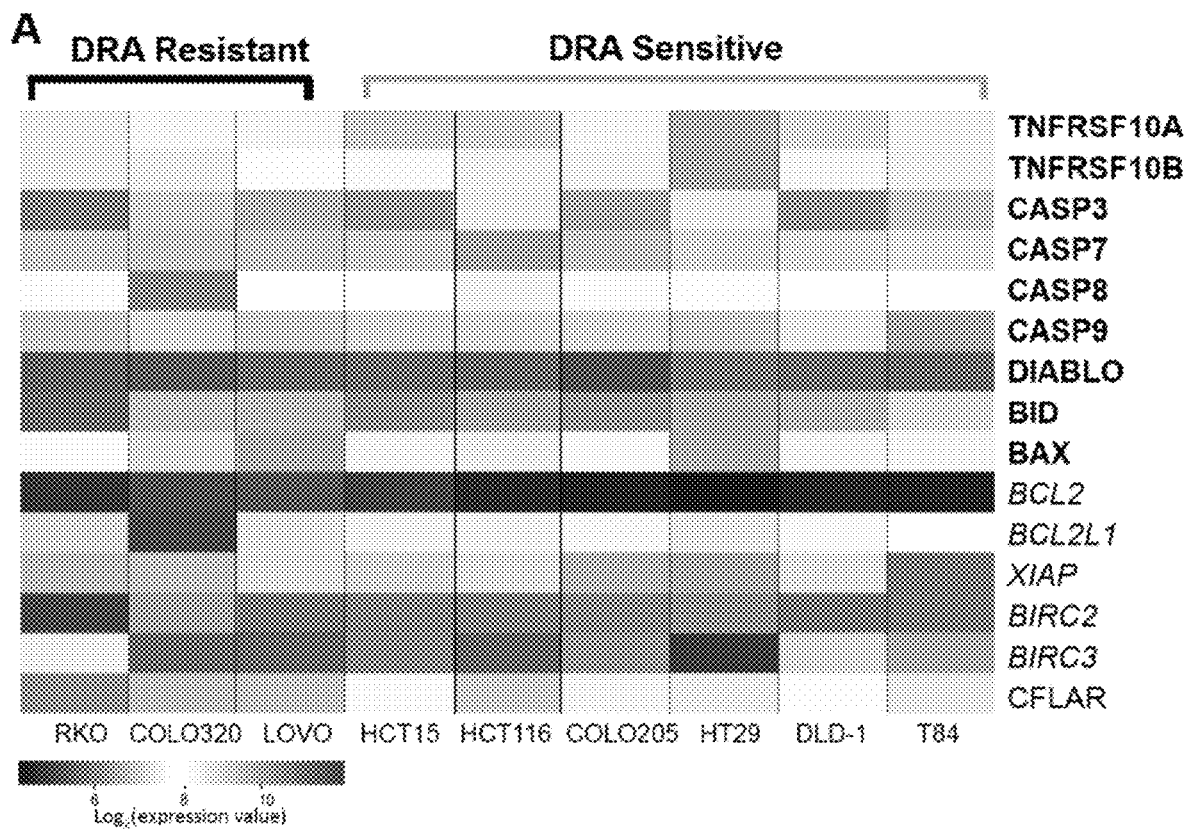
FIG. 7A, FIG. 7B, and FIG. 7C demonstrate that DRA-resistant human colorectal cancer cells are capable of undergoing apoptosis.
Figure 7B:
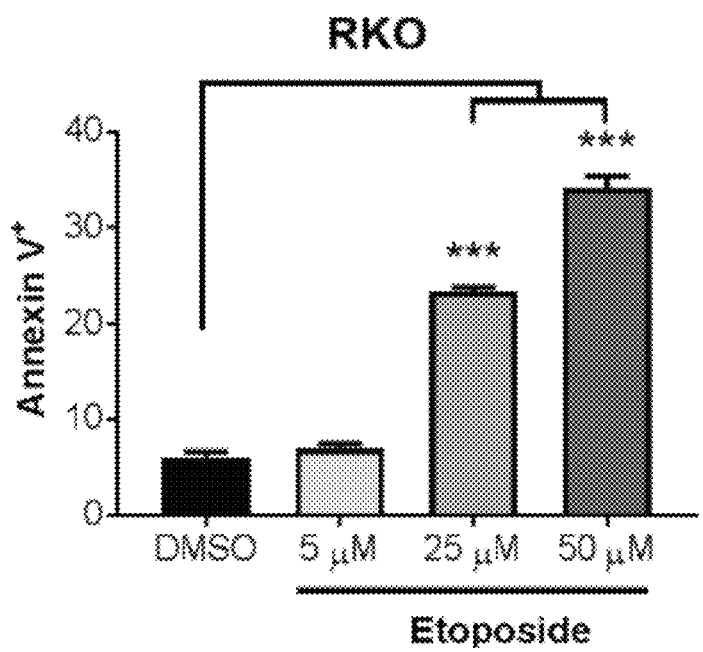
Figure 7C:
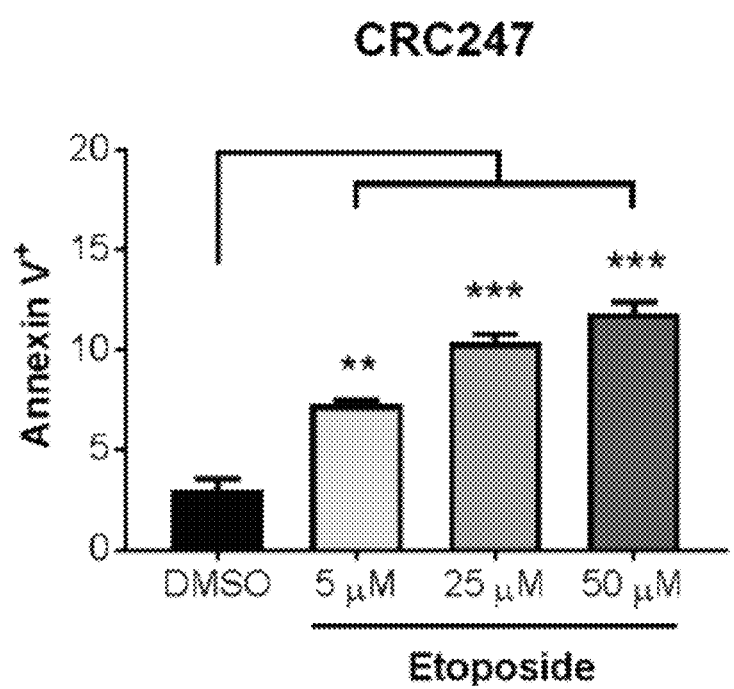
Figure 8A:
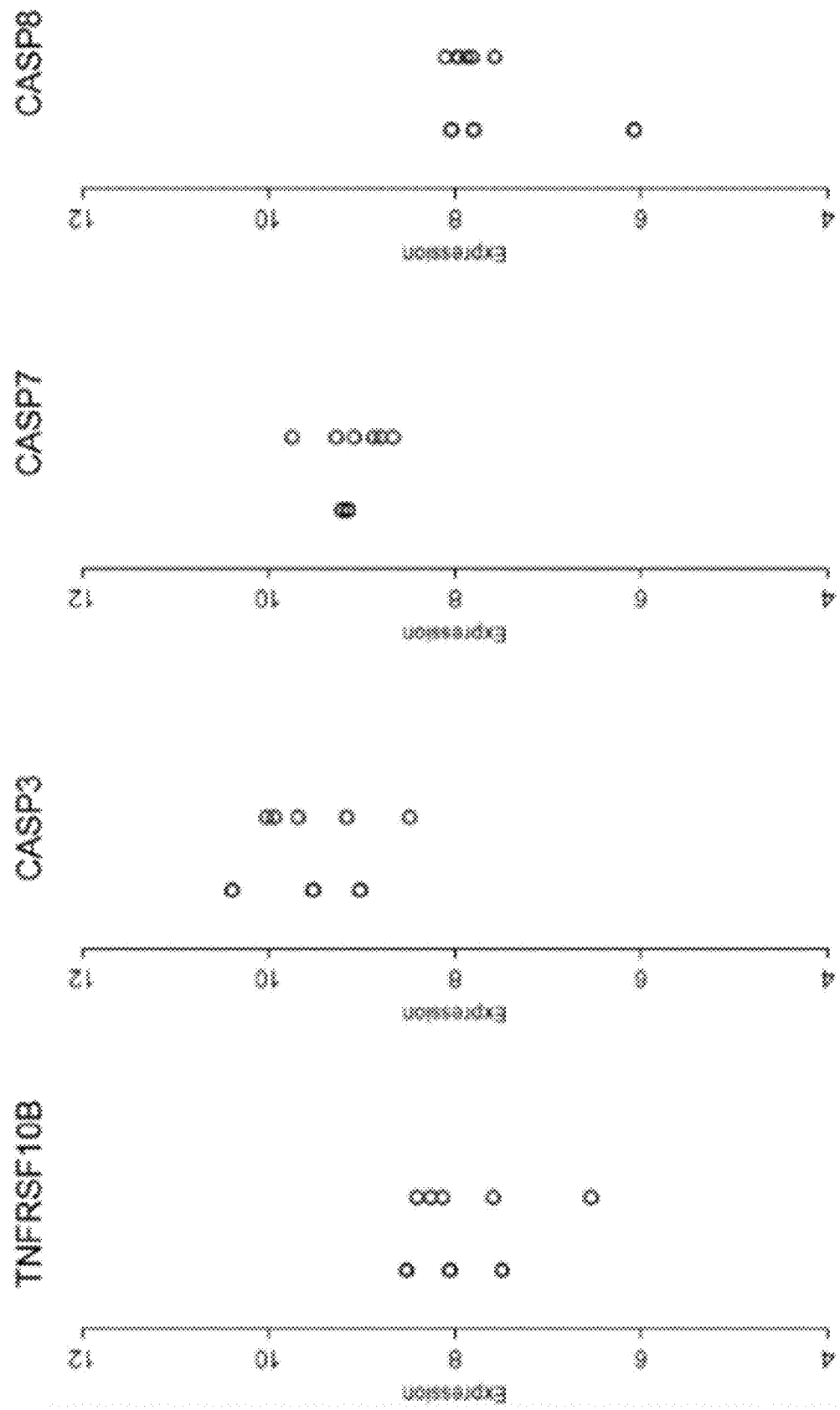
FIG. 8A, FIG. 8B, FIG. 8C, and FIG. 8D show the difference, or lack of a difference, between mRNA expression levels of genes associated with apoptosis in TRAIL-sensitive and TRAIL-resistant cell lines.
Figure 8B:
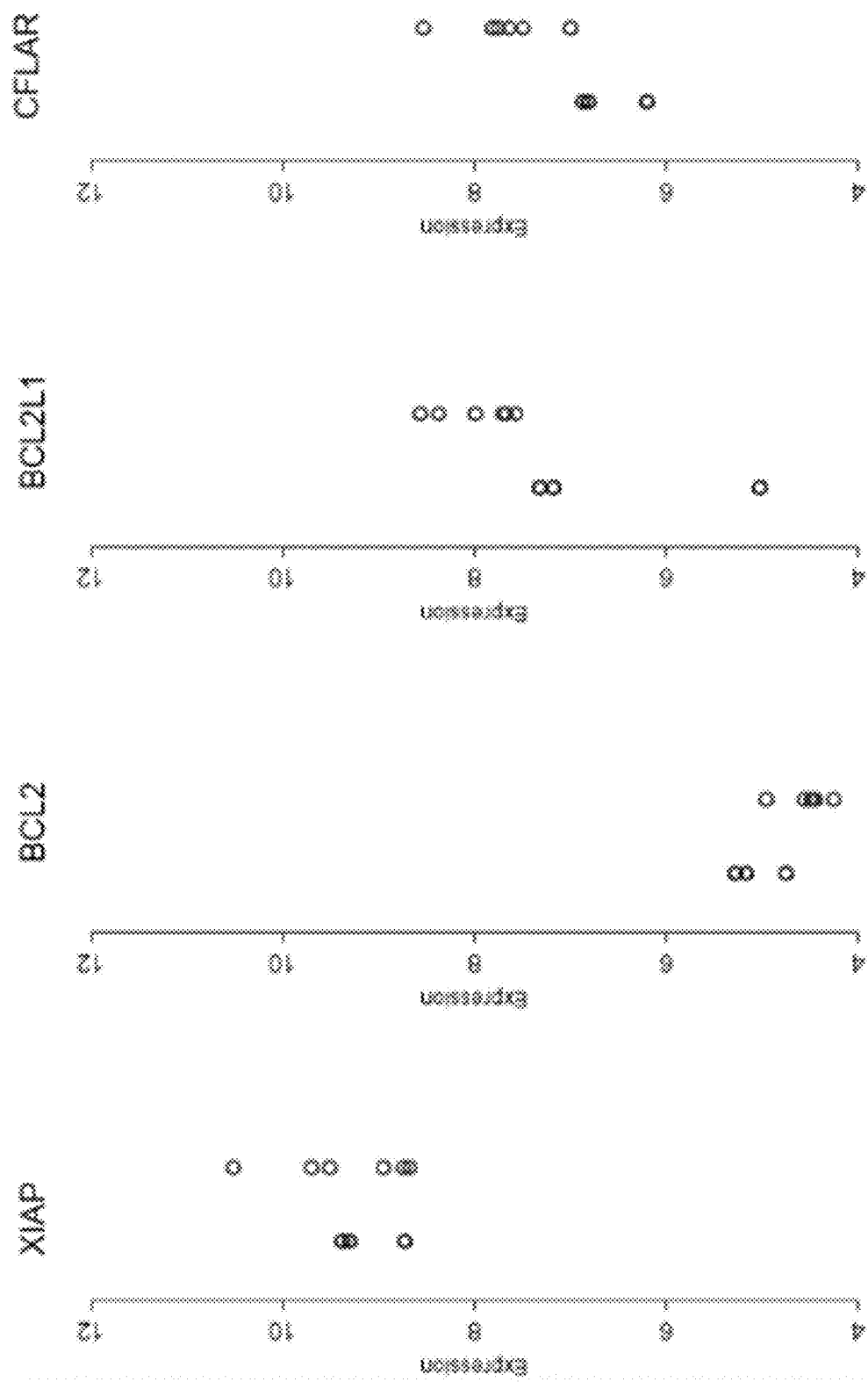
Figure 8C:
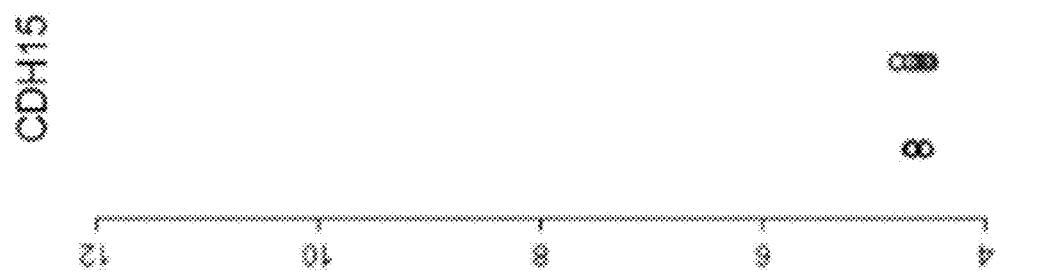
Figure 8D:
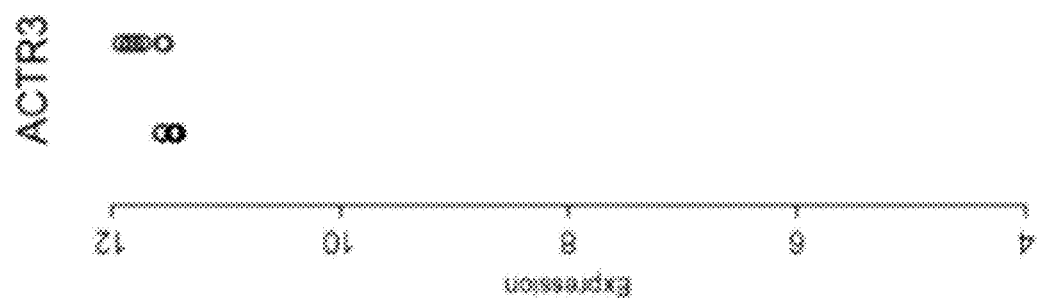

Extrinsic Pathway Gene Expression and Apoptotic Competency Fail to Explain Intrinsic Resistance In a panel of colorectal cancer cell lines (FIG. 1B-FIG. 1E, and FIG. 3), DRA sensitivity and resistance could not be trivially explained by differential expression of individual genes in the extrinsic and intrinsic apoptotic pathways, as mRNA expression data from the Cancer Cell Line Encyclopedia (CCLE) revealed no significant differences in the expression of these genes (FIG. 7A, FIG. 8). Further, hierarchical clustering of the cell lines did not lead to stratification of resistant and sensitive cell lines into separate clusters, implying that expression pattern of these genes is not a strong discriminator between the two groups. These results are consistent with a large body of literature suggesting that cancer cell resistance to TRAIL and other pro-apoptotic drugs cannot be easily explained by simple analyses of differential gene expression. Importantly, mRNA expression is not always indicative of protein levels or post-translation modification states, which themselves may have been predictive of sensitivity and resistance. Additionally, differential DRA responses were unrelated to apoptotic competence, as DRA-resistant cell lines were capable of undergoing apoptosis by treatment with the topoisomerase inhibitor etoposide for 48 h, as indicated by annexin V binding assays in two intrinsically resistant cultures, the established cell line, RKO, and a low-passage patient-derived line, CRC247 (FIG. 7B and FIG. 7C). Together, these data motivated the use of a systematic CRISPR/Cas9 knockout screen to identify functional drivers of DRA resistance.

Example 4

Genetic Knockout Screen to Identify Genetic Drivers of TRA Resistance

Figure 9A:
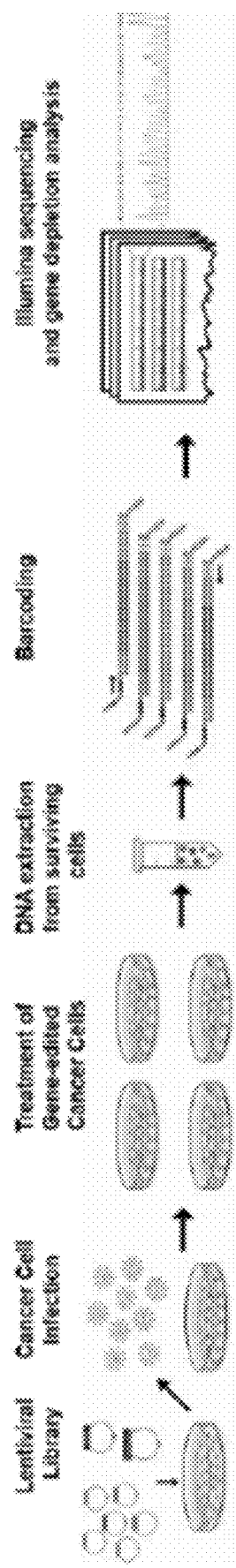
FIG. 9A, FIG. 9B, FIG. 9C, FIG. 9E, and FIG. 9F show the results from the CRISPR/Cas9 knockout screen revealing the genetic drivers of resistance to DRA, as confirmed by in vitro cytotoxicity testing of screen-informed drug combinations.

A CRISPR/Cas9 loss-of-function (LOF) screen was used to map the genetic landscape of resistance to the DRA (FIG. 9A). By coupling the results of resistance pathway screening with newly developed, long-term culture methods, it is possible to discover and credential combination therapies that delay resistance evolution. Specifically, this screening approach identifies genes that, when knocked out, confer sensitivity to the DRA in resistant CRC cells. The screen used a recently created lentiviral short guide RNA (sgRNA)/

Cas9 library targeting key nodes in major oncogenic growth, survival, and DNA damage response pathways, as well as many other potential drug targets and sensitivity modifiers (e.g., kinases, histone deacetylases, metabolic enzymes, BCL-2 family proteins, etc.).

Figure 10:
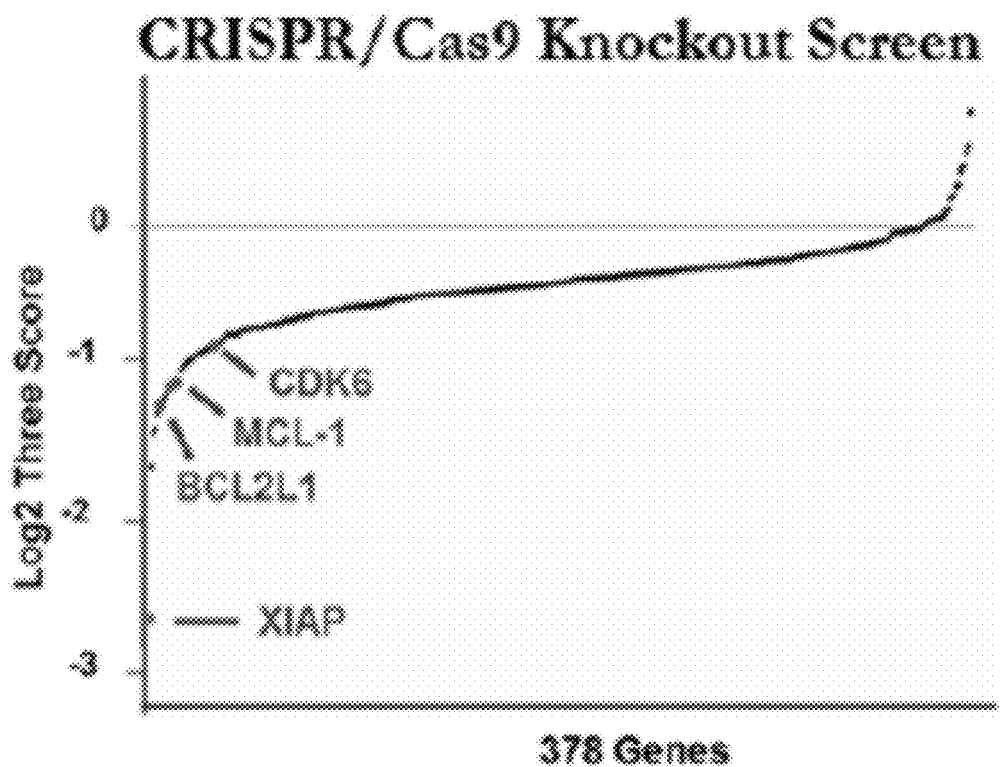
FIG. 10 includes a representative graph of the results of screening TRA-resistant human colorectal cancer cells (RKO) for genetic resistance markers using a CRISPR/Cas9 knockout library. The "3 score" represents the average of the three most depleted sgRNAs for a particular gene. Genes were ranked by log 2 of the 3 score; top hits are those that have a high negative value. Knockout of these genes sensitized the cells to TRA treatment. Four representative hits are denoted.

A library of viral vectors encoding LOF sgRNA inserts that targeted a panel of 378 druggable genes and signaling pathways was used in the LOF screen. These vectors were cloned into a lentiviral expression vector encoding Cas9, packaged with a psPAX2 plasmid, and pseudotyped with VSV-G. The pooled lentiviral library was produced by transfection of 293T cells, titered, and used to infect drug-resistant RKO cancer cells. The library of cells was then exposed to the TRAIL or the TRAILR agonist for two weeks, after which cell samples were obtained, DNA was extracted, sgRNA barcodes were isolated, and indexing primers were appended by PCR. The samples were sequenced, and the raw data was processed to identify "hits" that sensitized RKOs to each treatment, as evidenced by their depletion in drug versus vehicle treatment conditions. The depletion level of each sgRNA barcode (drug versus vehicle conditions) was calculated; depleted barcodes represent sensitizer genes. Depletion comparisons were used to generate a scoring metric called the "3 score" which represents the average of the three most depleted sgRNAs for a particular gene. The genes were ranked by their 3 scores; top hits are those that sensitized the cells to TRAILR agonist treatment when knocked out by the CRISPR/Cas9 machinery. Data are presented as the log 2 transformed mean of the 3 score per gene in the library (FIG. 10). "Hits" are genes with a high negative 3 score, and examples of the genes representing top hits are denoted in FIG. 10. The hits were subsequently filtered to retain genes that encoded proteins for which specific inhibitors are commercially available.

The sgRNA depletion metric was defined as the normalized relative abundance of each construct in the presence of TRAIL or DRA to the same quantity in the presence of vehicle. sgRNA-level depletion metrics were converted to gene-level scores using the "3-score," which represents the average of the three most depleted sgRNAs for a particular gene and is used to rank genes that, when knocked out, sensitize cells to drug treatment. Genes that drive resistance to TRAIL or DRA exhibit low 3-scores, as knockout of the gene leads to cell death in the presence of TRAIL or DRA, thus depleting cells expressing associated sgRNAs.

Figure 9B:
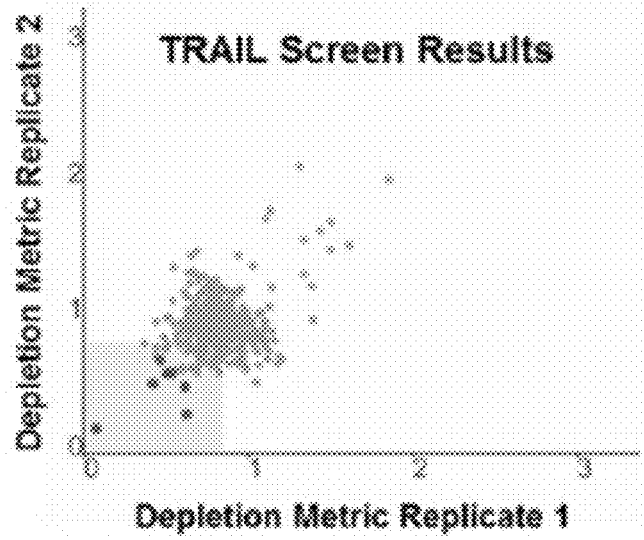
Figure 9C:
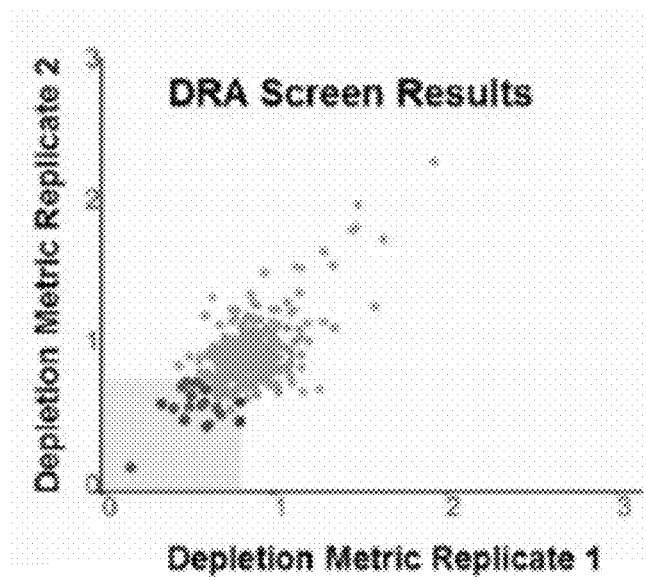

Close correspondence between the results of two technical replicates is indicated in replicate plots; these plots demonstrate the reproducibility of the screen, as matching replicate values for each gene result in a clustering of the data around the diagonal (FIG. 9B and FIG. 9C). All genes with depletion 3-score below 0.8 for both replicates were extracted for follow-up investigation; this threshold ensures that knockout of the gene results in at least 20% loss in relative cell abundance upon drug treatment. These genes were considered "hits", and examined to identify possible small molecule inhibitors that target their associated proteins. Examples of putative "hits" and their corresponding 3-scores for each replicate are shown in Table 1, alongside candidate small molecule drugs that target their encoded protein products. Interestingly, the strongest hit in both TRAIL and DRA resistance screens was the gene for X-linked inhibitor of apoptosis protein (XIAP), a result that corroborates recent findings reporting XIAP's involvement in TRAIL resistance. Other hits, albeit with lower 3-scores, included anti-apoptotic proteins like BCL-$X_L$ and the kinase CDK6.

TABLE 1

Summary of RKO cell viability results from combination of DRA with small molecule sensitizers informed from top hits of knockout screen. Background dose of each sensitizer is listed. DRA dose was varied over eight orders of magnitude and percent cell viability was normalized to sensitizer-only control. Cell viability data for each drug combination is normalized to the cell viability in the sensitizer-only treatment group. Emax, or maximum drug effect, refers to the minimum percent cell viability achieved by the DRA + sensitizer(s) combination.

| Gene | Protein | 3-score Rep1 | 3-score Rep2 | Drug(s) | Background Dose (µM) | DRA EC$_{50}$ (pM) | E$_{max}$ |
|---|---|---|---|---|---|---|---|
| XIAP | XIAP | 0.1645 | 0.117 | BV6 | 1 | 0.83 | 0.5 |
| NFKB2 | NFKB | 0.4057 | 0.5488 | Niclosamide | 0.85 | — | 0.72 |
| CDK6 | CDK6 | 0.465 | 0.686 | Palbociclib | 2 | 0.3 | 0.41 |
| HDAC8 | HDAC8 | 0.5081 | 0.5456 | PCI-34051 | 1 | — | 0.8 |
| MCL1 | MCL1 | 0.5178 | 0.6218 | A-1210477 | 10 | | 0.71 |
| YAP1 | YAP1 | 0.5509 | 0.7157 | Verteporfin | 0.56 | — | 1 |
| SRC | Src | 0.5959 | 0.5735 | Saracatinib | 1 | — | 0.77 |
| BCL2L1 | BCL-$X_L$ | 0.6213 | 0.7249 | WEHI-539 | 2 | 94 | 0.38 |
| BCL2L1, XIAP | BCL-$X_L$, XIAP | | | WEHI-539, BV6 | 2, 1 | 1.2 | 0.22 |
| BCL2L1, CDK6 | BCL-$X_L$, CDK6 | | | WEHI-539, Palbociclib | 2, 2 | 14 | 0.19 |
| CDK6, XIAP | CDK6, XIAP | | | Palbociclib, BV6 | 2, 1 | 0.3 | 0.36 |

Example 5

BCL-$X_L$, CDK4/6, and XIAP Inhibitors Potently Sensitize Cancer Cells to DRA

Figure 11:
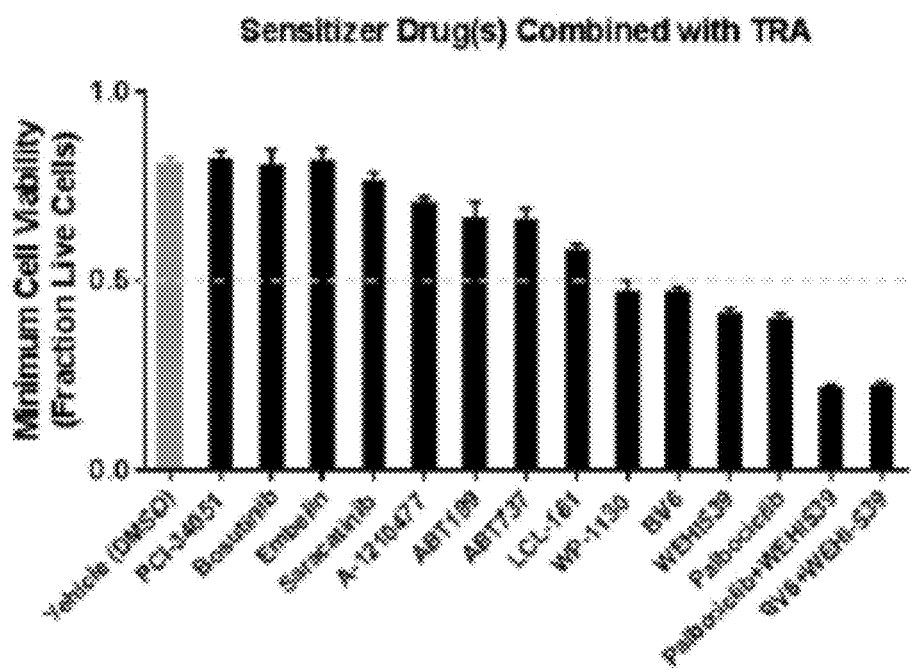
FIG. 11 includes a bar graph of representative results of treating TRA-resistant human CRC cells (RKO) with combinations of TRA and sensitizer drug(s) listed on the x-axis. Bars represent minimum cell viability achieved upon treatment of RKOs with TRA and sensitizer drug(s). All sensitizer drugs treatments were at 1-3 µM, below the $EC_{25}$ of the drug in RKOs. Low cell viability indicates superior synergy between sensitizer drug and TRA at 1 nM.
Figure 12:
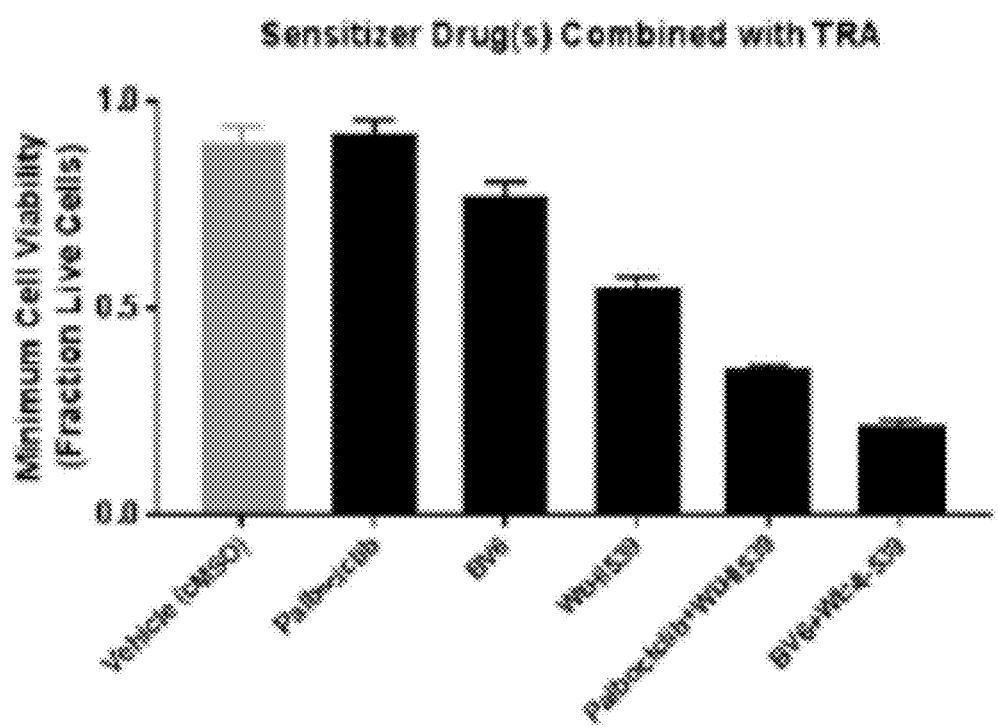
FIG. 12 includes a representative graph of the results of treating TRA-resistant human patient-derived colorectal cancer cells (CRC247) with increasing doses of TRA in combination with single dose of sensitizing agents. Cells were treated with combinations of TRA and the sensitizer drug(s) listed on the x-axis (FIG. 5A). Bars represent minimum cell viability achieved upon treatment of CRC247s with TRA and sensitizer drug(s). All sensitizer drugs treatments were at 1-3 µM, below the $EC_{25}$ of the drug in CRC247s. Low cell viability indicates superior synergy between sensitizer drug and TRA at 1 nM. Bi: Bcl-xL inhibitor WEHI-539 (2 µM); Xi: XIAP inhibitor BV6 (1 µM). The $EC_{50}$ of TRA in combination with Bcl-xL and XIAP inhibitors is 46.1 pM.

To demonstrate the efficacy of the drug combinations in human cancer lines, a series of short and long-term assays were performed. First, short-term cell viability assays were conducted in TRA-resistant RKO cells used in the knockout screen, to find synergistic drug combinations with the TRA. These assessments revealed the cytotoxic potency of each combination in human colorectal cancer cells (Table 2). The best combinations (FIG. 11 and FIG. 14) were then tested in two other human CRC cell lines and low-passage number patient-derived cell lines (FIG. 12).

TABLE 2

Drug combination cell viability results in RKO, a TRA-resistant CRC cell line. Proteins targeted for inhibition based on results from CRISPR/Cas9 knockout screen results. Sensitizer drugs were combined with TRAs and cell viability was obtained using a luminescent assay for ATP quantitation. R: resistant. If the drug combination was unable to kill more than 50% of cells, it the cells were deemed resistant to the therapy.

| Sensitizer Target | Drug | TRA GI$_{50}$ (pM) |
|---|---|---|
| | TRA Only | R |
| XIAP | Embelin | R |
| IAPs | LCL-161 | R |
| IAPs | BV6 | 0.833 |
| CDK4/6 | Palbociclib | 72.37 |
| Tyrosine Kinase | Bosutinib | R |
| Src Kinase | Saracatinib | R |
| Bcl-xL, Bcl-2 | ABT737 | R |
| Bcl-xL | WEHI-539 | 94.42 |
| Bcl-2 | ABT199 | R |
| Mcl-1 | WP-1130 | 206.7 |
| Mcl-1 | A-1210477 | R |
| HDAC | PCI-34051 | R |

Figure 9D:
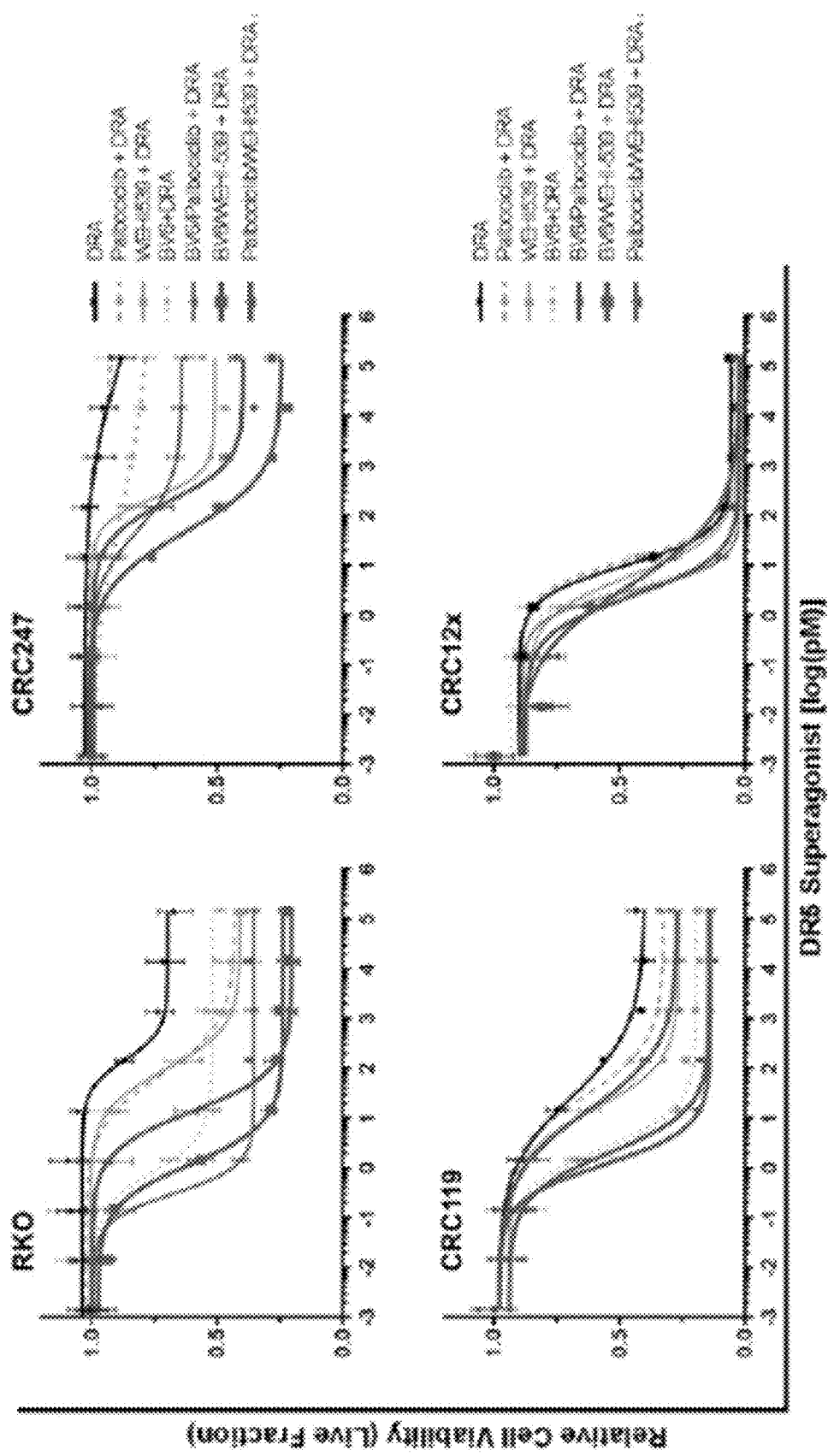
FIG. 9D are cell viability curves of combination treatment with CDK4/6 inhibitor Palbociclib, XIAP inhibitor BV6, BCL-XL inhibitor WEHI-539, and DRA in RKO cells and three human patient derived cell lines. DRA concentration on x-axis and cell viability on y-axis.

After hits were ranked based on their 3-score of depletion in each replicate, sensitization studies were performed by evaluating the in vitro cytotoxicity, in the RKO cell line, of the DRA in combination with commercially available small molecule drugs that target the proteins encoded by these hits. The cells were treated with a "background dose" of the small molecule drug and increasing doses of DRA. The selected background doses were chosen to be high enough to engage the target yet lower than or equal to the EC$_{25}$ of the sensitizer drug in the cell line; thus, cytotoxicity observed in cells treated with the sensitizer and DRA would reflect DRA-induced cytotoxicity. Cellular viability measurements associated with each combination treatment were then normalized to the viability measurement associated with the background dose alone, and as such all leftward shifts in the viability plots in FIG. 9D represent sensitization and not additive toxicity. As DRA monotherapy resulted in no cytotoxicity regardless of dose, the results of certain combination treatments were dramatic. Guidelines were set to identify the most effective sensitizers; cytotoxicity of at least 50% at 100 nM and an EC$_{50}$ of less than 1 nM were required.

Interestingly, the most efficacious drug combinations were not necessarily those targeting the hits with the best scores. This is likely due to limitations of the small molecule drugs and genetic pleiotropy. Instead, the robustness of the screen lies in its ability to provide a pool of potential sensitizer drugs for combination with the drug of interest. Drugs resulting in the lowest cell viability (described as the maximum effect, or E$_{max}$) were identified as the XIAP inhibitor BV6, the CDK4/6 inhibitor Palbociclib, and the BCL-XL inhibitor WEHI-539 (FIG. 9D). The most effective sensitizers were then paired to evaluate the most potent 3-drug combinations comprised of DRA and 2 small molecule inhibitors. As seen in FIG. 9D, Palbociclib/WEHI-539/DRA, and BV6/WEHI-539/DRA are the most efficacious drug combinations in RKO cells, resulting in picomolar DRA EC$_{50}$ concentrations.

These drugs were then tested in three human patient-derived colorectal cancer cell lines with a range of baseline sensitivities to DRA. In each case, the Palbociclib/WEHI-539/DRA, and BV6/WEHI-539/DRA triple combinations were extremely potent, sensitizing cells to picomolar concentrations (EC$_{50}$ values) of DRA and corroborating the results obtained in RKO cells (FIG. 9D, FIG. 12).

A series of complementary experiments were conducted to assess the relative toxicity of these treatments in normal, non-tumorigenic human cells. Specifically, the toxicity of DRA alone, or DRA in the presence of background doses of the IAP inhibitor BV6 and the BCL-XL inhibitor WEHI-539, in human embryonic kidney (HEK-293T), smooth muscle, and primary patient derived platelet cells. Platelets are of particular interest, as the dose limiting toxicities associated with BCL-XL inhibition in patients are driven by thrombocytopenia. The EC50 for DRA was observed, both alone and in combination with BV6 and WEHI-539, in these cells (FIG. S7) was in all cases at least 10-fold, and in most cases up to 100-fold, greater than tumor cells. Together, these results indicated that treatment with DRA and its combination with BV6 and WEHI-539 was selective for tumor cells relative to normal, non-tumorigenic cells.

Figure 14:
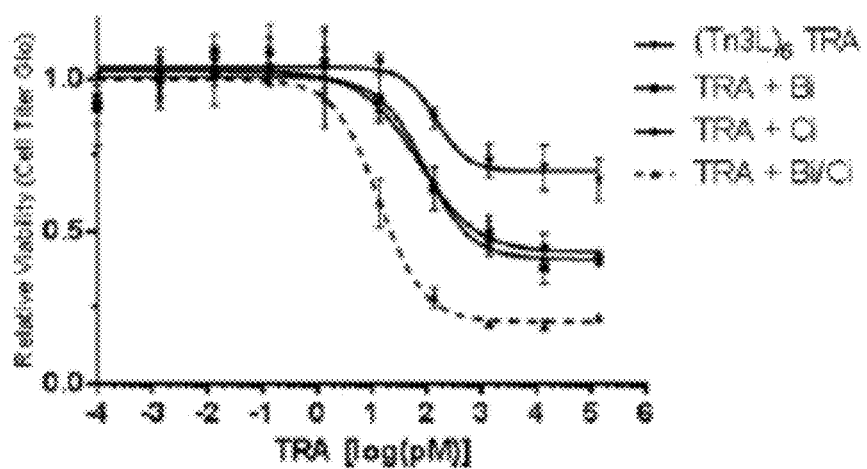
FIG. 14 includes a representative graph of the results of treating TRA-resistant human CRC cells (RKO) with increasing doses of TRA in combination with single dose of sensitizing agents. Xi: XIAP inhibitor BV6 (1 µM); Bi: Bcl-xL inhibitor WEHI-539 (2 µM); Ci: CDK4/6 inhibitor Palbociclib (2 µM). Values are normalized to sensitizer(s)' effect. The $EC_{50}$ of TRA in combination with XIAP and Bcl-xL inhibitors is 0.6 pM and $EC_{50}$ of TRA in combination with CDK4/6 and Bcl-xL inhibitors is 13.6 pM.

In short-term in vitro studies, WEHI-539 was used to inhibit BCL-X$_L$, but this drug could only be used as an in vitro tool due to the presence of a labile and potentially toxic hydrazine moiety and poor physicochemical properties. Fortuitously, as the long-term in vitro studies commenced, A-1155463, a potent BCL-X$_L$ inhibitor with in vivo activity became commercially available, and was utilized this inhibitor for subsequent studies. A-1155463 and another in vivo bioavailable alternative to WEHI-539, A-1331852, demonstrated similar synergy with TRA (FIG. 14).

Figure 9E:
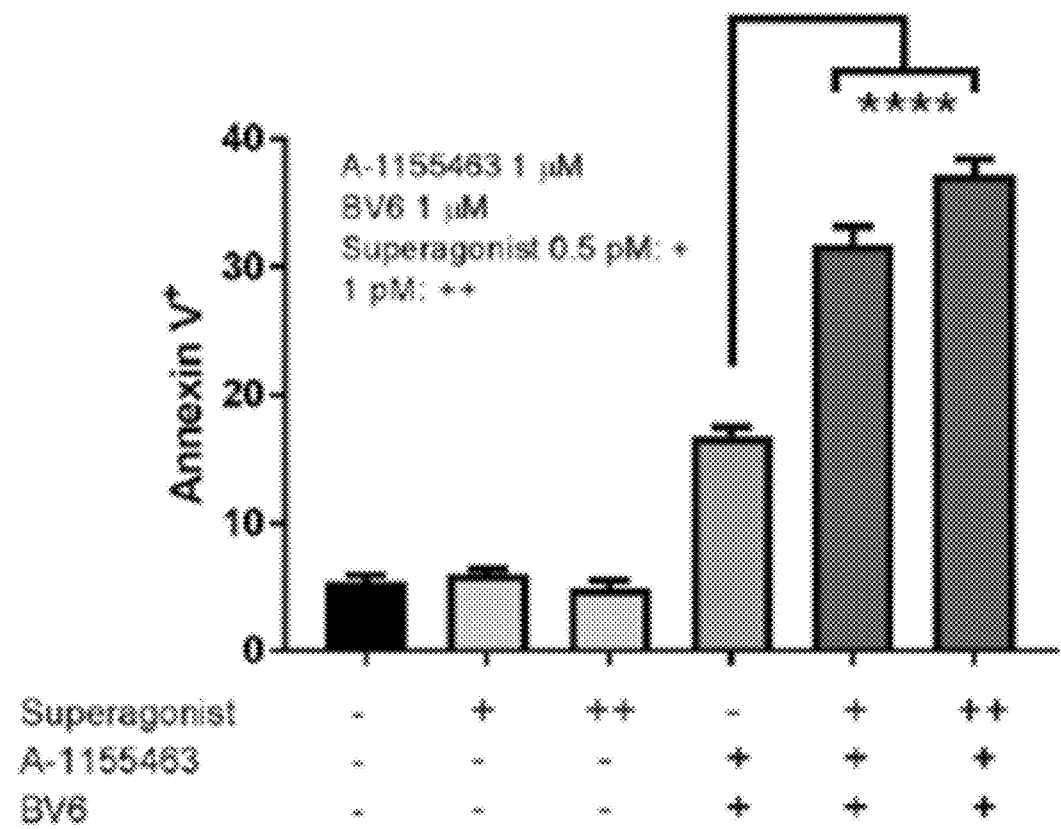
Figure 15A:
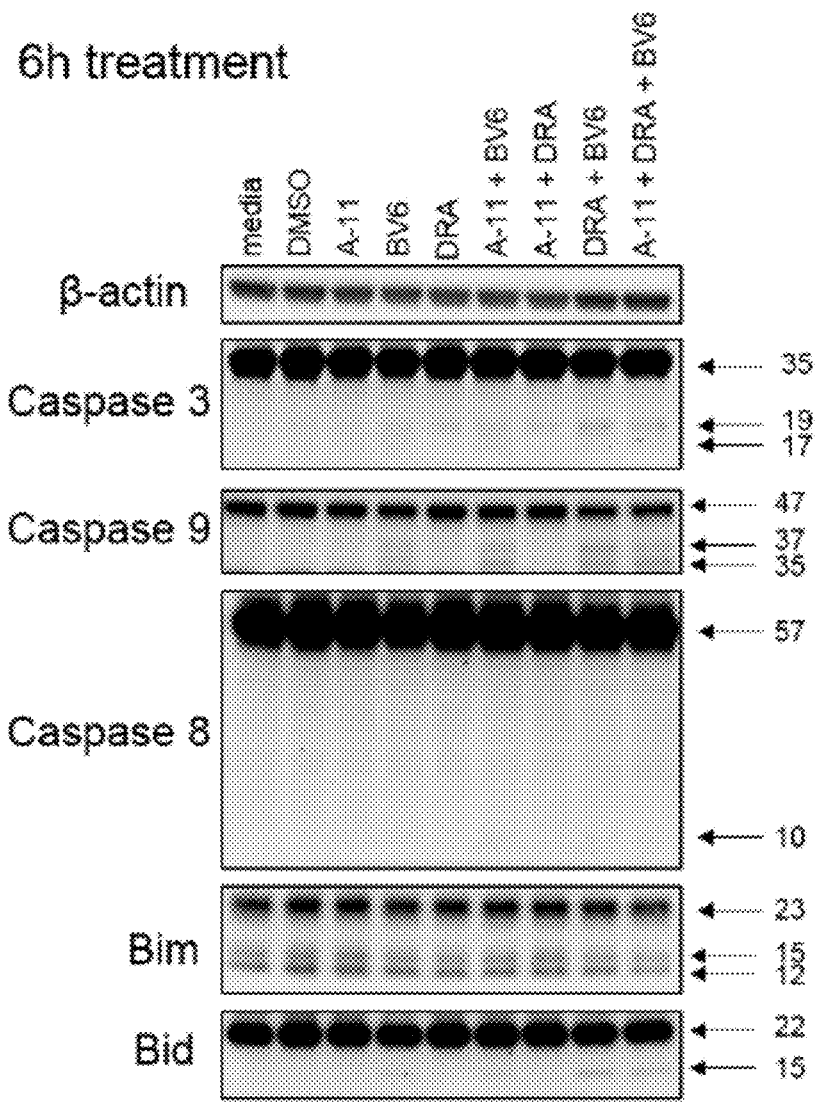
FIG. 15A and FIG. 15B include representative blots showing increased extrinsic and intrinsic pathway activation observed with combination treatments. Immunoblots of apoptotic pathway proteins in RKO cells 6 h (FIG. 15A) and 16 h (FIG. 15B) after treatment. Vehicle control was DMSO, A-11 refers to BCL-$X_L$ inhibitor A-1155463, and BV6 is the XIAP inhibitor. Cell were treated for 6 h (FIG. 15A) and 16 h (FIG. 15B) as follows: 1.5 pM DRA; 2 µM each A-11 and BV6. β-actin was used as a loading control. Numbers to the right of each blot indicate full-length protein size (higher molecular weight) and cleavage products resulting from activation of protein (lower molecular weight fragments). For instance, comparing blots at 6 h and 16 h, DRA combination with BV6 increases the appearance of lower molecular weight fragments (19 kDa and 17 kDa) of pro-apoptotic protein caspase 3 (35 kDa).
Figure 15B:
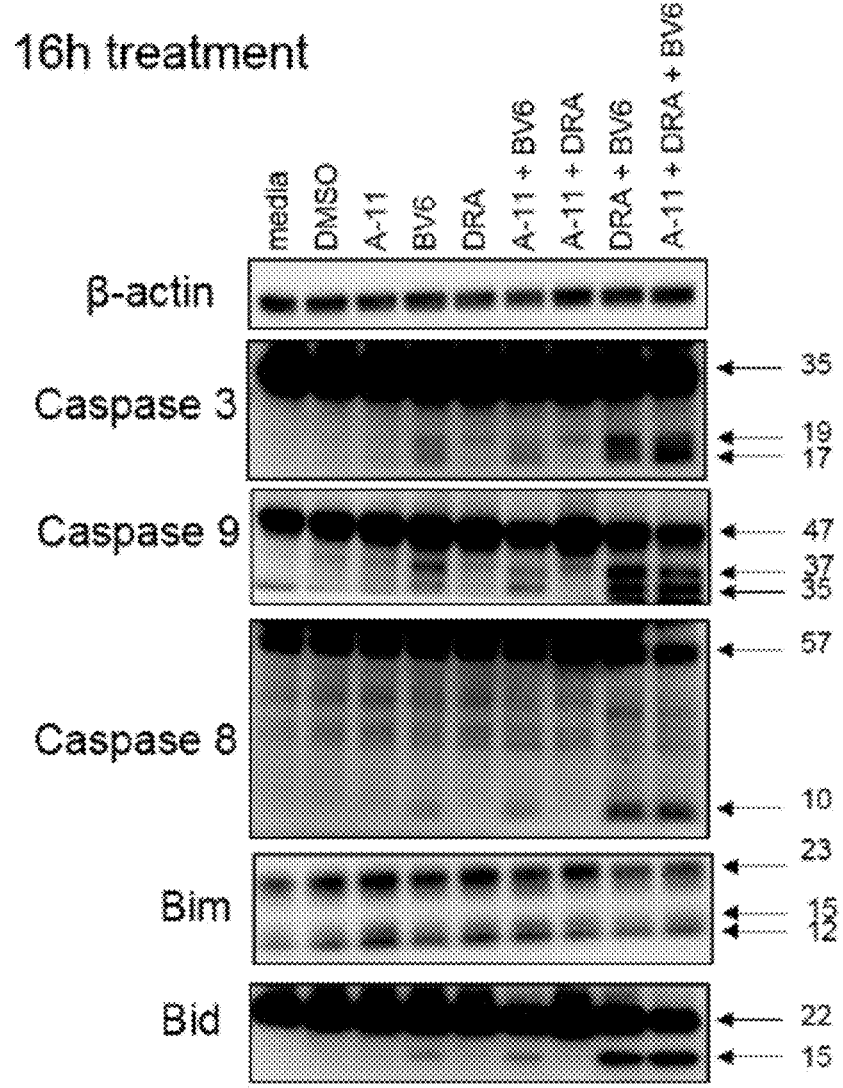

Further confirmation of cellular apoptosis was provided by quantification of Annexin V positive cells using flow cytometry; RKO cells incubated with triple drug combinations of DRA, the BCL-X$_L$ inhibitor A-1155463, and BV6 resulted in increased apoptosis of cells compared to single or double drug treated cells (FIG. 9E, Table 3). Immunoblotting from extracts derived from RKO cells treated with DMSO control, A-1155463, BV6, DRA, and dual/triple combinations reveal that proapoptotic extrinsic and intrinsic pathway caspases 3, 8, and 9, and Bid, are activated by the drug combinations (FIG. 15).

TABLE 3

Flow cytometry data for RKO treatment with drug combinations.

| Treatment | Replicate # | % positive Annexin V$^+$ | Average % positive Annexin V$^+$ | Standard Dev |
|---|---|---|---|---|
| A: DMSO only | 1 | 4.35 | 5.43 | 0.86 |
| | 2 | 6.46 | | |
| | 3 | 5.49 | | |
| B: 1 pM SA | 1 | 6.97 | 6.01 | 0.72 |
| | 2 | 5.22 | | |
| | 3 | 5.85 | | |
| C: 0.5 pM SA | 1 | 5.32 | 4.90 | 1.00 |
| | 2 | 5.86 | | |
| | 3 | 3.53 | | |
| D: A-11, BV6 1 uM | 1 | 18.41 | 16.77 | 1.24 |
| | 2 | 15.4 | | |
| | 3 | 16.49 | | |
| E: A/B 1 pM SA | 1 | 38.48 | 37.18 | 2.12 |
| | 2 | 38.87 | | |
| | 3 | 34.2 | | |
| F: A/B 0.5 pM | 1 | 33.46 | 31.74 | 2.43 |
| | 2 | 33.45 | | |
| | 3 | 28.3 | | |

Figure 9F:
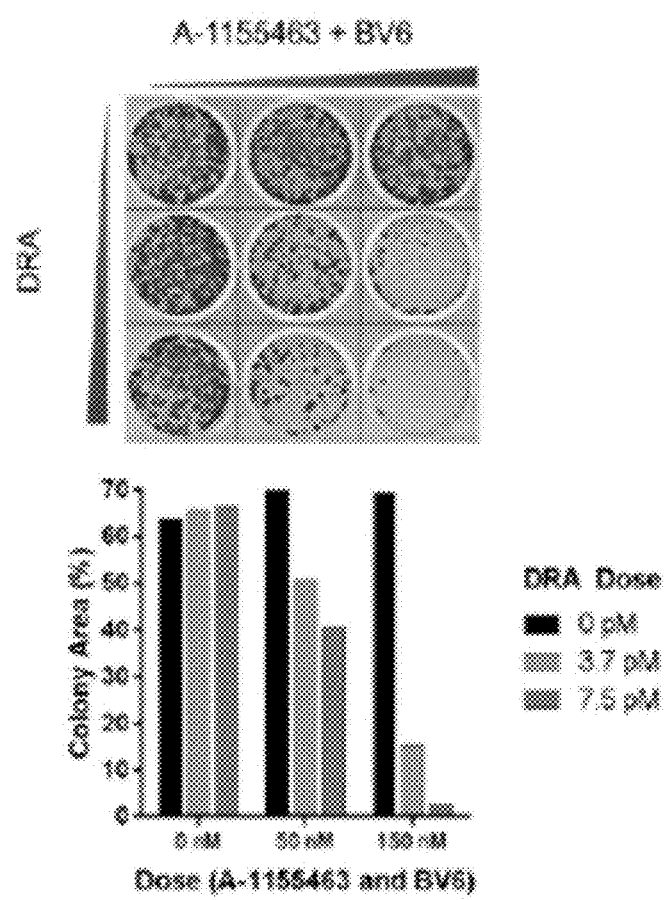
Figure 16A:
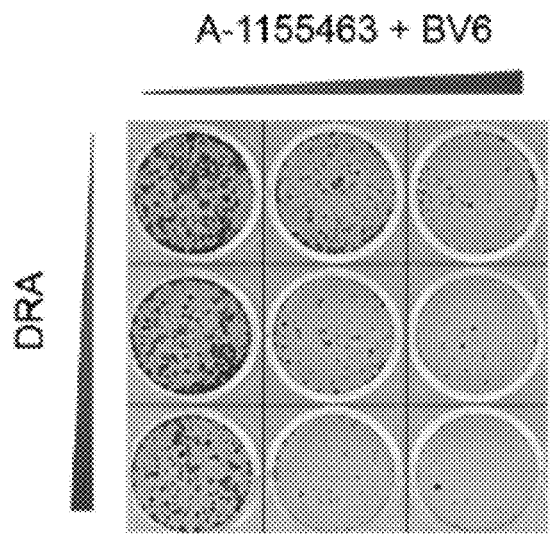
FIG. 16A and FIG. 16B include the results from a clonogenics 2D growth assay experiments in RKO cells indicating dramatically slower cell growth upon treatment with DRA in combination with sensitizer drugs.
Figure 16B:
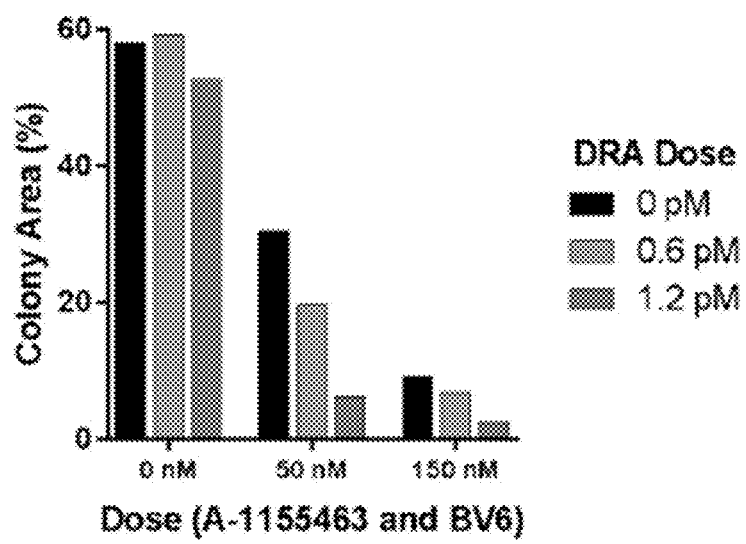

Before testing the effective drug combinations in animals, potency and robustness were evaluated in longer-term 2-dimensional (2D) growth assays. The 2D assays consisted of a drug dosing matrix in which DRA-resistant CRC247 and RKO cells are treated with increasing doses of the sensitizing drugs and DRA. The DRA concentrations were chosen as the minimum concentration required for complete growth inhibition (MinC) and two times MinC, as identified from cell viability assays. Percent colony area was quantified for each treatment condition using the ImageJ Colony Area plugin, which determines the percent area of the well covered by crystal violet and simultaneously accounts for intensity and thus cell density (FIG. 9F, FIG. 16). Images of the 2D growth assays and quantified percent colony area both demonstrated the efficacy of DRA when combined with small molecule sensitizers. The triple drug combination of A-1155463/BV6/DRA was the most effective inhibitor of cell growth, as seen in the bottom right of the 2D growth assay matrices for human CRC RKO and CRC247 cells (FIG. 9F top, and FIG. 8A). As shown in the bar graphs, the maximum concentration of each triple drug combination resulted in <5% colony growth area in both cell lines and triple drug combinations (FIG. 9F bottom, and FIG. 16B).

Figure 17:
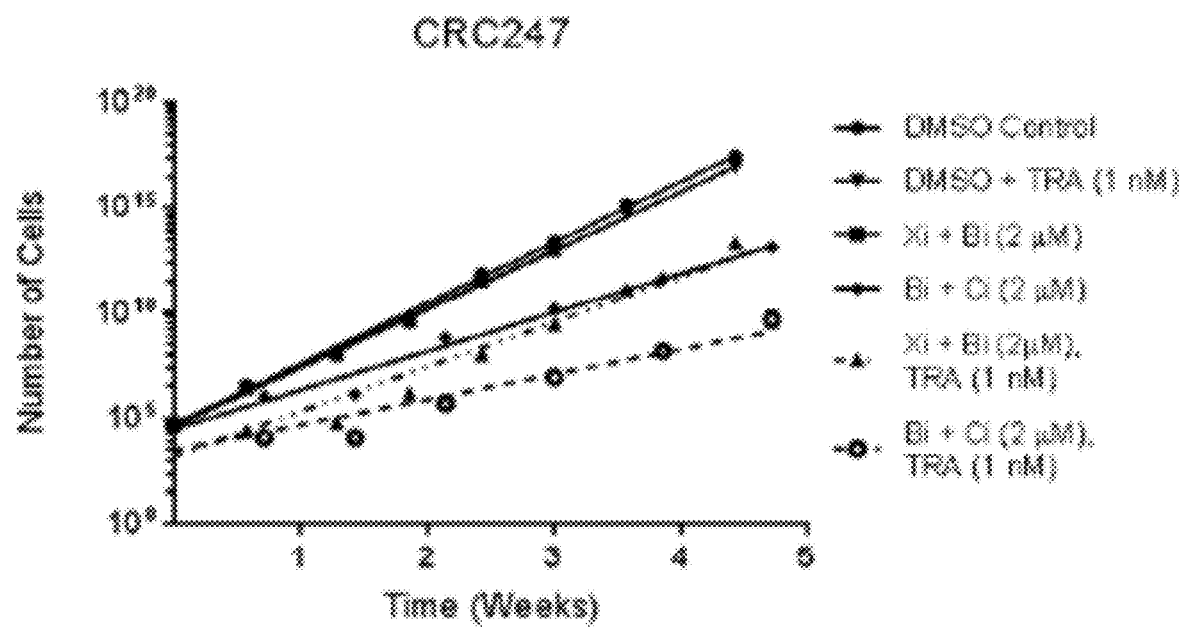
FIG. 17 includes a representative graph of the results of an in vitro time-to-progression assay in low-passage number patient-derived human colorectal cancer cells. These results demonstrate that cell proliferation is significantly reduced with combination treatments over the course of 4.5 weeks. Bi: Bcl-xL inhibitor A-1155463; Ci: CDK4/6 inhibitor Palbociclib; Xi: XIAP inhibitor BV6.

An in vitro time to progression assay was used to evaluate the efficacy of combination treatments compared to monotherapy over the course of four weeks (FIG. 17). Colorectal cancer cells were trypsinized, counted, and seeded at a density of 50,000 cells per 6 cm² plate; each treatment condition was tested in triplicate. The following day, cells were treated with vehicle, monotherapy, dual drug treatment, or triple drug combinations of interest. Media and drug were replenished every 2-3 days and cells were counted, seeded, and treated twice a week. Calculation of growth rate allowed for estimation of total cell count over time for each condition.

Example 6

ELP$_{depot}$-DRA Fusions Form Gel-Like Depots at Body Temperature and Abolish Tumors In Vivo As suggested by the discussion of the pitfalls of TRAIL in the clinic, the rational development of broadly efficacious drug combinations can enhance a targeted protein's anticancer activity, but if unaddressed, inadequate drug delivery can still prevent clinical translation. In the case of the DRA used herein, the short half-life (approximately 36 min) may require at least daily injections for in vivo efficacy. However, since proteins require systemic administration, the need for chronic outpatient therapy on a daily basis would be impractical.

The most common approach for improving pharmacokinetic properties of protein drugs is polymer conjugation, which increases the overall size of the molecule and can reduce the rate of renal filtration and proteolytic degradation. The biopolymer fusion approach integrated the advantages of polymer conjugation, longer plasma half-life than the native drug, with the unique phase behavior properties of protein-based thermally responsive polymers to generate "gel-like" coacervate depots for slow release of the DRA. Recombinant fusions of protein drugs to elastin-like polypeptides (ELPs) not only increase molecular weight, which decreases renal clearance, but also endows the fusion protein with the thermally triggered phase behavior of the ELP. ELPs are repetitive, artificial, genetically encoded biopolymers in which the repeat unit is the pentapeptide (VPGXG) (SEQ ID NO: 3), where X can be any amino acid except proline. ELPs exhibit lower critical solution temperature (LCST) phase behavior; they are soluble below their cloud point temperature, also commonly referred to as the inverse transition temperature ($T_t$) and undergo a phase transition, leading to the formation of an ELP-rich insoluble coacervate phase and an ELP-depleted aqueous phase. The identity of the guest residue (X) and the number of pentapeptide repeats are two orthogonal variables that control the Tt of an ELP. The phase behavior of ELPs may be retained upon fusion to soluble peptides and proteins, and may allow production of an injectable slow release protein drug depot, prolonging the availability of the protein therapeutic.

Figure 18A:
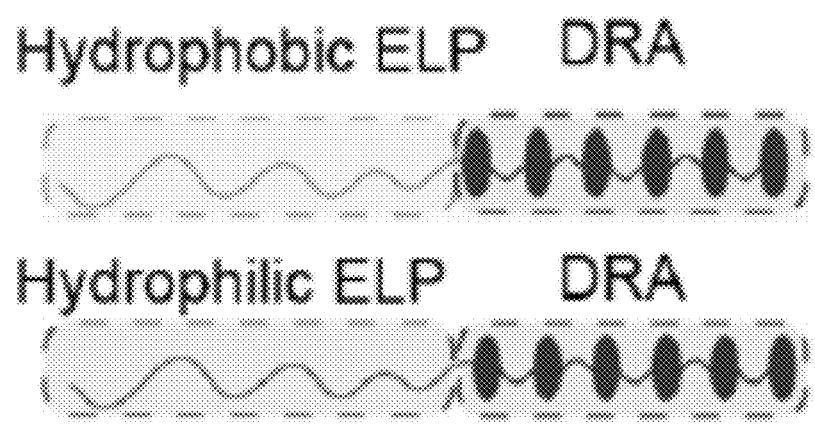
FIG. 18A, FIG. 18B, FIG. 18C, FIG. 18D, FIG. 18E, and FIG. 18F include the results demonstrating that $ELP_{depot}$-DRA fusions form gel-like depots at body temperature and abolish tumors in vivo.
Figure 18B:
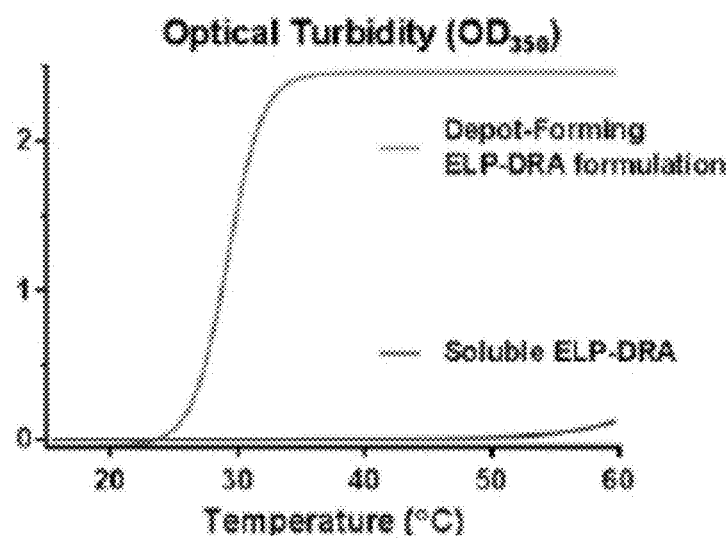

Based on this concept, a DRA-hydrophobic ELP fusion (ELP$_{depot}$-DRA) was designed for sustained release of DRA that would be soluble at room temperature, and hence easily injected subcutaneously, and which would undergo an LCST phase transition that is triggered upon warming to body temperature, leading to the formation of a s.c. depot of the ELP$_{depot}$-DRA (FIG. 18A). The sequence (VPGVG)$_{120}$, (SEQ ID NO:3) with a predicted $T_t$ of ~25° C. at an injection concentration of 100 µM in PBS, was used as the depot-forming ELP. As a molecular weight-matched ELP control to examine the impact of depot formation on DRA release and therapeutic efficacy, the DRA was fused to a more hydrophilic ELP, where X in the VPGXG (SEQ ID NO:3) repeat alternates between alanine and glycine, that does not undergo its phase transition upon s.c. injection; this fusion was named ELP$_{soluble}$ DRA. This ELP was predicted to have a $T_t$ of >50° C. in the concentration range of 25-200 µM, which was the concentration range typically injected for formation of a s.c. depot.

Figure 13A:
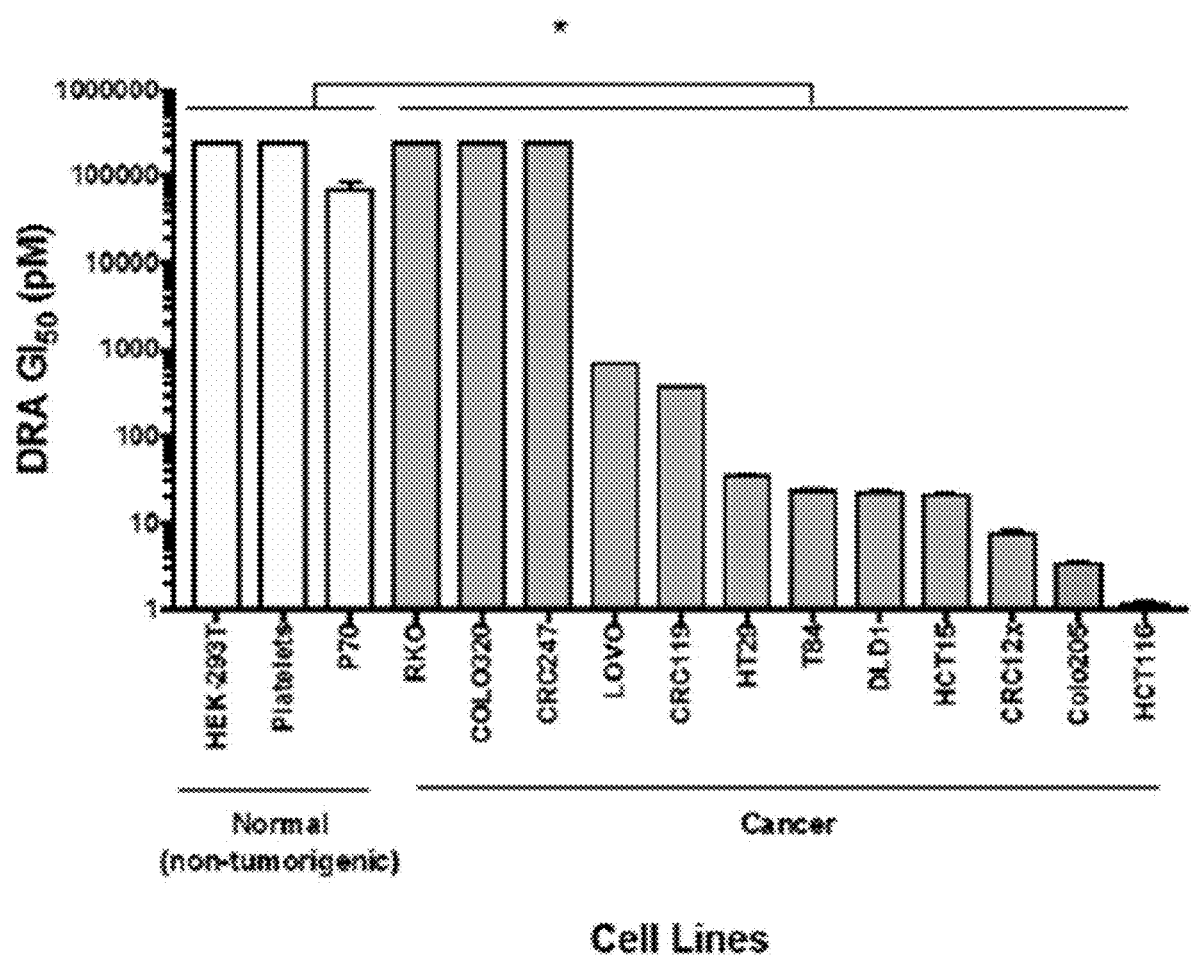
FIG. 13A and FIG. 13B include representative bar graphs showing DRA is selectively potent in human cancer cells, and combination with sensitizer drugs is relatively not toxic to normal human cells by one or more orders of magnitude. Growth inhibition-50% (GI50) values for DRA, without (FIG. 13A) or with (FIG. 13B) background doses of BV6 and WEHI-539 in a panel of normal, non-tumorigenic human cell lines (white) and primary or immortalized colorectal cancer cell lines (gray). (BV6 at 1 µM and WEDHI-539 at 2 µM) * denotes p<0.05.
Figure 13B:
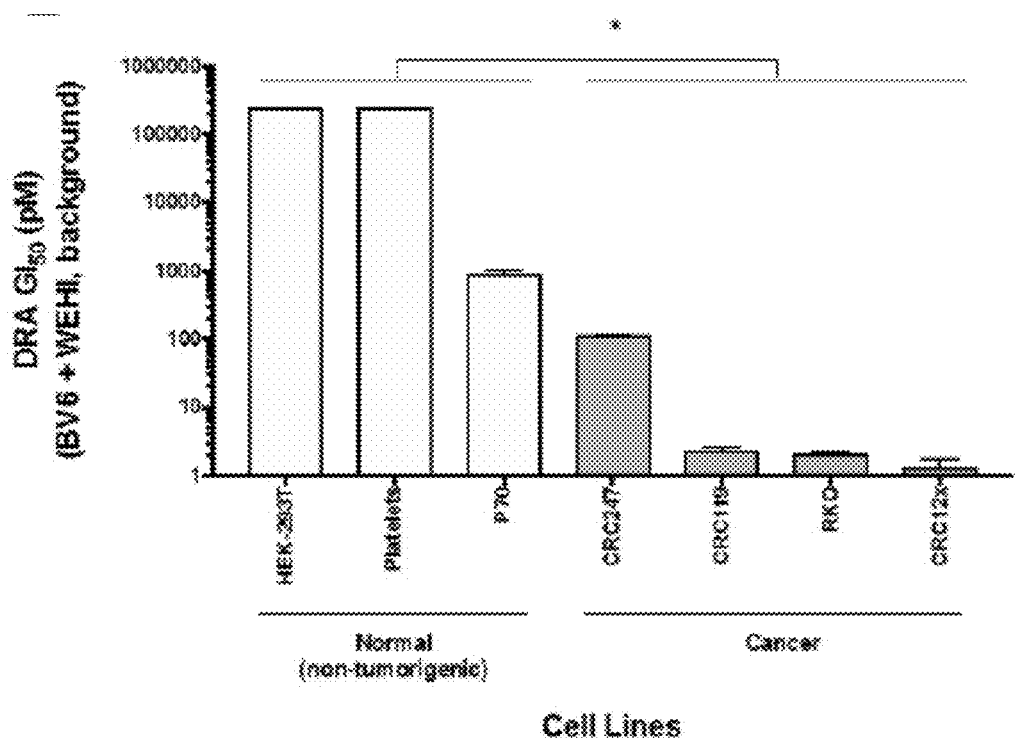
Figure 18C:
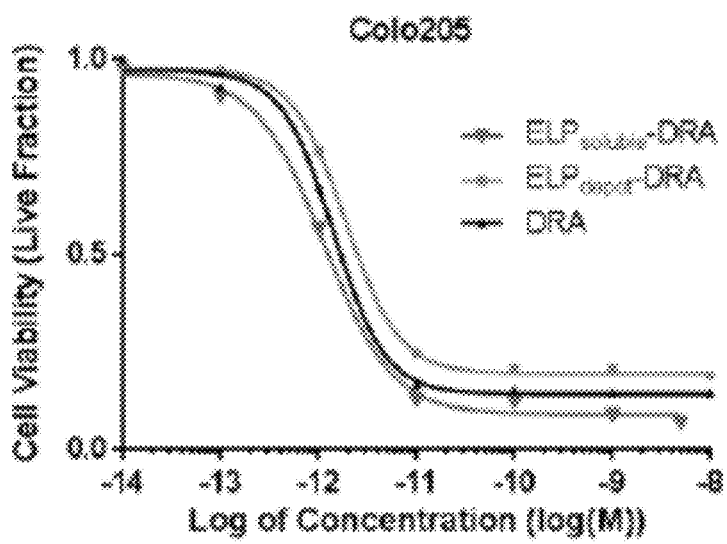
Figure 18D:
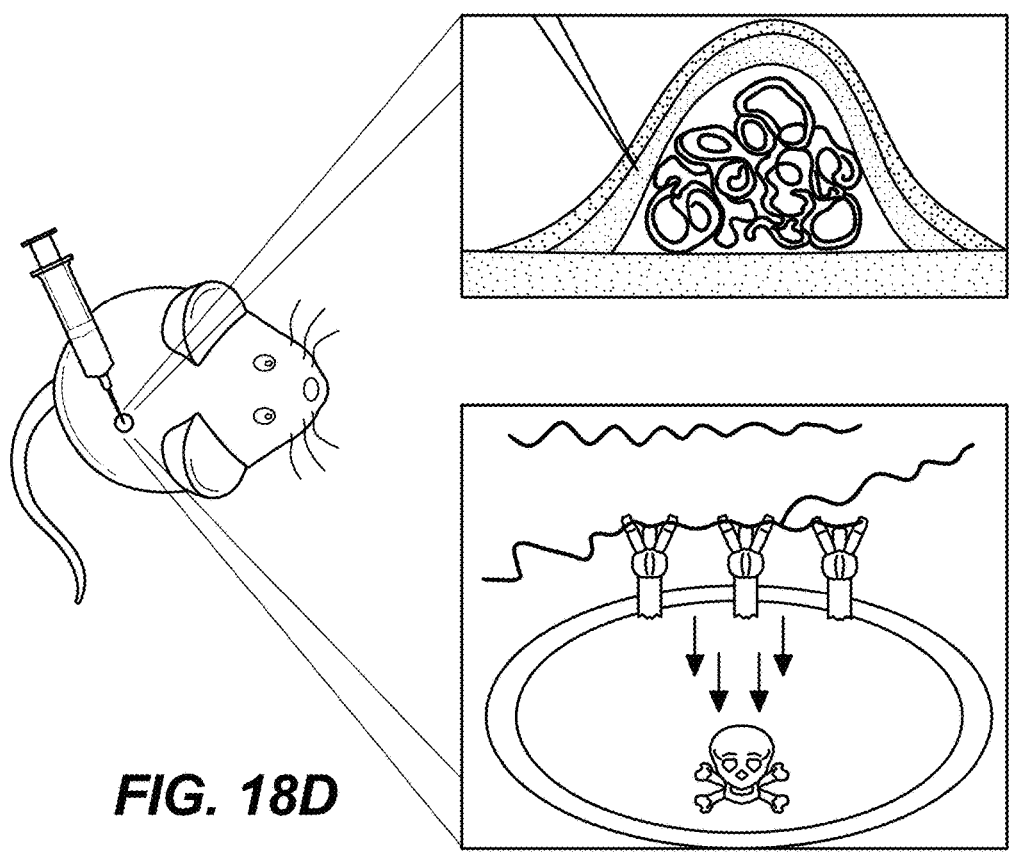
Figure 18E:
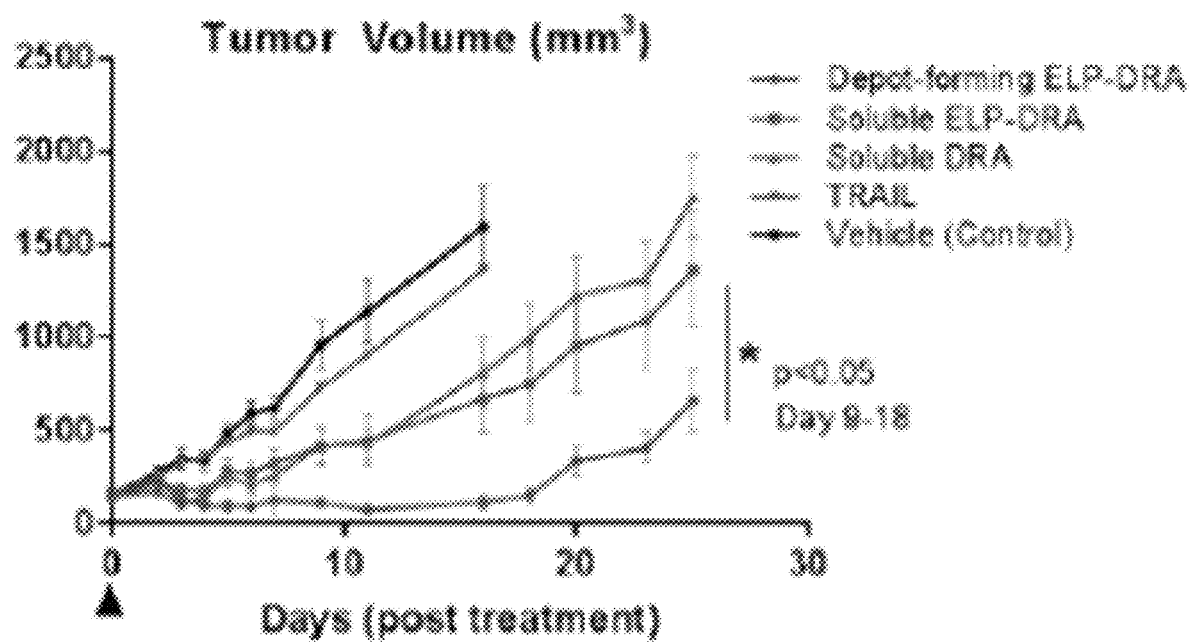
Figure 18F:
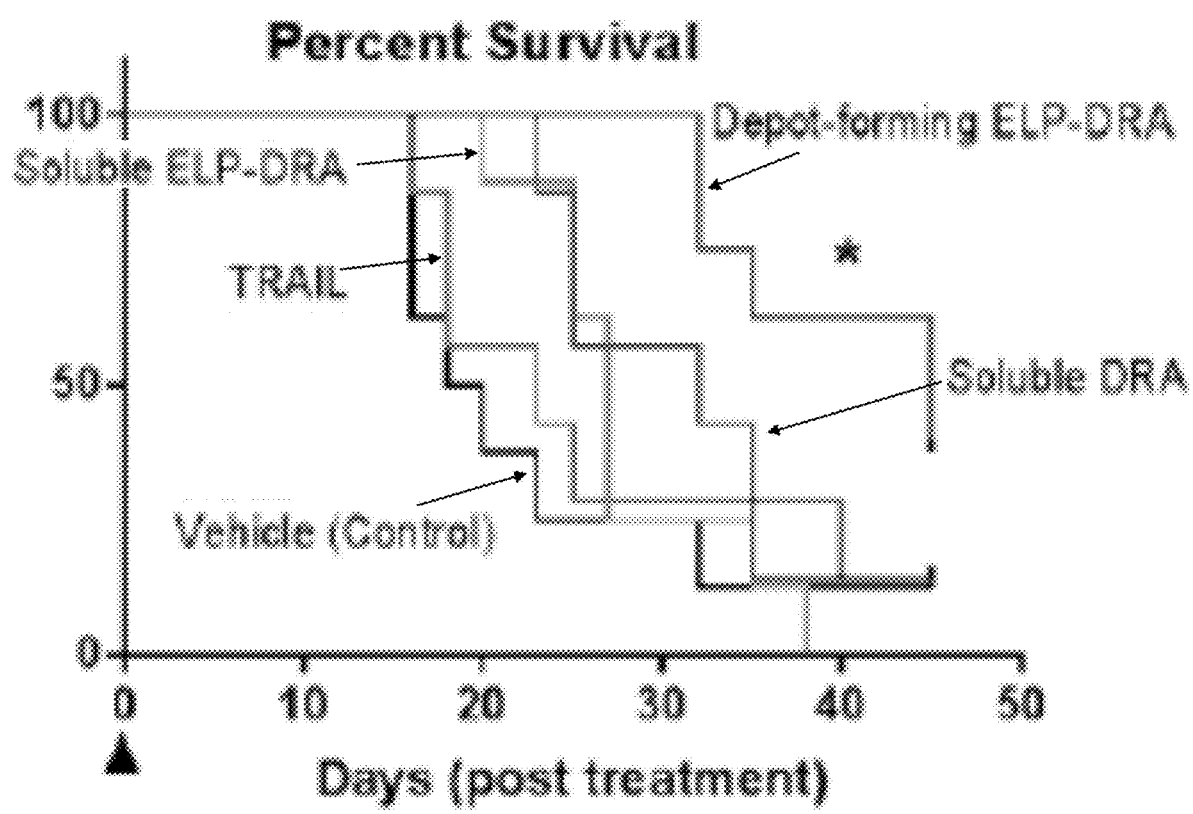
Figure 19:
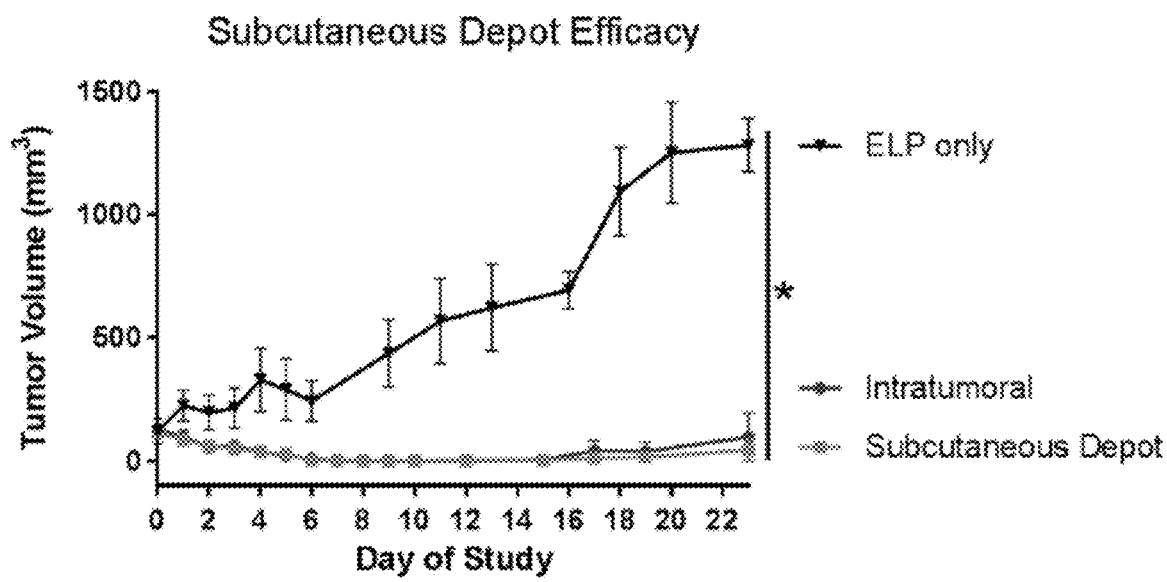
FIG. 19 is a plot showing subcutaneously injected ELPdepot-DRA formulation is as efficacious as intratumoral injection for in vivo tumor regression. ELPdepot-DRA formulation was injected once on Day 0 at 30 mg/kg molar equivalent DRA in nude mice xenografted with Colo205 tumor cells. Subcutaneous injection of the depot was performed on the left flank, and the tumor was located on the right flank. Intratumoral injection was administered at the same dose. ELP vehicle control is plotted for comparison. Two-way ANOVA followed by Fisher's LSD test results indicate statistically significant differences (p<0.05) in tumor volumes between and including days 4 and 23 for both depot-forming $ELP_{depot}$-DRA in comparison to the ELP only control.

Optical turbidity measurements demonstrated a sharp temperature transition of the depot-forming ELP$_{depot}$-DRA formulation at 27.9° C. (FIG. 18B), while the soluble ELP$_{soluble}$-DRA fusion remains soluble up to ~60° C. In vitro cytotoxicity results showed that the ELP$_{soluble}$-DRA had a similar potency as the DRA in the DRA-sensitive Colo 205 cell line, suggesting that appending an ELP to the DRA did not affect the activity of the DRA (FIG. 18C). Importantly, the DRA was specific for human DR5, as previous studies showed no interaction of the DRA with mouse death receptor. Thus toxicity data was obtained in vitro by assessing cell viability of a variety of normal human cells upon treatment with the DRA (FIG. 13A). In vivo results demonstrated that a single intratumoral injection of 30 mg/kg ELP$_{depot}$-DRA (molar equivalent of DRA) on day 0 caused growth inhibition of Colo205 s.c. xenografts and improved survival compared to intratumoral treatment with the other drugs: TRAIL, ELP$_{soluble}$-DRA, and soluble DRA, all at a 30 mg/kg DRA molar equivalent dose (FIG. 18A-FIG. 18D). A follow-up study was conducted to determine the efficacy of subcutaneous injection of ELP$_{depot}$-DRA on the contralateral flank of nude mice xenografted with the Colo205 cell line, as this mode of administration would be more clinically relevant for treatment of colorectal cancer. Intratumoral injection was administered at the same dose as s.c. administration at an ELP$_{depot}$-DRA dose of 30 mg/kg DRA equivalent. Both s.c. and intratumoral administration were equally effective, and no difference was observed between the two modes of administration (FIG. 19). All subsequent in vivo depot treatments of the ELP$_{depot}$-DRA were hence administered s.c.

Example 7

Figure 20A:
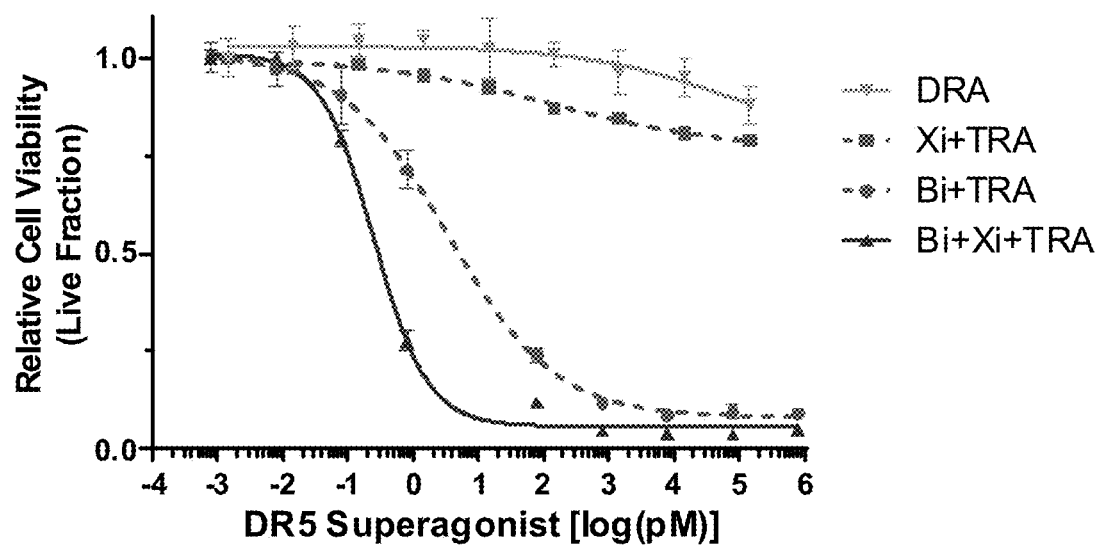
FIG. 20A, FIG. 20B, FIG. 20C, and FIG. 20D are plots showing that rationally designed drug combinations overcome $ELP_{depot}$-DRA resistance in patient-derived xenografts.
Figure 21:
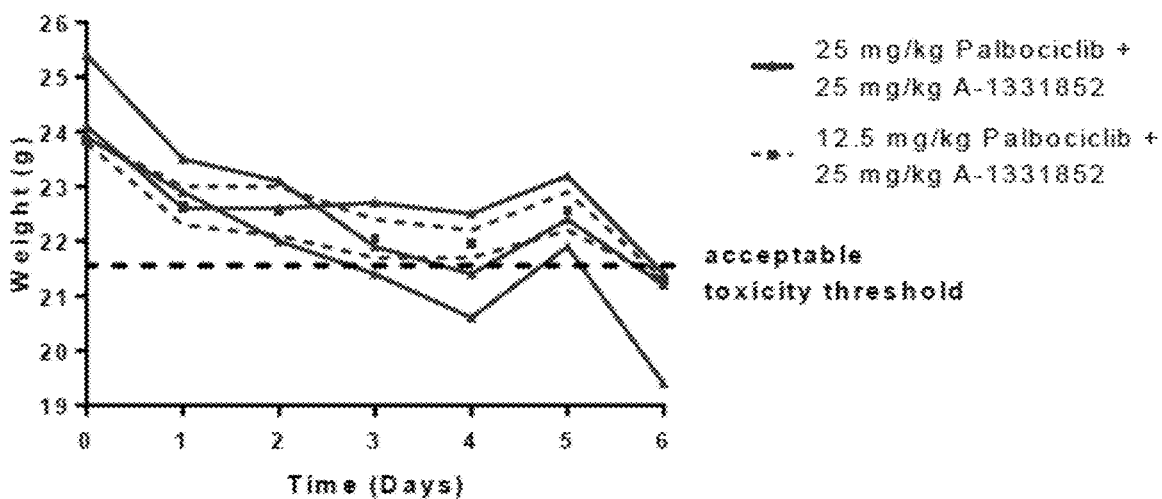
FIG. 21 is a plot showing Palbociclib combination with A-1331852 results in unacceptable toxicity in nude mice. Weight loss data for individual mice treated with A-1331852 (n=2) in combination with Palbociclib (n=2). Nude mice were treated daily with 25 mg/kg A-1331852 (p.o.) and 25 mg/kg or 12.5 mg/kg palbociclib (i.p.). Toxicity defined as weight loss >15% of pre-treatment weight.
Figure 22A:
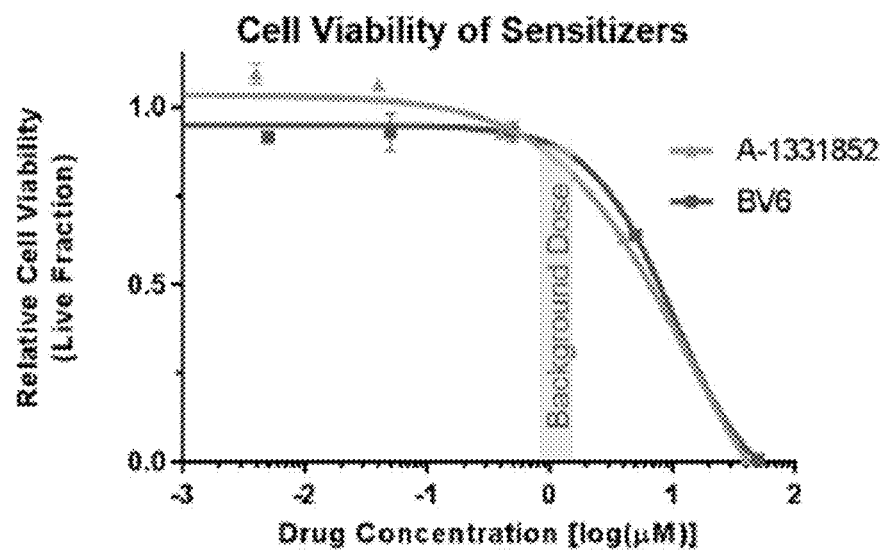
FIG. 22A and FIG. 22B include graphs of cell viability assays of single agent sensitizers in CRC247 cells.
Figure 22B:
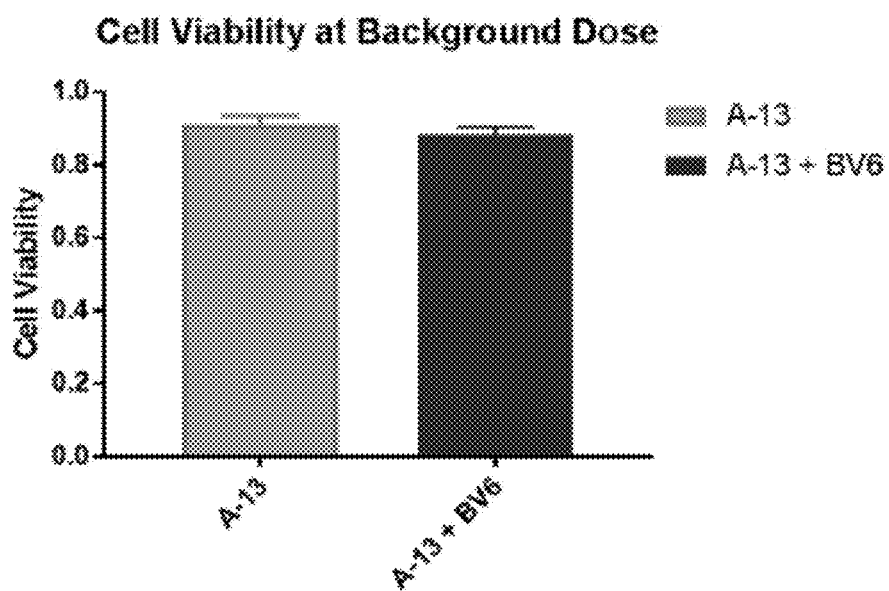

Rationally Designed Drug Combinations Overcome ELP$_{depot}$-DRA Resistance in Patient-Derived Xenografts Prior to in vivo efficacy studies, a series of cell viability assays were conducted to confirm activity of the intended drug combinations (FIG. 20A). An improved BCL-$X_L$ inhibitor, A-1331852 is orally bioavailable and exhibits ten times the potency of A-1155463. A small pilot toxicity study was conducted, in which A-1331852 was administered in combination with BV6 or Palbociclib to nude mice. Unfortunately, Palbociclib was too toxic in combination with A-1331852 (FIG. 21). The remainder of the studies was focused on the combination of BV6 and A-1331852 with the DRA. First, testing of A-1331852 in combination with DRA and BV6 was necessary to ensure in vitro efficacy in DRA-resistant CRC247 patient-derived cells before proceeding with tumor growth inhibition studies. A background dose of 1 µM of BV6 and 2 µM of A-1331852 (A-13) exhibited no cytotoxicity in CRC247 cells (FIG. 22); any effect seen in combination treatments with DRA was due to the sensitization effect of these drugs to DRA treatment. The DRA had poor efficacy in the patient-derived CRC247 cells across an 8-log range of concentration up to a maximum concentration of 1 µM, and addition of the XIAP inhibitor BV6 only had a modest effect on cytotoxicity. In contrast, combination treatment of the BCL-$X_L$ inhibitor A-13 with DRA yielded a dramatic effect on cytotoxicity, as seen by the cell killing at low pM concentrations of the DRA (FIG. 20A). Treatment with all three drugs, A-13/BV6/DRA (A+B+DRA) was even more potent than A-13/DRA (A+DRA) treatment, as it resulted in subpicomolar $EC_{50}$ for the DRA and >96% cell kill in a three-day in vitro assay (FIG. 20A).

Figure 20B:
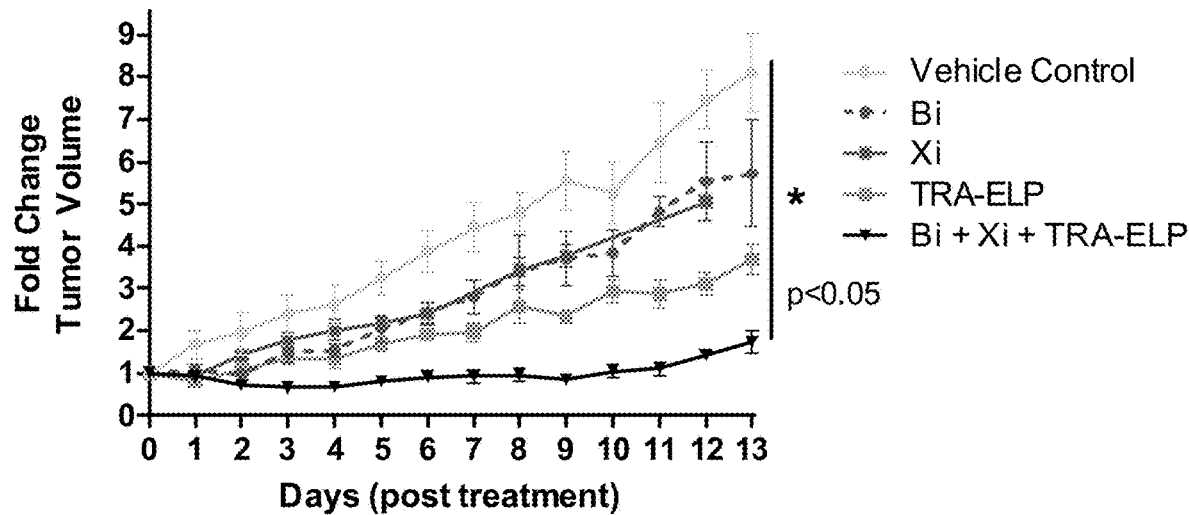
Figure 20C:
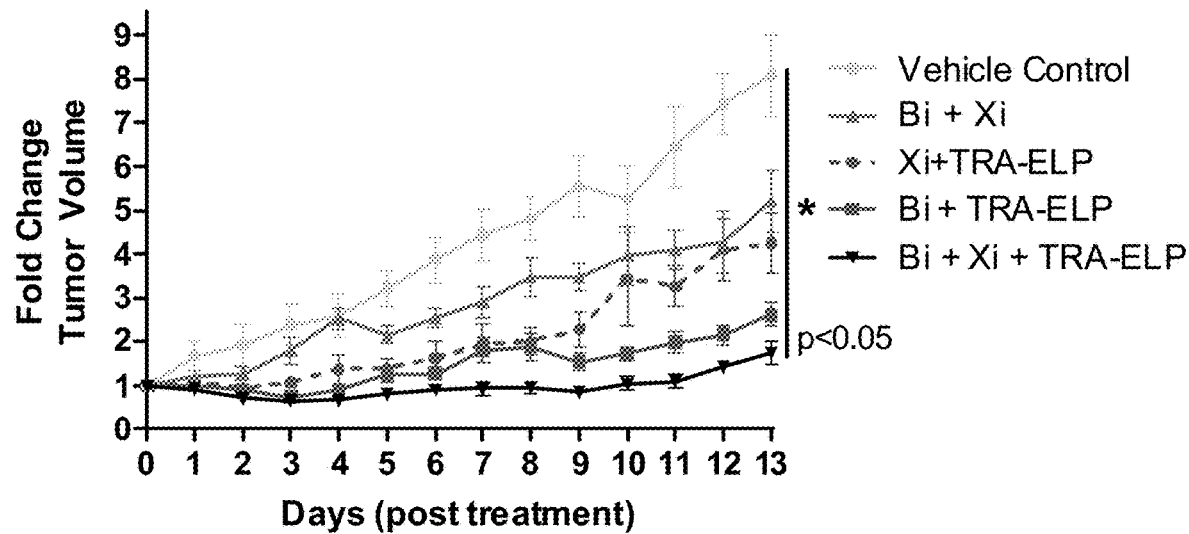
Figure 20D:
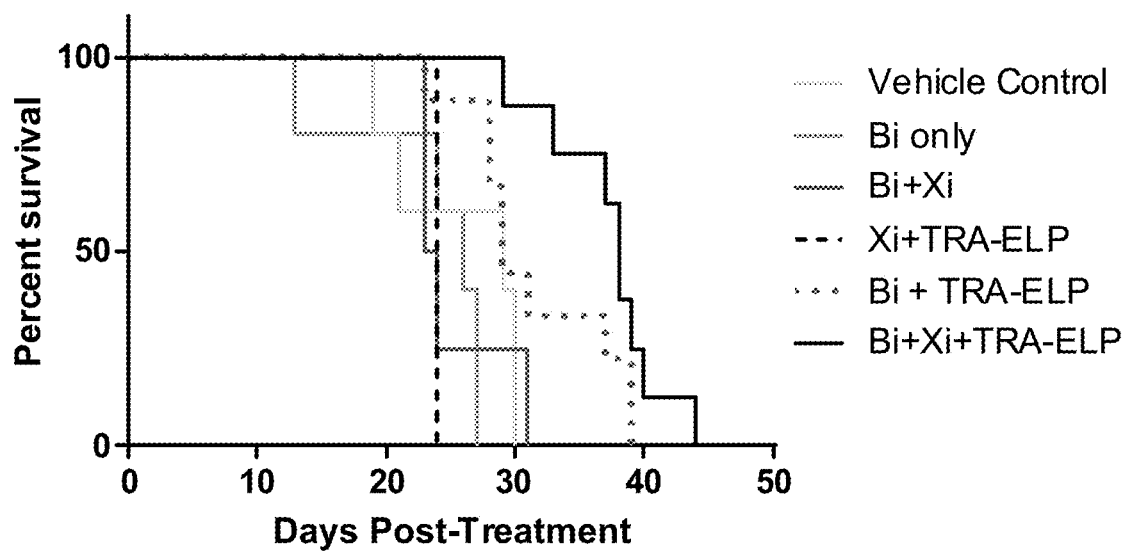
Figure 23:
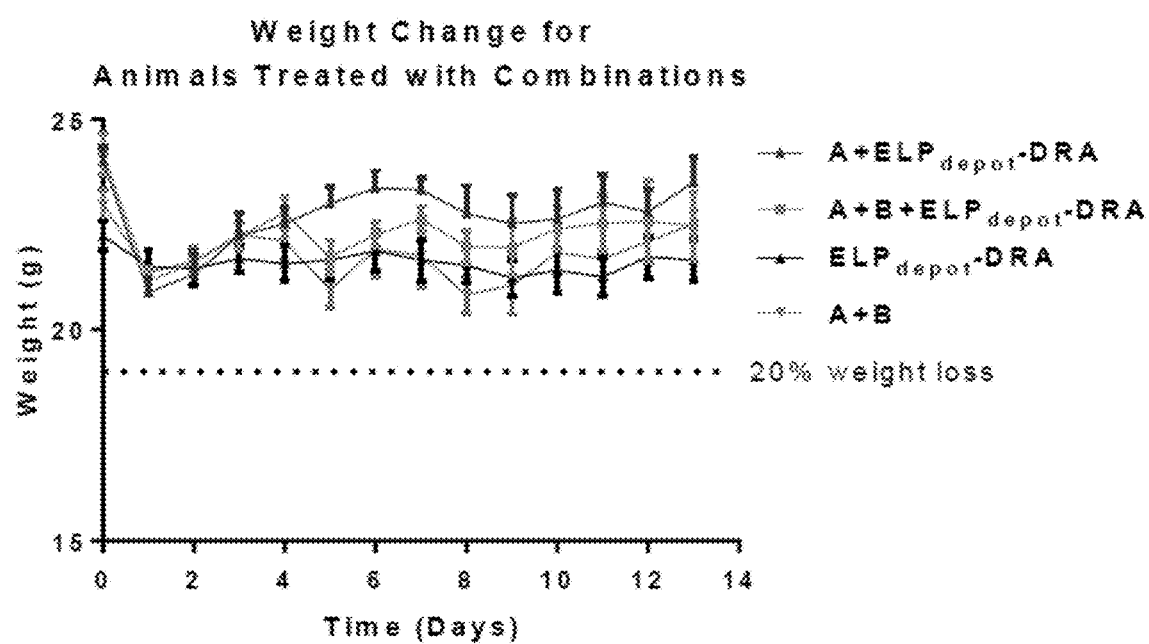
FIG. 23 is a graph showing the combination of DRA with XIAP and BCL-XL inhibitors is well tolerated in vivo in nude mice implanted with patient-derived xenografts. The mice in the ELP$_{depot}$-DRA-only, double (A-1331852+ELP$_{depot}$-DRA and A-1331852+BV6), and triple (A-1331852+BV6+ELP$_{depot}$-DRA) treatment groups experienced some weight loss (<15%) the day after treatment commences, but as the study continued, they experienced weight gain and plateau. Weight loss did not exceed 20%.

To assess in vivo efficacy of the triple treatment compared to single drugs or double combinations, a tumor growth study was performed in highly DRA-resistant CRC247 patient-derived s.c. xenografts. Having established the superior efficacy of the ELP depot for sustained DRA delivery compared to DRA by itself, the small molecule inhibitors of BCL-$X_L$ and XIAP, A-13 and BV6, in combination with the $ELP_{depot}$-DRA formulation in vivo were tested. The doses for each drug were chosen based on information available, observation from a pilot toxicity study, and the DRA doses known to be efficacious in DRA-sensitive cell lines. The triple drug combination effectively resulted in tumor regression for one week and delayed tumor growth between days 5 and 13 compared to all other groups (FIG. 20B and FIG. 20C). Treatment with single drugs, A-13 (daily p.o. 25 mg/kg), BV6 (q4d i.p. 5 mg/kg), or $ELP_{depot}$-DRA (30 mg/kg s.c. weekly), resulted in slowed tumor growth compared to mice in the vehicle control group, but the A+B+$ELP_{depot}$-DRA triple drug treatment was much more efficacious at suppressing tumor growth (FIG. 20B). Treatment with the double drug combinations A-13+BV6, BV6+$ELP_{depot}$-DRA, and A+$ELP_{depot}$-DRA were well tolerated (FIG. 23) and slowed tumor growth, but addition of the third drug in the A-13+BV6+$ELP_{depot}$-DRA treatment group resulted in more profound tumor growth inhibition over time (FIG. 5C). Survival data corroborated the advantage of having all three drugs in combination, as mice in this group outlived those in all other groups (FIG. 20D). These in vivo results qualitatively recapitulated those seen in vitro, providing affirmative evidence for the utility of this triple drug combination for treatment of a DRA-resistant PDX in mice.

In these studies, solutions were presented to the potency, resistance, and delivery challenges that hinder proapoptotic receptor agonist efficacy. Maximization of potency was achieved through use of a hexavalent DRA that promoted multimeric DR5 receptor crosslinking and efficient pathway engagement. To address the intrinsic resistance of a subset of CRCs to DRA treatment, an unbiased CRISPR screen in a DRA-resistant CRC was carried out, which identified genes that, when knocked out, overcome intrinsic resistance to the DRA. This unbiased approach did not tailor combination options to conventional knowledge of signaling pathways associated with the drug of interest, and instead scanned a plethora of potential cancer death and survival pathways to evaluate the most important mechanisms of resistance. Interestingly, among the many cancer pathways interrogated in the screen, the majority of primary hits were genes within the extrinsic/intrinsic pathways, suggesting that failure of DRA monotherapies is driven by an inability to fully engage the cell death machinery. While a number of regulators of the extrinsic apoptotic pathway were conceivably potential drivers of intrinsic DRA resistance, the rational and unbiased genetic knockout screen considerably narrowed down the key players to a shortlist of druggable targets, a task that would be infeasible to conduct in an in vivo model. The screen nominated the gene for XIAP, an antiapoptotic protein, as the greatest driver of resistance to both TRAIL and DRA in human colorectal cancer cell line RKO. The identification of XIAP as a driver was consistent with studies in the literature that have suggested XIAP as a key driver of TRAIL resistance. The emergence of the anti-apoptotic protein BCL-$X_L$ as a hit was also consistent with our mechanistic understanding of apoptotic signaling.

The genetic screen streamlined the testing of potential targeted small molecules that specifically inhibit proteins associated with DRA resistance instead of simply combining DRA with standard-of-care chemotherapeutics. The "druggable" targets were linked to associated, clinically viable small molecule drugs and tested in combination with DRA to identify the cocktails that most effectively overcome DRA resistance. Most notably, these studies nominated BCL-$X_L$ inhibition, with or without XIAP inhibition, as a potent strategy for sensitizing tumors to DRA. Although, BCL-$X_L$ and XIAP are well-known inhibitors of TRAL-mediated apoptosis, previous colon cancer-focused studies have been limited to in vitro studies using RNAi knockdown of these targets in just a few cell lines. Interestingly, the combination studies herein included the observation that cancer cells with intrinsic resistance to DRA alone (RKO, CR247, and CRC119) could be strongly sensitized to death receptor agonism using combined IAP and BCL-$X_L$ inhibition, whereas normal cell with similar intrinsic insensitivity to DRA could not.

Having addressed the in vitro potency and resistance issues of the DRA, a DRA fusion was engineered with a thermally responsive ELP to create an injectable depot formulation, $ELP_{depot}$-DRA, for sustained delivery of the DRA in vivo. The efficacy of this depot was demonstrated by the significant anti-tumor activity of the ELP-DRA gel depot formulation in the DRA-sensitive Colo205 model following only a single injection. Notably, the $ELP_{depot}$-DRA outperformed the DRA, which was soluble upon s.c. administration and was rapidly cleared from systemic circulation by renal clearance, highlighting the importance of temporally sustained delivery of drugs such as biologics that are typically systemically injected. Finally, the two strategies were integrated to achieve in vivo tumor growth inhibition of DRA-resistant patient-derived xenografts (PDX), demonstrating significant anti-tumor efficacy when combining BCL-$X_L$ inhibition with A-1331852, with or without, the XIAP inhibitor BV6, with the ELP-DRA conjugate. This work is the first example of pharmacologic inhibition of BCL-$X_L$ BCL-$X_L$ and XIAP to overcome resistance to extrinsic pathway agonism in vivo in patient-derived xenograft (PDX) models.

A major potential limitation of most combination antitumor therapies like A-1331852/BV6/DRA is toxicity. The doses used in this study were based on a small pilot maximum tolerated dose (MTD) experiment and were not fully optimized, and a rigorous optimization study may enable lowering of drug doses. In addition, instead of daily dosing of the death receptor agonist, the slow release formulation enabled DRA administration only once per week. This aspect of this work is encouraging, especially because the major reported dose-limiting toxicities (DLTs) for each class of drug used in this study do not overlap with one another. Thus, by taking advantage of their highly synergistic anti-tumor activity, the therapeutic combinations described here have the potential to be safely administered to patients at active doses. The significance of the current study is not intended to be driven by the biological novelty of the resistance mechanisms, but rather by the modular integration of solution to the problems of potency, bioavailability, and drug resistance.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A composition comprising a TRAIL receptor agonist and at least two sensitizing agents selected from the group consisting of BV6, A-1331852, WEHI-539, and Palbociclib, wherein the TRAIL receptor agonist comprises 6 type III fibronectin domains connected to one another with flexible glycine-serine linkers and each fibronectin domain comprises SEQ ID NO: 1, and wherein the TRAIL receptor agonist is fused with an elastin-like polypeptide (ELP) comprising an amino acid sequence of (VPGXG)$_n$ (SEQ ID NO: 3), wherein X is any amino acid except proline and n is an integer greater than or equal to 1.

2. The composition of claim 1, wherein at least one of the flexible glycine-serine linkers comprises SEQ ID NO: 2.

3. The composition of claim 1, wherein n is between 60 and 180.

4. The composition of claim 1, wherein X is valine.

5. The composition of claim 1, wherein the at least two sensitizing agents comprise BV6 and A-1331852.

* * * * *